United States Patent [19]
Roos et al.

[11] Patent Number: 5,840,338
[45] Date of Patent: Nov. 24, 1998

[54] LOADING OF BIOLOGICALLY ACTIVE SOLUTES INTO POLYMER GELS

[76] Inventors: Eric J. Roos, 1 Barbara Jean St., Grafton, Mass. 01519; Matthew E. Schiller, 23C Sagamore Way, Waltham, Mass. 02154

[21] Appl. No.: 556,130

[22] Filed: Nov. 6, 1995

Related U.S. Application Data

[63] Continuation-in-part of Ser. No. 276,462, Jul. 18, 1994, Pat. No. 5,603,955, and a continuation-in-part of Ser. No. 276,193, Jul. 18, 1994.

[51] Int. Cl.$^6$ ............................. A61K 9/10; A61K 47/36; A61K 47/34
[52] U.S. Cl. ...................... 424/488; 424/486; 424/487; 424/484; 514/944; 252/315.2; 252/315.4; 252/315.3
[58] Field of Search ................... 424/486, 484, 424/488, 487

[56] References Cited

U.S. PATENT DOCUMENTS

| | | |
|---|---|---|
| 3,077,468 | 2/1963 | Geurden . |
| 3,379,720 | 4/1968 | Wilmington . |
| 3,458,622 | 7/1969 | Hill . |
| 3,993,553 | 11/1976 | Assarsson et al. . |
| 4,002,173 | 1/1977 | Manning et al. . |
| 4,004,997 | 1/1977 | Tsukamoto et al. . |
| 4,172,066 | 10/1979 | Zweigle et al. . |
| 4,428,972 | 1/1984 | Wurzburg et al. . |
| 4,462,982 | 7/1984 | Samejima et al. . |
| 4,474,751 | 10/1984 | Haslam et al. . |
| 4,474,752 | 10/1984 | Haslam et al. . |
| 4,555,344 | 11/1985 | Cussler . |
| 4,881,798 | 11/1989 | Yuasa et al. . |
| 5,093,030 | 3/1992 | Ito et al. . |
| 5,252,318 | 10/1993 | Joshi et al. . |
| 5,259,998 | 11/1993 | Reich et al. . |
| 5,395,620 | 3/1995 | Huc et al. . |

FOREIGN PATENT DOCUMENTS

| | | |
|---|---|---|
| 0 178 665 | 4/1986 | European Pat. Off. . |
| 5-239263 | 9/1993 | Japan . |
| 2177 708 | 1/1987 | United Kingdom . |
| WO 92/13566 | 8/1992 | WIPO . |
| WO 93/19095 | 9/1993 | WIPO . |
| WO 93/19115 | 9/1993 | WIPO . |

OTHER PUBLICATIONS

Gehrke et al., "Enhanced Protein Loading in Hydrogels", Chemical Abstracts, 119:233955f (1993).
Gehrke et al., "Hydrogels for Drug Delivery System", CA 112:164791 (1990).
Gehrke et al., "Protein Isolation by Solution–Controlled Gel Sorption", CA 115:69868 (1991).
Palasis et al., "Permeability of Responsive Poly(N–isopropylacrylamide) Gels to Solutes", CA 116:91247 (1992).
Harsh et al., "Modeling Swelling Behavior of Cellulose Ether Hydrogels", CA 119:79961 (1993).
Gehrke et al., "Enhanced Protein Loading in Hydrogels", Derwent Abstract, JP 5239262, CA 119:233955 (1993).
Kamath et al., "Preliminary Study on the Controlled Delivery of a Bioactive Protein from Dextran Hydrogels", Proceed. Intern. Symp. Control. Rel. Bioact. Mater., 20, pp. 111–112 (1993).
Gehrke et al., "Enhanced Protein Loading in Hydrogels", Proceed. Intern. Symp. Control. Rel. Bioact. Mater., 20, pp. 113–114 (1993).
Gehrke et al., "Protein Isolation by Solution–Controlled Gel Sorption", Biotechnol. Prog., 7, pp. 355–358 (1991).

(List continued on next page.)

*Primary Examiner*—Edward J. Webman
*Attorney, Agent, or Firm*—Choate, Hall& Stewart

[57] ABSTRACT

Polymer gel networks loaded with biologically active solutes in a manner that solute activity is maintained and protected from thermal and/or chemical degradation while in the gel network are provided. The invention also provides for effects of modulating parameters for loading safe responsive gel networks using loading solutions containing phase separating polymers.

29 Claims, 12 Drawing Sheets

OTHER PUBLICATIONS

Palasis et al., "Permeability of Responsive Poly(N–isopropylacrylamide) Gel to Solutes", Jour. of Controlled Release, 18, pp. 1–12 (1992).

Skuse et al., "Hydroxypropyl Cellulose/Poly(Ethylene Glycol)–Co–Poly(Propylene Glycol) Aqueous Two–Phase Systems: System Characterization and Partition of Cells and Proteins", Enzyme Microb. Technol., vol. 14, pp. 785–790 (Oct. 1992).

Harsh et al., "Controlling the Swelling Characteristics of Temperature–Sensitive Cellulose Ether Hydrogels", Jour. of Controlled Release, 17, pp. 175–185 (Oct. 1991).

Kim et al., "Hydrogels: Swelling, Drug Loading, and Release", Pharmaceutical Research, vol. 9, No. 3, pp. 283–290 (1992).

Autonsen et al., "Controlled Release of Proteins from 2–Hydroxyethyl Methacrylate Copolymer Gels", Biomat. Art. Cells & Immob. Biotech., 21(1), pp. 1–22 (1993).

American Chemical Society, "Polymeric Materials Science and Engineering", vol. 63, pp. 329–336 (Fall Meeting, 1990).

Gref et al., "Biodegradable Long–Circulating Polymeric Nanospheres", Science, vol. 263, pp. 1600–1603 (Mar. 18, 1994).

American Institute of Chemical Engineers, Extended Abstracts 153i, Vaid et al., Isolation of Proteins by Selective Gel Sorption (Nov. 1, 1992).

Amiya et al., "Phase Transitions in Cross–Linked Gels of Natural Polymers", Macromolecules, vol. 20, pp. 1162–1164 (1987).

Harsh et al., "Modeling Swelling Behavior of Cellulose Ether Hydrogels", Polymeric Delivery Systems, Chapter 7, pp. 105–134 (1993).

Peppas, Hydrogels in Medicine and Pharmacy, vol. II Polymers, Chapter 5, pp. 115–160 (1987).

Gehrke, "Synthesis, Equilibrium Swelling, Kinetics, Permeability and Applications of Environmentally Responsive Gels", vol. II Transitions, Springer–Verlag, pp. 81–141.

Harsh, "Controlling Swelling Behavior of Novel Cellulose Ether Hydrogels", Dissertation, University of Cincinnati, pp. i–v; pp. 1–136 (1992).

Before　After

LOADING OF BIOLOGICALLY ACTIVE SOLUTES INTO POLYMER GELS

CROSS-REFERENCE TO RELATED APPLICATION

This application is a continuation-in-part application of U.S. Ser. Nos. 08/276,462, filed Jul. 18, 1994, and 08/276,193, filed Jul. 18, 1994, now U.S. Pat. No. 5,603,955, now pending, and the entire contents of which are incorporated herein by reference.

TECHNICAL FIELD

The present invention generally relates to the loading of biologically active solutes such as proteins, polypeptides, nucleoproteins, glycoproteins and lipoproteins into polymer gels such that the biologically active solutes loaded into the gels exhibit thermal and chemical stability. The present invention more particularly relates to applications utilizing polymer gels loaded with biologically active solutes in a manner that solute activity is maintained and protected from thermal and/or chemical degradation while in the gel network.

BACKGROUND OF THE INVENTION

Three-dimensional polymer gel networks have been widely studied for use as delivery vehicles for a variety of solutes, most particularly biologically active solutes.

Many methods of loading gels with solutes are presently available. Two of them relevant to drug loading include: (i) formation of the hydrogel in the presence of the solute (e.g., drug); and (ii) swelling of a preformed gel in a concentrated solution of the solute (e.g., drug). See, for example, Kim et al., *Phar. Res.* 9: 283–289 (1992). Maximum loadings of high molecular weight solutes are generally on the order of about a few percent by weight of gel. Each of these techniques has serious limitations. In the first method, side reactions are possible between moieties reacting to form the hydrogel and the drug and it is often not possible to remove extractable materials from the gel after its formation without also extracting the drug. In the second method, solubility limitations become a drawback. That is, many drugs are sparingly soluble in water, and drug loading must be accomplished in non-aqueous solvents or water/solvent solutions. Since most naturally-occurring proteins, and proteins obtained from recombinant DNA techniques, are denatured or otherwise inactivated in non-aqueous solvents, this second method is not suitable for loading many biologically active materials. Moreover, large molecular weight materials (e.g., polypeptides) may be physically excluded from the hydrogels.

Partial denaturation of solutes such as vitamins, enzymes and the like is sometimes tolerated in purification/separation procedures since various methods have been developed to renature, or at least, reactivate the biologically active solute (s) once it has been purified. See, for example, Knuth and Burgess, "Purification of Proteins in the Denatured State", *Protein Purification: Micro to Macro*, pp. 279–305, Alan R. Liss, Inc., 1987. In separation/purification procedures protection of a particular solute (e.g., isolated enzyme, protein, vitamin) from inactivation during purification/separation procedure is preferred. In the drug delivery arts, it is counterproductive to even partially denature a biologically active solute once it is disposed on, or in, a delivery device since the solute must function when released.

Gref et al., *Science*, 263: 1600–1602 (1994) have developed biodegradable nanospheres using amphiphilic co-polymers that phase-separate during emulsification. Loadings up to 45 percent by weight of a biologically active solute were achieved by dissolving the solute in the same organic solvent that dissolved the copolymer. Although loading is high using this method, the solute must be dissolved in a possible denaturant, i.e., an organic solvent.

Significantly, high loadings may lead to deactivation in other ways. For example, it is known that high levels of insulin are often used for insulin implants and controlled release devices. Reactions between the insulin molecules that are at high concentration lead to agglomeration and subsequent denaturation of the insulin. Furthermore, the manufacture of gel-based delivery devices will often require a drying step if the loaded gels are to be stored in their dry state between manufacture and use. Denaturation of the biologically active solute can also occur as a result of drying the gel.

What is required is a device and a method for loading effective amounts of solutes into polymer gel networks and that also avoid problems associated with denaturation or inactivation of the solute during, and after loading.

Volumetric change phenomena have been observed in three-dimensional, permanently crosslinked polymer gel networks. As an external environmental condition (e.g., temperature, solvent composition, pH, electric field, light intensity and wavelength, pressure, ionic strength) is changed, the polymer gel network contracts and/or expands in volume. The volume of such a gel may, under certain circumstances, change reversibly by a factor as large as several hundred when the gel is presented with a change in external conditions (i.e., the gel is a "responsive" gel). Tanaka, *Physical Review Letters*, Vol. 40, no. 12, pp. 820–823, 1978 and Tanaka et al, *Physical Review Letters*, Vol. 38, No. 14, pp 771–774, 1977; Tanaka et al *Physical Review Letters* 5, Vol 45, pg. 1636, 1980; Ilavsky, *Macromolecules*, Vol. 15, pg. 782, 1982; Hrouz et al, *Europ. Polym. J.*, Vol. 17, pg. 361, 1981; Ohmine et al, *J. Chem. Physics*, Vol. 8, pg. 6379, 1984; Tanaka et al, *Science*, Vol. 218, pg. 462, 1982; Ilavsky et al, *Polymer Bull.* Vol. 7, pg. 107, 1982; Gehrke, "Responsive Gels:Volume Transitions II"; ed. K. Dusek, Springer-Verlag, New York, pp. 81–144 (1993); Li et al., *Ann. Rev. Mat. Sci.,* 22: 243–277 (1992); and Yu et al., *Enzyme Microb. Technol.,* 15: 354–366 (1993), all of which are incorporated herein by reference.

A number of significant studies have demonstrated the potential of responsive gels in solute/solvent separations (Cussler, U.S. Pat. No. 4,555,344) and in biomedical applications (Hoffman, U.S. Pat. No. 4,912,032). In spite of this, responsive gels have failed to become commercially useful for two major reasons. Synthesis of a gel may utilize monomers and/or polymers whose toxicologic hazard characteristics are ill-defined (e.g., N-isopropylacrylamide (NIPA) and related acrylic monomers, polymers and co-polymers). Second, synthesis of a gel may use crosslinkers known to be toxic (e.g., divinyl sulfone (DVS), glutaraldehyde, divinyl benzene, N-N-methylenebisacrylamide, and the like). Harsh and Gehrke (*J. Control. Rel.,* 17: 175–186, 1991), incorporated herein by reference, have created certain gels based on cellulose ether polymeric precursor materials. These cellulosic ether precursor materials are currently acceptable by the U.S. Food and Drug Administration but these gels were made using toxic DVS crosslinkers that are not FDA acceptable. One way to avoid use of toxic chemical crosslinkers is by use of radiation crosslinking. This method is problematic inasmuch as it may lead to the presence of unreacted monomers.

While it is certainly possible that currently available, chemically crosslinked gel materials can prove to be biologically compatible for in vivo use (see e.g., "Hydrogels in Medicine and Pharmacy", N. A. Peppas and B. D.Barr-Howell (eds), Vol. 1 and 2, CRC Press, Boca Raton, Fla. (1986)), the existing regulatory environment and the myriad of tests required to characterize the toxicity of such materials place major barriers to commercialization of responsive gels.

SUMMARY OF THE INVENTION

It has now been discovered that biologically active solutes such as proteins, polypeptides, nucleoproteins, glycoproteins and lipoproteins can be loaded into safe, responsive crosslinked polysaccharide gel networks and demonstrate activity after exposure to thermal and chemical challenges. Applications for loaded biologically active solutes into safe, responsive crosslinked polysaccharide gel networks include, but are not limited to, cosmetic formulations using papain, therapeutics such as peroxidase catalyzed antibacterials or oral hepatitis B vaccine, over the counter products using peroxidase catalyzed antibacterials in mouthwash or toothpaste that require protection of an enzyme from formulation excipients such as sodium dodedcyl sulfate, lactose intolerance medications, stabilization of molecular biology enzymes such as restriction endonucleases allowing for greater shipping and storage flexibility with respect to temperature, loading of enzymes into gel networks for use in blood panel diagnostics or other types of diagnostics including the use of luciferase and ATP (adenosine triphosphate) and the use of loaded enzymes for bioremediation including the clean up of hydrazine spills with specific hydrazine degrading enzymes.

The present invention also describes the effects of modulating parameters for loading safe responsive crosslinked polysaccharide gel networks such as hydroxy propyl cellulose crosslinked with adipic acid using loading solutions containing PVA (poly vinyl alcohol) or PLURONIC® (such as PLURONIC® P105, commercially available from BASF) as phase separating polymers at varying concentrations having a pH above and below the isoelectric point of the protein to be loaded with either potassium iodide or potassium fluoride at varying concentrations. As used herein, PLURONIC® includes difunctional block-polymers terminating in primary hydroxyl groups with molecular weights ranging from 1,000 to above 15,000. PLURONIC® polymers are polyoxyalkylene derivatives of propylene glycol.

The present invention is based, on the discovery that: (i) unexpectedly high loadings (up to forty percent) mass solute/polymer gel mass can be obtained by modifying a two phase aqueous extraction protein purification method; and (ii) methods for maintaining activity of a solute of choice from denaturation within a crosslinked gel may be accomplished by trapping protectant moieties directly into the crosslinked gel. Both aspects of the invention are accomplished in a single step and can work synergistically.

One aspect of the invention is a method of loading a solute into a crosslinked polymer gel network. The method includes the steps of contacting the biologically active solute with: (i) a gel network that incorporates a solvent; and (ii) a loading solution that contains a polymer soluble in the same solvent incorporated into the gel network, under conditions sufficient for the solute to selectively partition into the gel and for the solute to retain its activity within the gel. Most preferably, the solute is a biologically active solute and the crosslinked gel is a gel responsive to a change in an environmental condition to which the gel is exposed. The loading polymer may be a linear or branched polymer. A salt is preferably included to enhance partitioning of the solute into the gel.

A further embodiment is a method for delivering a preferred biologically active solute to an environment of use. The method includes partitioning at least one biologically active solute into a responsive polymer gel by the methods of the inventions and then triggering an expansion or collapse of the polymer gel under conditions sufficient to release at least one biologically active solute into the environment of use.

Compositions of the invention include three-dimensional, responsive polymer gel networks containing a protectant moiety and an amount of solute equal to as much as forty percent mass solute/polymer gel mass. The gel networks are made by contacting the solute with:(i) a gel network; (ii) a loading polymer that is somewhat immiscible with the gel; and (iii) a optionally, a salt. Conditions are chosen so that the solute selectively partitions into the gel. The gel is then separated from the other components.

In preferred embodiments of the invention, the network is a responsive polymer gel and the protectant moiety is a salt or a linear polymer, either alone or in combination. The compound is a biologically active solute and may be a solute having a molecular weight greater than about 1,000 and is preferably selected from the group including proteins, polypeptides, nucleoproteins, glycoproteins and lipoproteins.

Another embodiment of the invention are hydrogels whose water soluble polymeric starting materials can be used in the method. Exemplary materials include polyethylene oxide, polyethylene glycol, polyvinylalcohol, methylcellulose, dextran, hydroxypropyldextran and ethylhydroxyethylcellulose, and polyvinylpyrolidone, hydroxypropylcellulose, hydroxypropyl starch, and polypropylene glycol.

A drug delivery system is also included within the scope of the invention and comprises a polymer gel network including the drug to be delivered; a salt; and a loading polymer. The salt and the loading polymer are capable of protecting the drug from loss of activity. The polymer gel network is capable of expanding or collapsing in response to a change in an environmental condition to which the gel is exposed, the expanding or collapsing sufficient to release the drug into an environment of use.

A further embodiment of the invention is a wound dressing comprising a responsive polymer network having incorporated therein a medicament and a protectant, the network constructed such that a change in an environmental condition to which the gel is exposed releases the medicament to a wound site. Preferred responsive polymer networks for use in wound dressings include a medicament to be delivered; a salt; and a loading polymer, the salt and the loading polymer capable of protecting the medicament from loss of activity while in the wound dressing.

An iontophoretic drug delivery system of the invention comprises a polymer network including a drug to be delivered; a salt; and a loading polymer. The salt and the loading polymer are capable of protecting the drug from loss of activity.

A method of maintaining activity of a solute in a crosslinked polymer gel network is also described. The method includes introducing a protectant molecule and a solute that has biological and/or chemical activity into a polymer by contacting a solution of the solute with a gel and a protectant solution comprising a loading polymer and a salt where the loading polymer may be subjected to be the protectant. The contacting step is performed under conditions sufficient for the solute and the protectant molecules to selectively partition into the gel so that the activity of the solute is maintained during and after partitioning.

A variety of controlled release devices incorporate loaded responsive polymer gels of the present invention. One device includes the gel of the invention and is adapted to deliver a pest control substance when exposed to a change in an environmental condition. Another device is adapted to deliver a cleaning substance selected from the group consisting of an enzyme, a detergent, a bleach, when exposed to a change in an environmental condition. Yet another device is adapted to deliver an organic solvent, when exposed to a change in an environmental condition.

The invention has significant advantages. Common solvents, such as water, may be used in which all components are sufficiently soluble. Complete incompatibility and immiscibility of gel and loading polymers using the present technique is not required since the crosslinked polymer gel is always readily separable from the surrounding solutions. The gel protects labile solutes from denaturing conditions present outside the gel. The technique is readily generalizable to more than one gel phase multiple loading polymers, and different solutes.

It is therefore an object of the invention to provide a method of loading pharmaceutically-effective amounts (up to forty percent mass solute/polymer gel mass) into a crosslinked gel.

It is a further object of the invention to provide a method for protecting a solute while the solute is within a crosslinked gel.

It is another object of the invention to provide a method for trapping protectant moieties directly into a crosslinked gel and loading the gel with a biologically active solute in a single step.

It is another object of the present invention to provide a gel delivery system that overcomes the limitations of solute size on loading into hydrogels.

It is a further object of the invention to provide a gel for solute release that can be designed for optimal release independent of conditions for effective loading of the solute.

It is an another object of the present invention to provide responsive polymer gels that are environmentally safe and safe for use in humans.

It is another object of the invention to provide methods for making crosslinked, responsive polymer gels in which the crosslinker and polymer are acceptable to governmental regulatory agencies as safe for use in humans.

It is another object of the present invention to provide means and conditions leading to high loading of environmentally safe, responsive crosslinked polysaccharide gel networks.

One embodiment of the invention is a crosslinked, responsive polymer gel network comprising polymer chains interconnected by way of multifunctional crosslinker. The polymer chains and crosslinker have a known acceptable toxicological profile, hereinafter "KATP". Another embodiment is a crosslinked, responsive polymer gel network comprising polymer chains interconnected by way of KATP crosslinkages. A third embodiment of the invention is a crosslinked, responsive polymer gel network comprising polymer chains interconnected by way of a crosslinker, in which each of the polymer and crosslinker is obtainable from a precursor that is used in a process for making a material that has a KATP. The gels have the characteristic that, when leached, the leachate from the network also has a KATP as well as any residual elements in the network. The gel solvent also may have a KATP.

A preferred responsive polymer gel network are polysaccharide chains crosslinked with a multifunctional carboxylic acid obtainable from an acyl halide derivative of said acid. The preferred polymer chaims may include starch or cellulose ethers and the preferred multifunctional carboxylic acid is selected from the group consisting of adipic acid, sebacic acid, succinic acid, citric acid, 1,2,3,4-butanetetracarboxylic acid, and 1,10 decanedicarboxylic acid. Particularly preferred cellulose ethers are hydroxyethylcellulose, hydroxypropylcellulose, and hydroxypropylmethylcellulose.

The gels may be responsive to a variety of triggers such as temperature or pH. In particular, the pH-response may be triggered by a change in an environmental condition to which the gel is exposed, such as a change in ion concentration, solvent concentration, or electromagnetic radiation.

Methods for making crosslinked polymer networks include selecting a polymeric starting material capable of being crosslinked, wherein the polymeric starting material selected for the particular use has a known acceptable toxicological profile for the particular use or for a related use; selecting a crosslinker capable of crosslinking the polymeric starting material, wherein the crosslinker selected for the particular use has a known acceptable toxicological profile for the particular use or for a related use; and contacting the crosslinker and polymeric starting material under conditions sufficient to form the three-dimensional, crosslinked polymer network.

Another method involves selecting a crosslinker capable of crosslinking the polymeric starting material, so that the resulting network, after formation, contains a crosslinkage that has a known acceptable toxicological profile. Preferred methods include the steps of contacting a crosslinker comprising an acyl halide derivative of a multifunctional carboxylic acid with a polysaccharide under conditions sufficient for the three-dimensional, polymer gel network to form so that the gel network includes polysaccharide chains crosslinked with the acid. Preferred methods use a polysaccharide selected from starch and cellulose ethers of various types, including hydroxyethylcellulose, hydroxypropylcellulose, hydroxypropylmethylcellulose and modified food starch.

The preferred methods use a crosslinker that is an acyl chloride derivative of a multifunctional carboxylic acid selected from the group consisting of adipic acid, sebacic acid, succinic acid, 1,2,3,4-butanetetracarboxylic acid, and 1,10 decanedicarboxylic acid.

Other methods of the invention include a method of separating a substance from a solution. A KATP polymer gel network of the invention capable of incorporating the substance from a solution containing the substance is introduced into the solution and a volumetric change of the gel is induced by changing an environmental condition to which the gel is exposed so that the gel incorporates the substance and separates the substance from the solution. A further method includes introducing a KATP polymer gel network of the invention that is capable of excluding a substance from a solution containing the substance. The gel is induced to undergo a volumetric change by changing an environmental condition to which the gel is exposed so that the gel excludes the substance and separates the substance from the solution.

A method of delivering a substance into an environment of use includes the steps of incorporating the substance into the KATP polymer network of the invention and inducing a volumetric change in the network by changing an environmental condition to which the network is exposed so that the network disgorges the substance to the environment of use.

Similarly, a method for removing a substance from an environment containing a the substance includes introducing into the environment a KATP polymer network of the invention that contains a ligand reactive with the substance when the ligand is exposed to the substance and changing an environmental condition of the network to cause a volumetric change and expose the ligand to the substance, so that the substance is incorporated into the gel.

A method of loading a solute into a KATP polymer gel network includes contacting the solute with the KATP gel, a second polymer, and a salt under conditions sufficient for the solute to selectively partition into the first polymer.

A cosmetic composition, wound dressing, pharmaceutical composition, monitoring electrode, adhesive device and iontophoretic device, dialysis device, including the KATP polymer network, are also intended to be encompassed within the scope of the invention.

The KATP responsive gel networks of the invention have the singular advantage of having toxicological profiles which are more readily evaluated than prior art responsive gels. Thus, the present responsive gels may be used as environmentally benign materials which may be easily recycled for many commercial purposes and which may be used in the human body.

The foregoing has outlined some of the more pertinent objects of the present invention. These objects should be construed to be merely illustrative of some of the more prominent features and applications of the invention. Many other beneficial results can be attained by applying the disclosed invention in a different manner of modifying the invention as will be described. Accordingly, other objects and a fuller understanding of the invention may be had by referring to the following Description of the Preferred Embodiments.

BRIEF DESCRIPTION OF THE DRAWINGS

For a fuller understanding of the present invention, reference is had to the following description taken in conjunction with the accompanying drawings, in which.

Figure 1:
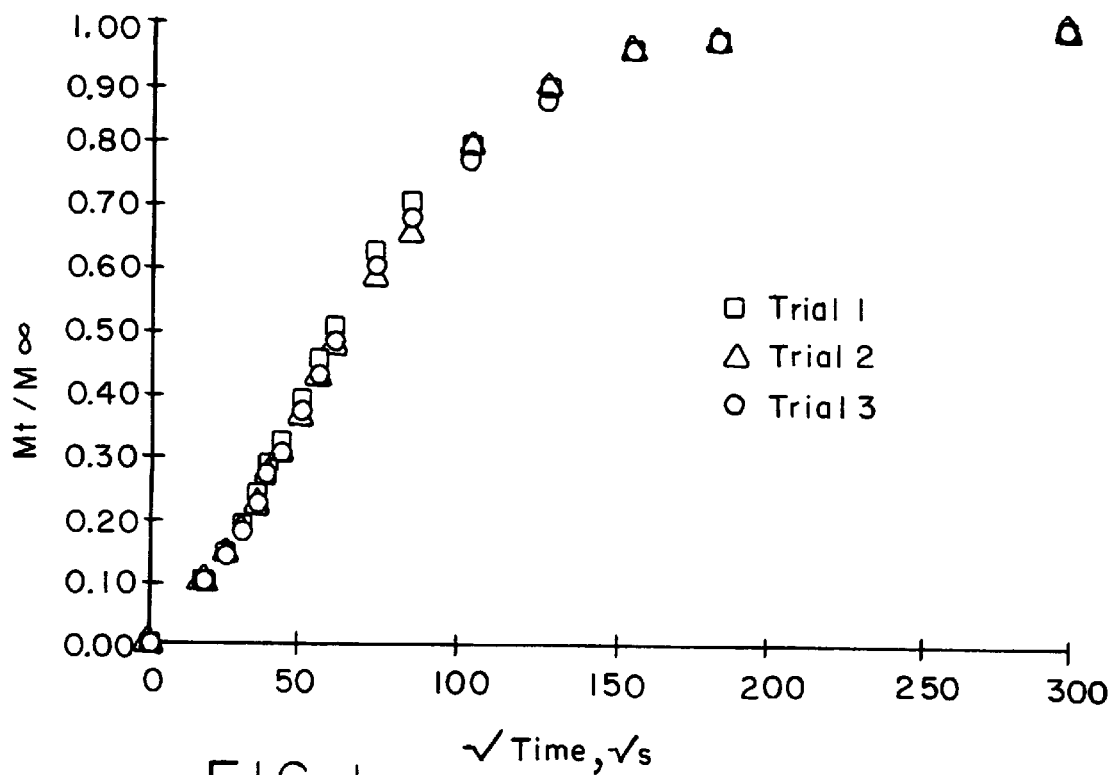
FIG. 1 is illustrates release kinetics of amylase from a dextran gel. The Y axis is the release at a given time divided by total amount released at equilibrium.

Similar reference characters refer to similar parts throughout the several views of the drawings.

DESCRIPTION OF THE PREFERRED EMBODIMENTS

It has now been discovered that biologically active solutes can be loaded into a safe, responsive crosslinked polysaccharide gel networks and demonstrate activity after exposure to thermal and chemical challenges. The biologically active solute may be a solute having a molecular weight greater than about 1,000 and is preferably selected from the group including proteins, polypeptides, nucleoproteins, glycoproteins and lipoproteins. Applications for loaded molecules into safe responsive crosslinked polysaccharide gel networks include, but are not limited to, cosmetic formulations using papain, therapeutics such as peroxidase catalyzed antibacterials or oral hepatitis B vaccine, over the counter products using peroxidase catalyzed antibacterials in mouthwash or toothpaste that require protection of an enzyme from formulation excipients such as sodium dodedcyl sulfate, lactose intolerance medications, stabilization of molecular biology enzymes such as restriction endonucleases allowing for greater shipping and storage flexibility with respect to temperature, loading of enzymes into gel networks for use in blood panel diagnostics or other types of diagnostics including the use of luciferase and ATP (adenosine triphosphate) and the use of loaded enzymes for bioremediation including the clean up of hydrazine spills with specific hydrazine degrading enzymes.

The present invention also describes the effects of modulating parameters for loading safe responsive crosslinked polysaccharide gel networks such as hydroxy propyl cellulose crosslinked with adipic acid using loading solutions containing PVA (poly vinyl alcohol) or PLURONIC® (PLURONIC® P105 is commercially available from BASF) as phase separating polymers at varying concentrations having a pH above and below the isoelectric point of the protein t be loaded with either potassium iodide or potassium fluoride at varying concentrations. As used herein, PLURONIC® includes difunctional block-polymers terminating in primary hydroxyl groups with molecular weights ranging from 1,000 to above 15,000. PLURONIC® polymers are polyoxyalkylene derivatives of propylene glycol.

The present invention pertains to methods of loading solutes, most preferably biologically active solutes, into polymer gels, the resulting polymer gels, and methods of using the loaded polymer gels. The term "enhanced loading" of solutes refers to the discovery that one can, in a single step, obtain loadings of large or small solutes into a crosslinked polymer gel and establish a gel environment conducive to maintaining the activity of the solute while it is in the gel. These two objectives, both of significance in the drug separation/purification and drug delivery arts, may simultaneously be accomplished by sorption of a solute into a gel, the sorption driven by addition of a water soluble, loading polymer to the solution containing the solute. It is preferred that a salt be also included in the solution. The presence of the salt and loading polymer have a synergistic effect which causes enhanced and selective partitioning (up to 40% mass solute/mass polymer gel) of the biologically active solute into the gel. Moreover, the same salt and loading polymer may be chosen as protectants to enter the gel.

The term "protectant" is meant to refer to materials that enhance the stability of the biologically active solute within the gel. For instance, it is well-known to stabilize enzymes with, for example, glycerol or other polyhydroxylated solutes such as polyethylene glycol, polypropylene glycol, and the like, or with sugar or sugar solutions (e.g., glucose, sucrose, fructose). In fact, in certain cases high protein concentrations by themselves may be their own protectants since the higher the protein concentration relative to buffer salts, the more it will act as a buffer itself. Using the present method, it is shown that biologically active solutes retain their activity after heat stress and after being released from the gel.

The present method is a modification of two-phase aqueous extraction methods for purifying proteins. In conventional two-phase aqueous extraction methods, a protein is made to selectively partition into one of two substantially immiscible aqueous polymer solution phases which are in contact with each other. This selective partitioning behavior is governed by properties such as molecular weight of the polymers and biologically active solute, the type and concentration of salts and the relative hydrophobicity/hydrophilicity of the biologically active solute. Differences in the various interaction energies between the biologically active solute and the different polymers leads to a partition coefficient (i.e., concentration of biologically active solute in the gel/concentration of the biologically active solute in the loading polymer) greater than one (i.e., preferential loading by the gel) or less than one (i.e., preferential loading by the loading polymer).

Gehrke et al., *Biotechnol. Prog.*, 7: 355–358 (1991), incorporated herein by reference, has shown that this conventional protein purification process can be extended to situations in which the gel is crosslinked dextran gel beads. This may be problematic since crosslinked polymer gels generally would be expected to exclude larger molecular weight proteins from within the gel network. See e.g., Cussler, U.S. Pat. No. 4,555,344.

A. Enhanced Solute Loading of Crosslinked Polymer Gels

A method for loading solutes into crosslinked gels is as follows: A crosslinked gel network is optionally pre-equilibrated with a solute-free, loading polymer solution. The gel is then separated from the loading polymer. To each crosslinked gel, a solution (with the same loading polymer concentration as the pre-swelling solution) including a solute to be loaded is added. The system is then agitated to mix the gel and the solute mixture. Most preferably, a salt is also added to the solute-containing solution. The gel is separated from the remaining solution. The solute concentration remaining in the loading polymer may be determined by a variety of methods, depending upon the solute of interest. For example, in spectrophotometric assays, light absorbance is measured at 280 nm for proteins; at 630 nm for blue dextran; and at 520 nm for Vitamin B12 with a UV/VIS spectrophotometer. The concentration of solute in the gel is determined by a mass balance. Dextran beads (Sephadex, registered ™) that are designed for gel filtration or size exclusion chromatography as the gel have been used. These gels are sold specifically for their protein excluding capabilities.

Preliminary partitioning experiments have been performed using crosslinked dextran beads. Prior to the protein partitioning experiments, dry gels were pre-swollen with biologically active solute-free PEG solution. Enough of the dried Sephadex gel beads were added to fritted glass centrifugation tubes to obtain about 0.6 g of gel when swollen. The centrifuge tubes were then fitted into plastic test tubes and 3 ml of PEG solution was added to each; 15 minutes was found to be sufficient for equilibration of the gel and the solution. Centrifugation (IEC Clinical Centrifuge) at roughly 400 RPM for 60 minutes was used to separate the supernatant from the swollen beads. See, Gehrke, et al., *Enhanced Protein Loading In Hydrogels*, Proceed. Intern. Symp. Control. Rel. Bioact. Meter., 20 pp. 113–114 (1993), incorporated herein by reference.

To each tube of pre-swollen gel, 1 ml of solution with the same PEG concentration as the pre-swelling solution but including the test biologically active solute was added. The tube was then agitated manually for a few minutes to allow mixing of swollen gel and solution. Equilibrium of the protein and the gel was reached in several minutes and the gel was separated from the supernatant as before. The protein concentration in the PEG was determined by measuring light absorbance at 280 nm for proteins, at 630 nm for blue dextran and at 520 nm for Vitamin B12 with UV/VIS spectrophotometer (Shimadzu UV160U). The concentration of biologically active solute in the gel was determined by a mass balance.

Solutes are recovered from the loaded gel as follows: The solute is chosen to have a very low partition coefficient in pure buffer lacking any polymer. The solute contained in the loaded gel after the partitioning experiment is recovered by adding pure buffer lacking any polymer to the loaded gel. If in bead or particulate form, the gel may be separated by centrifugation from any supernatant. Otherwise, the gel is simply removed and blotted free of solution. The concentration of the solute in the supernatant is measured using a spectrophotometer. This procedure is repeated until the solute concentration in the supernatant is negligible.

With a reversibly responsive gel, recovery of loaded solutes may be accomplished by causing the gel to undergo volumetric collapse using established methods. See for example, Cussler, U.S. Pat. No. 4,555,344, incorporated herein by reference.

Persons having ordinary skill in the art may readily use the methods described herein to test the effectiveness of particular polymers in separation and the effect of salts on the partition coefficient. Measurement of retention of biological activity of biologically active solutes is also readily accomplished using the general protocol developed herein by releasing the biologically active solute from the gel and assaying its activity. Depending on the biologically active solute, a variety of conventional assays (e.g., spectrophotometric, immunoassay, and the like) may be developed that are well within the skill level of those in the art.

Results of work presented here are summarized.

1. Dextran gel cylinders loaded with amylase using polyethylene glycol and KCl as protectants retained the amylase activity even when the loaded gel was maintained at 60 degrees C.

2. Release kinetics of amylase and ovalbumin from loaded cylindrical gels of the invention show a typical diffusion controlled release.

3. Surface adsorption of biologically active solutes in the gels is not a significant factor in loading gels and the solutes are primarily incorporated within the gel network. The clearest proof of this are the experiments performed on non-bead gels which clearly show penetration of solute and diffusion controlled release from within the gel. (see FIG. 1).

4. HPC—similar results were seen in two different cylinders.

DESIGN RULES: SELECTION OF COMPONENTS

1. Salts:

A. Effect on Loading

A "salt" is defined herein as a substance that ionizes or dissociates completely when dissolved in water to produce a solution containing ions, which ions include positive cations (but not $H^+$) and negative, non-metal or amphoteric anions (but not $OH^-$).

The variation of salt type and salt concentration provides some guidelines by which selectivity and yield of solute loading can be manipulated to load a first crosslinked polymer gel with amounts of, for example, a protein that can be pharmaceutically effective. Salts affect biologically active solute loading through hydrophobic and ionic interactions, and this implies that the change in the partition coefficient due to the presence of salts will primarily be dependent on the hydrophobicity and charge on the biologically active solute and on the interfacial potential difference between gel and loading polymers.

Johansson, G., "Partitioning of Proteins", in Partitioning in Aqueous Two-*Phase Systems*, (Walter et al., eds.), Academic Press, New York, 1985, incorporated herein by reference, has derived a nomograph depicting the virtual partition coefficients of different ions in two phase aqueous protein extraction. Sorption by one of two aqueous phases is favored by addition of salts in the increasing order lithium-ammonium-sodium=cesium-potassium for cations and in the increasing order phosphate-sulfate-acetate-fluoride-chloride-bromide-iodide-thiocyanate-perchlorate for anions.

One would not necessarily expect that these design rules for aqueous extractions would be applicable to the present methods using crosslinked polymer gel phases because proteins are generally excluded from gels. Also, a crosslinked gel-loading polymer-water phase diagram might differ from a polymer-polymer-water phase diagram. Nevertheless, these design rules may also be used as guidelines to select a salt for a particular biologically active solute loading scheme of the present invention.

Two salts can be compared by comparing the value of the virtual partition coefficients of the cation and anion ($\log K_+ - \log K_-$). For a positively charged biologically active solute (e.g., protein) a greater value of ($\log K_+ - \log K_-$) implies greater partitioning into a crosslinked gel. For a negatively charged protein, the opposite effect is observed; that is, a smaller value of ($\log K_+ - \log K_-$) implies greater partitioning into the gel polymer. The magnitude of this effect depends on the magnitude of charge on the protein; therefore, by changing the pH of the system such that the protein charge increases (i.e., made either more positive or negative), the effect of the presence of that salt can be enhanced.

The choice of a preferred cation is made on the basis that the K values obtained should be greater than one because the aim was to enhance loading of proteins into the gel rather than exclude the proteins from the gels. In order to get $K>1$, the value of ($\log K_+ - \log K_-$) for a negatively charged protein must be positive, and for a positively charged protein the value must be negative. Using this rule with, the cation for the case of negatively charged ovalbumin was $K^+$ (salts were KF, KCl, KBr, KI) and the cation for the case of positively charged ovalbumin was $Bu_4N^+$ (salts were $Bu_4NF$, $Bu_4NCl$, $Bu_4NBr$, $Bu_4NI$). The partition coefficients obtained from the above experiments for different anions are presented in Tables 1 and 2. For negatively charged ovalbumin, K increases in the order $F^- < Cl^- < Br^- < I^-$ whereas for positively charged ovalbumin, K decreases in the same order. Tables 1 and 2 show the importance of sign of the charge on the protein. For example, in the presence of $I^-$ ovalbumin favors the gel when it is negatively charged but favors the PEG when the charge on it becomes positive.

TABLE 1

Effect of Anions on Negatively Charged Protein

| Salt (0.05M) | KF | KCl | KBr | KI |
|---|---|---|---|---|
| Partition Coefficient (K) | 2.6 ± 0.4 | 5.5 ± 0.8 | 7.0 ± 1.1 | 8.7 ± 1.2 |

TABLE 2

Effect of Anions on Positively Charged Protein

| Salt (0.05M) | $Bu_4NF$ | $BU_4NCl$ | $Bu_4NBr$ | $Bu_4NI$ |
|---|---|---|---|---|
| Partition Coefficient (K) | 7.8 ± 1.3 | 3.1 ± 1.5 | 2.5 ± 0.5 | 1.7 ± 0.3 |

If two salts are present, the ratio of the salts determines the partitioning for salt concentrations in the range 0–250 mM. This property can be used to create a pH buffer which does not interfere with the partitioning. The partition-enhancing salt selected can be present in excess relative to the buffering salt, so that the partitioning is not affected by the buffering salt.

By the addition of a salt in a loading polymer, large values of K for ovalbumin have been observed. This increased partitioning in the presence of KI might be due to an unequal affinity of $K^+$ and $I^-$ ions for the dipoles present on the two polymers. This difference in affinity would result in the negatively charged ovalbumin being partitioned away from the loading polymer in order to maintain electroneutrality. Since the mechanism suggested for the effect of salts is based on the affinity of $I^-$ ions for the loading polymer, it is necessary for it to be present in solution for the salts to have the observed effect on the K value. The exact mechanisms by which salts enhance partitioning is not entirely clear.

At low salt concentrations, the buffering salt, the protein and the partition enhancing salt will contribute to the interfacial potential since they are charged molecules. This contribution will depend on the relative concentrations of these molecules. It is believed that, as the concentration of the partition enhancing salt increases, the contribution of the protein and the buffering salt to the interfacial potential will grow smaller and smaller. Therefore, the partitioning of the protein is expected to be increasingly determined by the partition of the partition enhancing salt as the concentration of the latter increases. This behavior predicts an increase in the partition coefficient as the concentration of the partition enhancing salt is increased.

B. Effect as Protectant

Salts are also selected on the basis of their protective properties. The particular salt chosen should ideally enhance loading and act as a protectant. It will be appreciated that selection of a salt will depend, in large part, on the solute to be loaded. It will be further understood that salts useful in partitioning may not be useful as protectants, so compromises must be found and experiments must be performed to test individual salts.

For example, potassium iodide (KI) is preferred to enhance loading (See above) but it is a chaotropic salt which tends to reduce hydrophobic interactions within the gel and within proteins. Chaotropic salts (e.g., guanidinium chloride) can denature proteins. Nevertheless, amylase released from HPC gels loaded using KI did maintain at least 40% of its activity (Example 5).

Salts such as ammonium sulfate ((NH4)2 $SO_4$) are known to stabilize hydrophobic interactions that hold proteins together and may be useful as a protectant salt.

POLYMERS: General Considerations

Polymers and polymer gels used in the methods of the present invention and described below may be selected from a variety of materials. In the broadest embodiment, gel and loading polymers of the invention may be selected from any one or more of a host of gels whose water soluble polymeric starting materials separate into two-phases. That is, in an aqueous system, multiples of these starting materials are fully water soluble yet are incompatible enough with each other so that they separate into two or more aqueous phases. Either one of the polymers of the phase system may be crosslinked and used as the gel. Moreover, either one of the polymers of the phase system may be used as a solution of loading polymer in the methods of the invention. Exemplary materials of this type include polyethylene oxide, polyethylene glycol, polyvinylalcohol, methylcellulose, dextran, glycerol, hydroxypropyldextran, hydroxypropylcellulose, hydroxypropyl starch, polypropylene glycol and ethylhydroxyethylcellulose, and polyvinylpyrolidone. There are additional polyphase systems of a similar nature. Exemplary materials meeting these requirements may be found in suitable reference work such as P-A. Albertsson, *Partition of Cell Particles and Macromolecules*, 3rd edition, J. Wiley and Sons, 1986, incorporated herein by reference. Polymers soluble in organic solvents may also be used.

2. Crosslinked Gel

The tern "gel" refers to a three-dimensional, crosslinked polymer network that includes a liquid solvent entrained by the interconnected matrix of polymer chains. The term "polymer network" refers to polymers crosslinked to create a three-dimensional, tangled network. The term "gel" more particularly refers to polymer networks between the liquid and solid state containing enough solvent molecules to cause macroscopic changes in the sample dimension. The term is also meant to include gels in their "dry" condition, in which all substantially all solvent that is within the gel matrix has been removed. The term "dry" is primarily an operational definition. One definition of the term is when the mass of the gel reaches a constant low value in desiccator or drying oven.

The concentration of gel may vary over a wide range. Preferred swelling degrees (Q=inverse of weight fraction) of gel range from Q=2 g/g to 100 g/g; most preferred are 4 g/g to 20 g/g.

In principle, multiple crosslinked polymers (i.e., two or more different crosslinked polymers) may be loaded using the methods of the invention. For example, a common solution of two, or more, different enzymes may be formulated and added to a mixture of corresponding (i.e., two or more) crosslinked polymer gels. By appropriate manipulation of polymers and salts as described herein, the different biologically active solutes may be partitioned into different crosslinked polymer gels with or without a third polymer.

Preferred gels are hydrogels that are well-known as being useful in controlled release applications. See, for example, Antonsen et al., *Biomat. Art. Cells & Immob. Biotech.*, 21: 1–22 (1993) and Gehrke and Lee, "Hydrogels for Drug Delivery Systems", in *Specialized Drug Delivery Systems*, p. 333 (ed. P. Tyle), M. Dekker, Inc., New York, 1990 and references cited therein.

Other preferred gels are derived from water soluble starting materials that will separate into two or more aqueous phases, as described above. Other preferred gels are three-dimensional polymer gel networks that are environmentally responsive. Responsive phenomena have been observed in permanently crosslinked polymer networks that exist as gels. As an external environmental condition (e.g., temperature; pH, ion concentration, light energy, solvent composition) is changed, the polymer network becomes increasingly compressible, and at a certain point, it becomes infinitely compressible. It was also observed that the volume of such a gel changes reversibly by a factor as large as several hundred when the gel is presented with a small change in external conditions such as solvent chemical composition or temperature. Tanaka, *Physical Review Letters*, Vol. 40, no. 12, pp. 820–823, 1978 and Tanaka et al, *Physical Review Letters*, Vol. 38, No. 14, pp 771–774, 1977; Tanaka et al *Physical Review Letters* 5, Vol 45, pg. 1636, 1980; Ilavsky, *Macromolecules*, Vol. 15, pg. 782, 1982; Hrouz et al, *Europ. Polym. J.*, Vol. 17, pg. 361, 1981; Ohmine et al, *J. Chem. Physics*, Vol. 8, pg. 6379, 1984; Tanaka et al, *Science*, Vol. 218, pg. 462, 1982 and Ilavsky et al, *Polm. Bull.* Vol. 7, pg. 107, 1982; Gehrke, "Responsive Gels: Volume Transitions II"; ed. K. Dusek, Springer-Verlag, New York, pp. 81–144 (1993); Li et al., *Ann. Rev. Mat. Sci.*, 22: 243–277 (1992); and Yu et al., *Enzyme Microb. Technol.*, 15: 354–366 (1993), all of which incorporated herein by reference. Preferred responsive gels are "reversibly responsive", i.e., when challenged with an environmental change, the environmental change affects the gel by causing the entire gel, or a component thereof, to undergo a reversible volumetric change. The gel expands from a less liquid-filled state or dry state to a more liquid-filled state; or collapses from a more liquid-filled state to a less liquid-filled state. The reversible volume change involves a shift between two equilibrium states (i.e., swollen and collapsed).

Responsive gels may be "fast response" gels. As defined herein, "fast response" means that the gel reaches 90% of its maximum volumetric swelling or 90% of its minimum volumetric collapse in a time that is at least ten times faster than a comparable non-porous gel of the same geometry when both gels are subjected to a similar change in an environmental condition. Methods of making and using fast response gels may be found in co-pending and commonly assigned PCT application, Ser. No. PCT/US94/05400, filed 13 May 1994, now U.S. Ser. No. 08/737,404 (35 U.S.C. Section 371(c) (2): "Microporous Fast Response Gels and Methods of Use"- Gehrke and Kabra), incorporated herein by reference.

Many of the fast response gels are microporous. The tenn "microporous" refers to two-phase systems of a continuous solid phase containing numerous pores filled with fluid. A "microstructure" as defined herein, refers to those structures of a gel (e.g., pores, voids, walls and the like) observable under a scanning electron, or other, microscope and ranging in size from 0.01 to about 100 microns. Gels containing pores in the size range 0.01 to about 10 microns are 'microporous'. If some of the pores are interconnected, the gel is typically called an "open-cell" gel. If all the pores in the gel are interconnected to each other, the gel is a "bicontinuous" gel. If the pores are discrete (not connected to each other), so that the internal space of each pore is independent of the other pores, the gel is a "closed-cell" gel. The present invention encompasses all these morphological forms and combinations of these forms.

The primary requirement of a responsive gel is that the entire gel, or a component, undergo a volume change. The gel as a whole must meet these requirements. Nevertheless, the gel may itself include several other components as long as at least one component(s) provides the required property. The second requirement of a gel used in the present methods is that the entire gel, or a component, be capable of sorbing a biologically active solute that is to be loaded.

For instance, the gel may be a single component such as a single polymer network which meets the requirement that the gel be responsive to an environmental change. The gel may also be a single component, such as a single polymer network which meets both loading and responsive requirements. An exemplary component is hydroxypropylcellulose.

The gel may also include two or more components, each component having a different required property. A primarily sorptive-type gel may also be made in the presence of a volume-change gel. Exemplary sorbents of this type include poly-N isopropylacrylamide [NIPA: "responsive component"]-/poly (methacrylamidopropyltrimethylammonium chloride [MAPTAC: "loading component"]. A primarily loading-type gel may also be made in the presence of a responsive gel. The gel may also be an interpenetrating polymer network (IPN). An IPN may possess only a responsive property such as poly-N isopropylacrylamide. A purely responsive IPN may thus be combined with a loading gel to meet the requirements of the present system. A purely responsive IPN may itself be combined in an IPN with a "loading" component such as poly(MAPTAC). The IPN may possess both properties, however, so that one polymer member of the IPN provides the loading property and the other polymer member provides the responsive property. Polymers of an interpenetrating gel to be loaded can include natural polymers, synthetic polymers, or crosslinked natural and synthetic polymers. Examples of synthetic polymers include poly (acrylamide), poly(acrylic acid), and the like.

As discussed previously, an important advantage of combining different polymers as part of the loaded gel (see for example, the interpenetrating polymer networks described above) is that one member(s) of the gel may be chosen for its strong ability to undergo responsive volume change and the other member(s) may be chosen for maximum loading ability. In this regard, polymers of MAPTAC are extremely useful. By itself, poly(MAPTAC) is not a gel but will absorb large amounts of water. An enhanced capacity for loading one or more biologically active solutes into a responsive gel is facilitated by poly(MAPTAC) and delivery of the solution taken up by the poly(MAPTAC) is facilitated by the responsive gel component. The poly(MAPTAC) will not be delivered along with the biologically active solute because it is too large a molecule. Examples of gels utilizing poly (MAPTAC) include, but are not limited to any of the reversibly responsive gels described previously such as poly-N isopropylacrylamide-/poly (methacrylamidopropyltrimethylammonium chloride [MAPTAC])/water; poly(acrylic acid/poly (methacrylamidopropyltrimethylammonium chloride [MAPTAC])/water; and acrylamide-sodium acrylate/ methacrylamidopropyltrimethylammoniumchloride/ water. Polymers of MAPTAC may be combined with a responsive gel, either in an interpenetrating network, by copolymerization, or by synthesizing a responsive gel in the presence of poly(MAPTAC). Other polymers like poly (MAPTAC) that are not responsive gels but are useful for their liquid loading properties include polyvinylimidazole.

The volume change of the entire gel, or a component thereof, may be either continuous or discontinuous. A "continuous" volume change is marked by a change in volume (i.e. a collapse and/or swelling) that occurs over a relatively large change in environmental condition. Moreover, there exists at least one stable volume near the transition between the swollen and collapsed states.

Responsive gels may also undergo a "discontinuous" volume change in which the transition from swollen to collapsed states, and back again, occurs over an extremely small change in environmental condition, such as less than 0.1 degree C. or 0.1 pH unit. Such reversibly responsive gels have been called discontinuous "phase-transition" gels. See Tanaka et al., U.S. Pat No. 4,732,930, or Hirotsu et al., *J. Chem. Phys.* 87: 15 Jul. 1987 describing synthetic polymeric gels that undergo phase transitions, incorporated herein by reference. There is no stable volume between the swollen and collapsed states at the phase-transition and, in theory, the expansion and/or collapse occurs over an infinitely small environmental change. A gel undergoing a continuous volume change may have a similar order of magnitude total volume change as a gel undergoing a discontinuous change.

On a molecular level, the preferred responsive gels are sensitive to small changes in a restricted repertoire of environmental "trigger" conditions consisting primarily of temperature. Trigger conditions are not so limited, however, and may also include pH, solvent concentration, and ion concentration. On a macroscopic level, any of a variety of environmental conditions may be imposed on the gel which allows the specific trigger to induce a volume change. These environmental conditions may, but not necessarily, be the same as the trigger and include, but are not limited to, a change in temperature, electric field, photon energy, pH, solvent composition, ion concentration, concentration of biomolecules, pressure, and the like.

The responsive gels of the invention may be combined with a solute that acts as a molecular "transducer", converting an environmental condition into an appropriate trigger. For example, a dye may be introduced into a temperature-triggered fast response gel. The dye is designed to absorb light of a given energy and convert the light energy into heat, thus triggering the gel to undergo a temperature induced rapid phase-transition. See also, A. Suzuki and T. Tanaka, *Nature:* 346: 6282 (1990), incorporated herein by reference.

The volumetric changes of gels described herein result from competition between intermolecular forces, usually electrostatic in nature, that act to expand the polymer network; and at least one attractive force that acts to shrink it.

Volumetric changes in aqueous responsive gels are driven primarily by four fundamental forces: ionic, hydrophobic, hydrogen bonding and van der Waals bonding interactions, either alone or in combination. Each of these interactions may be independently responsible for a volume change in preferred gels of the invention. Each of these fundamental forces is most strongly affected by a particular trigger. Changes in solvent concentration most strongly affect the van der Waals interaction; changes in temperature most strongly affect hydrophobic interactions and hydrogen bonding; and changes in pH and ion concentration most strongly affect ionic interactions.

Thus, a responsive gel whose volume change is governed by ionic interactions would include components that are weakly acidic and weakly basic, such as poly(acrylic acid)/[MAPTAC])/water; poly(acrylic acid)/poly(allylamide)/water, and the like. See, Siegel and Firestone, *Macromolecules,* 21: 3254–3259 (1988). Gels of this type are sensitive to pH and will collapse when exposed to a lower pH environment from a higher pH environment.

Responsive gels whose volume change is governed by hydrogen bonding will collapse with a decrease in temperature and are exemplified by interpenetrating polymers that comprise poly(acrylic acid) as one polymer, poly (acrylamide) as the other polymer, and water as the liquid medium. Gels whose volume change is governed by hydrophobic interactions will collapse when challenged with an increase in temperature and are exemplified by poly(N-isopropylacrylamide:NIPA). See U.S. Pat. No. 4,863,613. Gels whose volume change is governed by van der Waals interactions will behave similarly to those governed by hydrophobic interactions and are exemplified by polyacrylamide gels.

Responsive gels may be formulated in which the volume change is governed by more than one fundamental force. In particular, gels consisting of copolymers of positively and negatively charged groups meet this requirement. In these gels, polymer segments interact with each other through ionic interactions and hydrogen bonding. The combination of these forces results in the existence of several pH-driven phases. See Annaka and Tanaka, *Nature* 355: 430–432 (1992), incorporated herein by reference. An exemplary gel of this type is a copolymer of acrylic acid and methacrylamidopropyltrimethyl ammonium chloride (MAPTAC).

Equations qualitatively explain all of these aspects of volumetric changes. See T. Tanaka, D. J. Fillmore, S-T. Sun, I. Nihio, G. A. Swilslow, and A. Shar, *Phys. Rev. Letters,* 45 1636 (1980) and U.S. Pat. No. 5,100,933 (Tanaka et al.), incorporated herein by reference. See also, S.H. Gehrke, *Adv. Polymer Science* 110:81–144 (1993), for other theoretical descriptions.

Representative crosslinking agents useful for making the crosslinked gels to be loaded include N,N'-methylene-bis acrylamide, ethylene glycol dimethacrylate, glycerine triacrylate or divinylbenzene or the like. The concentration of crosslinkable solute is generally about 0.3 to 4 mole percent based upon the polymerizable solute which is the main component. The crosslinking agent effects partial crosslinking of the polymer and provides a means to control the mechanical strength of the gel, swelling degree, and intensity of phase transition trigger by changing the crosslinking density. Crosslinking of linear polymers by chemical reagents is preferred for gels made from biological polymers such as cellulose ethers. See Gehrke and Lee, supra.

Specific crosslinkers will depend upon the polymer but preferred crosslinkers for polysaccharide gels, especially cellulose ethers, are multifunctional carboxylic acids, such as adipic acid (hexanedioic acid: $HOOC(CH_2)_4COOH$), succinic acid ($HOOC(CH_2)_2COOH$), malonic acid (propanedioic acid:$CH_2(COOH)_2$, sebacic acid (decanedioic acid: $HOOC(CH_2)COOH$), glutaric acid (pentanedioic acid: $HOOC(CH_2)_3COOH$), or 1,10 decanedicarboxylic acid. Dicarboxylic hydroxyacids such as tartaric acid and malic acid as well as multifunctional carboxylic acids such as 1,2,3,4-butanetetracarboxylic acid may also be suitable. Unsaturated dibasic acids have been used to physically crosslink water soluble polymers by application of drying and/or heat. See, for example, U.S. Pat. No. 3,379,720 (Reid), incorporated herein by reference. Unfortunately, the heat required to crosslink water soluble polymers within a reasonable time of several hours is very high, ranging from 90° C. (2–3 hour gelation) to 200° C. (1–2 minute gelation). This may render the Reid method unsuitable for use with heat labile, biologically active compounds. At room temperature, the Reid methodology produced a gel in 10–30 days.

It has been discovered that a preferred method of effective crosslinking may be accomplished in 3–4 hours by using acyl halide derivatives of multifunctional carboxylic acids as the reagents added to the polymer solution. These acyl halides preferably are chloride derivatives such as adipoyl chloride, sebacoyl chloride, succinyl chloride, and the like. Acyl chloride derivatives of multifunctional carboxylic acids are very unstable in water and will react almost immediately to form the corresponding acid in solution (e.g., S. H. Pine et al., *Organic Chemistry,* supra, p. 319) and it is this acid, not its halide derivative, that becomes incorporated into the final form of the polymer network as the crosslinkage. Furthermore, because the halide derivative is so reactive with water, aqueous leaching of a polymer network with any residual halide derivative will necessarily yield the acid form of the crosslinker in the leachate, not the halide derivative.

Polymerization is initiated using a polymerization initiator, e.g., a free radical initiator such as ammonium persulfate or sodium metal bisulfite, etc., with dilution with a solvent, e.g., water, a lower alcohol, hydrocarbon, etc., or without dilution. However, neither the solvent nor the polymerization initiator are always important factors to obtain the polymerized product from the monomer mixture, and any method suitably selected from conventionally well-known gelation methods may be applied. Crosslinking can also be induced by ultraviolet or electron beam irradiation.

Crosslinked polymer networks may also be affixed onto a matrix or membrane. See Example 1. Thus, networks of the invention may be loaded and simultaneously affixed to, for example, a matrix designed for transdermal drug release. Crosslinked polymer networks may also be affixed onto a matrix or membrane after loading and fabricated into a variety of forms. For example, the materials may be used in support matrices, films or membranes, tubes, hollow fibers, solid fibers, molded objects, solid particles, capsules, micelles or liposome-like structures.

3. Loading Polymer

A. Effect of Loading

The loading polymer may be any polymer soluble in an aqueous phase. Preferably, the loading polymer is also soluble in the same solvent that is the solvent of the gel. Water is a particularly preferred solvent although the solvent may be nonaqueous.

The loading polymer may also be crosslinked, into a gel. In any case, there needs to be at least a continuous solvent phase between first and loading polymers to allow transport of at least one solute from one polymer to the other polymer that is to be loaded.

It is preferred that the gel and loading polymer be chemically and physically incompatible- e.g., the gel is more or less hydrophobic than the loading polymer so that they will not form a solid solution in each other at their respective concentrations.

There are a number of immiscible polymeric materials that are mainly water and that are close to each other on a spectrum of relative hydrophobicity-hydrophilicity. This means that systems formed by these polymers can be expected to be selective in separating substances which themselves are mainly water; that is substances that fall within the same part of the solvent spectrum. Examples of these are particles and macromolecules of biological origin. Aqueous solutions of the following polymeric materials are mutually immiscible and are ranked in rough order of increasing hydrophobicity: dextran sulfate, carboxymethyl dextran, dextran, hydroxypropyldextran, methylcellulose, hydroxypropylcellulose, polyvinylalcohol, polyethylene glycol and polypropylene glycol. Thus, any two of these may serve as the first and loading polymers. There are many published examples of such systems. See, for example, P-A. Albertsson, *Partition of Cell Particles and Macromolecules*, 3rd edition, J. Wiley and Sons, 1986. These simple design rules may be tested using methods described herein.

With properly chosen polymer systems, all manner of solutes may be loaded using the present methods. Data shown in P-A. Albertsson (supra, p. 288) for a non-crosslinked dextran-PEG system include the organic solute 1-Naphthol (MW=460,000) which, along with its isomer 2-naphthol, are precursors to such drugs as the analgesic Naproxen and the Vitamin K family of solutes, especially Vitamin $K_5$. These solutes also have food preservative properties. The partition coefficient of 1-Naphthol (1.76) is significantly different from one. Based on our work with crosslinked gels, this demonstrates the possibility of successful loading of this solute into crosslinked gels with the properly chosen systems.

B. Effect as Protectant

The loading polymer may be chosen for action as a protectant. It is known that proteins in solution may be stabilized against aggregation, precipitation, and denaturation reactions using water soluble polymers, particularly hydroxyl-containing polymers such as polysaccharides (i.e., starch and cellulose ethers), polyethylene glycol, polypropylene glycol, and copolymers thereof. See also Schein, C. H., *Bio/Technology*, 8: 308–317 (1990), incorporated herein by reference. Presence of the continuous liquid phase between the gel and loading polymer also allows some salt and loading polymer to become entrained within the gel.

One factor that determines the amount of loading polymer protectant and salt entering the gel is the degree of swelling of the gel in the loading polymer solution. For example, dextran gel beads will not swell as much in polymer solution as will a gel made of cellulose ether, e.g, hydroxypropylcellulose. The second determinant is the amount of loading polymer in solution; the more concentrated the loading polymer solution, the more it is absorbed into the gel. Thus, one may adjust the loading polymer solution concentration and the swelling degree of the gel.

1) Adjusting the amount of solute or protectant added to gel:

From a mass balance on the loading process, the total amount of solute or protectant added to loaded gel can be calculated as follows:

$$M_p/M_{gel} \, (Q-1) \, \Sigma(i=1 \rightarrow n) \, k_i x_i$$

where: $M_p$=total mass of solute or protectant in the loaded gel $M_{gel}$=mass of dry gel Q=mass swelling degree of gel in loading solution (swollen mass/$M_p$)

$k_i$=partition coefficient of species 'i'=ratio of mass fraction of 'i' gel to mass fraction of species (i) in loading solution $x_i$=mass fraction of 'i' in loading solution n=number of species For salts and inert (i.e. does not affect partitioning of bioactive solute) species, including protectants like glycerol and lactose, k will be approximately 1 (see P. A. Albertsson, Table 5.1, page 74). For the loading polymer, the value of k will be between 0 and 1. The phase diagram for the polymer-gel-water system will determine the value of k for the loading polymer, as well as the swelling degree of the gel (Q). The phase diagrams for 24 different systems is given in Chapter 12 in Albertsson, along with detailed directions for determining the phase diagram of any given system. For crosslinked gel-soluble polymer systems, determining the phase diagram is much easier than for the soluble polymer-soluble polymer systems. Polymer concentration assays can be avoided since there can be no gel polymer that is dissolved in the soluble polymer solution. The gel of known mass and water content is equilibrated with a comparable volume of loading polymer solutions of various compositions. The gel is removed and weighed to determine total mass, then dried to determine water and soluble polymer content. Similarly, the polymer solution is weighed, then dried to determine water content and thus polymer content. Other techniques are also possible; for example a gel of known dry mass can be swollen in excess polymer solution whose composition can be assumed constant, and then removed, weighed and dried to determine water and soluble polymer content. If salt is present in the systems, however, an assay for the salt or the solution polymer will also be required.

Using an approximate phase diagram giving estimates of Q and $k_i$, one can determine the concentrations of protectants needed to obtain the desired objective, while using salt and polymer selection rules to simultaneously obtain efficient protein loading.

There may well be other reasons for desiring the loading of adjunct materials into the gel along with the active solute. For example, a surfactant may help solubilize a poorly soluble drug, salts may alter the swelling rate of the gel and thus the release rate of the drug, and so on. The use of such additives in formulating a drug release system is well-known in pharmacy and other fields involving delivery of solutes to target environments.

2) Protocol for determining ability of protectants to retain or reduce the loss of bioactivity of a loaded solute a) Determine the appropriate assay for solute bioactivity.

b) Identify the likely denaturing event from which the solute is to be protected; e.g. temperature or pH, precipitation, agglomeration.

c) Prepare several solutions: a control of the active species in appropriate solution (typically one equal to the release solution), the same solution with different levels of protectants dissolved in it according to rules described herein.

d) Determine the bioactivity of the freshly prepared solute solution.

e) Set aside two aliquots of the control; then load the gel by immersion in the various test solutions, including an aliquot of the control solution.

f) Process the loaded gels as appropriate; e.g., dry under vacuum, heated, store wet, etc. and treat a control aliquot similarly.

g) Expose the loaded gels and treated control to the potential denaturing conditions for an appropriate time if different from processing in f).

h) Release the solute from the gels into an appropriate solution matching the control solution.

i) Determine the bioactivity of the released solute and the total amount of solute released (e.g. UV absorbance at 280 nm for protein).

j) From the ratio of: (activity units)/(g) of the released solute to the (activity units/(g) of the fresh control, the percentage of retention of activity can be found. Since activity can degrade simply to time, etc., the controls carried along through the test process can be used to identify reduction of activity loss by protectants relative to unstabilized solute. From the results, the optimal loading conditions for maximum activity retention can be determined.

4. Biologically Active Solutes

Any material that is soluble may in principle be loaded with the present method. The most preferred solutes are biologically active solutes and are any substance, or mixture of substances, that are susceptible to being denatured or otherwise inactivated and that has biological and/or chemical activity when active. The term includes, but is not limited to, enzymes (either isolated or in whole cells), pesticides, insecticides and the like, proteins, polypeptides, polynucleotides, nucleoproteins, polysaccharides, glycoproteins, steroids, lipoproteins, and synthetic and biologically engineered analogs thereof, either alone or in combination. The term "protein" is art-recognized and for purposes of this invention also encompasses peptides. The proteins or peptides may be any biologically active protein or peptide, naturally occurring or synthetic. Examples of proteins include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating honnone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules. Other examples of biologically active solutes that might be utilized in a controlled delivery application of the invention include literally any hydrophilic or hydrophobic biologically active solute. Furthermore, biologically active solutes that are liquids or are not liquid at body temperature can be incorporated into gels. Moreover, peptides and proteins which may normally be lysed by tissue-activated enzymes such as peptidases, can be passively protected in gels as well. The term, "biologically active solute" includes pharmacologically active substances that produce a local or systemic effect in animals. The term thus means any substance intended for use in the diagnosis, cure, mitigation, treatment or prevention of disease or in the enhancement of desirable physical or mental development and conditions in an animal. The term "animal" used herein is taken to mean mammals such as primates, including humans, sheep, horses, cattle, pigs, dogs, cats, rats and mice. The method is not restricted to mammals since the methods and compositions described herein may be used in literally for living entity including plants, insects, fish and the like.

Using the methods described herein, one of ordinary skill in the art may readily determine if a particular biologically active solute has the ability to be loaded into a gel and, once loaded and released, whether it retains its biological activity. The kind and manner of testing needed to determine whether a solute released from a loaded gel is biologically active will necessarily vary with the solute and is well within the level of ordinary skill in the art.

Classes of biologically active solutes which can be loaded into crosslinked gels using the methods of this invention include, but are not limited to, anti-AIDS substances, anti-cancer substances, antibiotics, anti-viral substances, enzyme inhibitors, neurotoxins, opioids, hypnotics, antihistamines, immunosuppresents (e.g., cyclosporin), tranquilizers, anti-convulsants, muscle relaxants and anti-Parkinson substances, anti-spasmodics and muscle contractants, miotics and anti-cholinergics, iminunosuppressants (e.g. cyclosporine) anti-glaucoma solutes, anti-parasite and/or anti-protozoal solutes, anti -hypertensives, analgesics, anti-pyretics and anti-inflammatory agents (such as SNAID's), local anesthetics, ophthalmics, prostaglandins, anti-depressants, anti-psychotic substances, anti-emetics, imaging agents, specific targeting agents, neurotransmitters, proteins and cell response modifiers.

A more complete listing of classes of solutes suitable for loading into polymers using the present methods may be found in the *Pharmazeutische Wirkstoffe*, ed. A. Von Kleemann and J. Engel, Georg Thieme Verlag, Stuttgart/New York, 1987, incorporated herein by reference.

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir (acyclovir), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone caproate, medroxyprogesterone acetate, megestrol acetate, diethylstilbestrol, ethinyl estradiol, tamoxifen, testosterone propionate, fluoxymesterone, vinblastine, vincristine, vindesine, etoposide, teniposide, dactinomycin, daunorubicin, doxorubicin, bieomycin, plicamycin, mitomycin, hydroxyurea, procarbazine, mitotane, aminoglutethimide, mechlorethamine, cyclophosphamide, melphalan, uracil mustard, chlorambucil, busulfan, carmustine, lomusline, semustine (methyl-CCNU), streptuzocin, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vanomycin, bacitracin, kanamycin, neomycin, gentamycin, erythromicin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Anti-viral agents are substances capable of destroying or suppressing the replication of viruses. Examples of anti-viral agents include a-methyl-P-adamantane methylamine), 9-[2-hydroxy-ethoxy]methylguanine, adamantanamine, 5-iodo-2'-deoxyuridine, trifluorothymidine, intereron, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCL, tacrine,1-hydroxy maleate, iodotubercidin, p-bromotetramisole, 10-(a-diethylaminopropionyl)- phenothiazine hydrochloride, calmidazolium chloride, hemicholinium-3, 3,5-dinitrocatechol, diacylglycerol kinase inhibitor I, diacylglycerol kinase inhibitor II, 3-phenylpropargylaminie, $N^6$-monomethyl-L-arginine acetate, carbidopa, 3-hydroxybenzylhydrazine HCl, hydralazine HCl, clorgyline HCl, deprenyl HCl,L(-), deprenyl HCl,D(+), hydroxylamine HCl, iproniazid phosphate, 6-MeOtetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2, 3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+), p-aminoglutethimide tartrate,S(-), 3-iodotyrosine, alpha-methyltyrosine,L-, alpha-methyltyrosine,D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2, 3-dihydropyridinium perchlorate, N-methyl-4-phenyl-1,2,5,6-tetrahydropyridine HCl, 1-methyl-4-phenylpyridinium iodide.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include norbinaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, dimethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, antaoniline and the like.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, and ethosuximide.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are solutes which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma solutes include betaxalol, pilocarpine, timolol, and combinations of tinolol and its salts with pilocarpine.

Anti-parasitic, -protozoal and -fungals include ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects. Examples of such agents include E2 and E1.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a biologically active solute.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, inacrophage colony stimulating factor and granulocyte-macrophage colony stimulating factor; tumor necrosis factors, including alpha and beta; transfonning growth factors (beta), including beta-1, beta-2, beta-3, inhibin, and activin.

The present invention will now be illustrated by the following, non-limiting examples.

EXAMPLE 1

Development of Gel Sorbent in a Support Matrix

This Example illustrates creation of a gel directly in a supporting matrix of porous cellulose fiber.

The gel is a polyacrylamide and the support matrix is either filter paper or Kimwipe (trademark of Kimberly-Clark). The pregel solution is made by dissolving 5 g acrylamide (Aldrich Chem. Co., (0.133 g methylenebisacrylamide (BIS) (Aldrich Chem. Co.), and 240 microliters tetramethylethylenediamine (TEMED, Aldrich) in 100 ml deionized water. After the solution is degassed under vacuum for about 15 minutes to removed dissolved oxygen in the solution, about 40 mg ammonium persulfate (APS, Aldrich) is added as initiator. As soon as the APS is added, a piece of Kimwipe is immersed in the solution and taken out to be placed between two flat glass plates. The gelation reaction is allowed to continue for about 12 hours. The same procedure is repeated using a piece of filter paper.

After gelation, the glass plates are separated and the gel membrane peeled off. This results in a clear gel with the thickness and strength of the original porous cellulose substrate.

EXAMPLE 2

Loading, Release and Protection of Amylase

A series of experiments was performed to test loading and release of amylase from dextran gels. Dextran gel cylinders were synthesized in a laboratory. These materials had a surface area/volume ratio much smaller than dextran gel beads. It was desired to rule out the possibility that surface adsorption effects are significant in gel loading using the methods of the invention. The sample dimensions used are suitable for a controlled delivery application.

Dextran Gel Synthesis and Characterization

The dextran gels were synthesized by dissolving the dextran polymer in aqueous sodium hydroxide solution. Approximately 1 g of dextran (mol. wt. 39,100) was dissolved in 10 ml of aqueous sodium hydroxide (0.02M). The first dextran polymer and sodium hydroxide solution was stirred until the polymer was wetted. The solution was then covered with Parafilm and allowed to completely hydrate over the course of 24 hours.

Divinylsulfone (DVS) was added by micropipette and the solution was stirred with a spatula. The solution was kept in an ice bath so as to slow the reaction time. The solution was then placed in clean glass tubing molds (2 mm diameter× 152.4 mm length) by syringe. The amount of crosslinker used is reported as gram reagent per grain of dry polymer. The DVS dosage for the dextran gels was 0.12 g/g dextran. The molds were covered with Parafilm and allowed to completely react over a 24 hour period.

The gels were then removed from their molds by injecting some deionized water into the gel mold using a syringe. The gels were then placed in deionized water to leach out any unreacted reagents remaining in the gel. The water was changed periodically over a three-four day period. Once a constant weight was obtained, the gels were assumed to be free of any unreacted reagents. The gels were then cut into 15 mm×1.75 mm diameter pieces and placed into a desiccator jar to dry for 24–48 hours. The dry gel had dimensions of 7.15 mm×0.75 mm diameter.

The gels were characterized in terms of their degree of swelling. Since the degree of swelling is defined as the ratio of swollen gel mass to that of dry polymer mass, the dry polymer mass was assumed to be 10% (mass to volume).

Equilibrium Loading

The loading of a biologically active solute into the hydrogel was performed by equilibrating the hydrogel in a biologically active solute-containing solution. All experiments were run in triplicates. For dry gel experiments, dry gels were equilibrated with 3 ml PEG (mol. wt. 10,000, 12 wt%)/salt (0.22M KBr, KCl, or KI) or protein (about 1.00 mg amylase/ml, PEG/salt) solution. Three ml of PEG/salt or protein/PEG/salt solution were added to 3.7 ml glass vials into which the gels were placed. Three gels (12.5 mg total weight) were placed in each vial. The gel mass/solution mass ratio during loading of the dry gels was $2.55\times10^{-3}\pm0.27\times10^{-3}$ so that the solution is in excess relative to the gel concentration. This mimics the conditions in a standard in vitro release test. The gels and vials were stored at room temperature in a desiccator jar and the weights of the gels were recorded vs. time.

A blot and dry method was used to weigh the gels. Once a constant weight was obtained, the gels were assumed to be equilibrated. Once equilibrated with the appropriate solutions, the gels were removed from solution and placed in a desiccator jar to dry. The swollen dimensions of the gels are 1.17 mm diameter×10.2 mm length. The dry gels were left in the desiccator jar until they ready to be used.

The dry gels were equilibrated with solution prior to the protein equilibration. This is an optional step. To begin, the dry gels were equilibrated with 3 ml PEG (mol. wt. 10,000, 12 wt%)/salt (0.22M KBr, KCl, or KI). Three gels were placed in each vial. The gels remained in solution until a constant weight was obtained. This process took approximately 60 hours. At that time, the gels were removed from the PEG/salt solution and placed in the protein loading solution. The swollen weight of the gels upon removal from the PEG/salt solution was about 40 mg total weight.

To load the swollen gels, the swollen PEG/salt loaded gels were placed in a protein solution. The gel-solution ratio during the protein loading of the swollen gels was $8.28\times10^{-3}\pm0.35\times10^{-3}$. The swollen gels were equilibrated with 3 ml of protein (about 0.20 mg ovalbumin/ml; about 1.00 mg amylase/ml) solution plus PEG/salt solution. During the swollen loading experiment, there was no salt variance, i.e., PEG/KI loaded gels were placed in protein/PEG/KI solutions. The gels remained in solution until a constant weight was obtained by the blot and weigh method.

The protein content could be estimated by mass balances in the case of the dry gel experiments. The amount of protein absorbed by the gel was assumed to be the difference between the dry loaded gel weight and the dry loaded weight of a gel treated identically but for the absence of protein in the loading solution. As for the swollen gel experiments, protein content was determined by spectrophotometric data which revealed the total amount of protein released in the sample.

Release Kinetics

The protein released from the dry gels was estimated by mass balances and calculated from spectrophotometric data while that for the swollen gels was only by spectrophotometric data. A phosphate buffer solution (0.01M with measured pH of 6.79) was used to leach out the protein from the protein loaded dry gels. Three mL of phosphate buffer was placed in each vial. At specified time intervals, a defined volume of released solution was removed from the original solution. This volume of released sample was placed in a vial. Immediately after the removal of the released sample, an identical volume of fresh phosphate buffer was placed back into the original releasing media. Therefore, a constant volume was maintained for the release experiments. This process was continued for approximately 10 hours of regulated sampling, with samples taken every 20 minutes for the first 2 hours and then every hour. This particular technique was used to determine total amount of released biologically active solute data.

For other gels, experiments were done to calculate the diffusion coefficient for the biologically active solute within the gel. A constant volume was maintained for the release experiment, as above. A constant volume of solution was removed from the release vial and placed in another vial. The gels were replenished with an exact volume of fresh phosphate buffer. This process was continued for approximately 5 hours with samples taken every 5 minutes for the first half hour, ever ten minutes the second half hour, every half hour for the second hour and then on the third and fifth hour. The released solution samples were analyzed using a spectrophotometer. The absorbencies measured were converted into amount of protein released using calibration curves.

EXPERIMENT 1

Loading and Release of Amylase Using Buffer without any Protectant or Loading Polymer Amylase was loaded into a dextran gel. The buffer contained 0.01M Phosphate Buffer 0.005 mol $KH_2PO_4$—(cat. # P-285, Fisher Scientific), 0.005 mol $Na_2HPO_4$, (cat. # SX0720-1, MCB Mfg. Chemists); pH 6.68 at 25 degrees C. The biologically active solute was α-amylase, *B. subtilis*, having a molecular weight of 48,450, cat. # 171568, Calbiochem., 0.9866 mg amylase/ml solution. The gel was made from dextran (molecular weight 40,800, cat. # D-4133, Sigma Chemical Co.) in a 10% solution and crosslinked with 0.14 g divinyl sulfone ( DVS-cat. # V370-0, Aldrich Chemical Co.) /g dry dextran.

Loaded gels were dried in a desiccator jar at room temperature. Release experiments were run as described above using a 3 mL volume that was replenished with calcium chloride/phosphate buffer (0.005 mol $KH_2PO_4$, 0.005 mol $Na_2HPO_4$ and 0.01 mM $CaCl_2$); pH 6.76 at 25 degrees C.). Absorbance was measured at 280 nm on a Shimadzu spectrophotometer.

EXPERIMENT 2

Loading and Release of Amylase Using Buffer with Added KCl

Amylase was loaded into a dextran gel as in Experiment 1 except that the salt was potassium chloride (0.22M) and the amylase was 1.0666 mg/ml solution. Absorbance was measured at 280 nm on a Shimadzu spectrophotometer.

EXPERIMENT 3

Loading and Release of Amylase Using Buffer with Added PEG and KCl

Amylase was loaded into a dextran gel as described except that the loading polymer was polyethylene glycol (mol. wt. 10,000, cat. # 30902-8, Aldrich Chemical Co.), 12 wt % and the amylase was 1.0133 mg/ml solution. Absorbance was measured at 280 nm on a Shimadzu spectrophotometer.

EXPERIMENT 4

Retention of Activity of Amylase Loaded Using Buffer with Added PEG and KCl

Amylase was loaded into a dextran gel as described except that the loaded gel was dried in an oven at 60 degrees C. for 48 hours then placed in a desiccator jar at room temperature. The amylase was 1.0067 mg/ml solution. Absorbencies were measured at 280 nm on a Shimadzu spectrophotometer. Release from the gel was performed as described. Protein content of a dry gel was determined by mass balance. The amount of protein absorbed by the gel was assumed to be the difference between the dry loaded gel weight and the initial dry gel weight.

For all release experiments, the amylase released was assayed for bioactivity using a Sigma Chemical assay kit #577 [based on colorimetric measurement of the enzymatic release of p-nitrophenol from the substrate 4.6-ethylidene ($G_7$)-p-nitrophenyl ($G_1$)-α, D-maltoheptaside].

RESULTS

Table 3 lists the results of the amylase release studies. The following points are noteworthy:

1. Loading from buffer alone resulted in a modest protein loading (" % Mass Loading"=2.6% ) due to the high swelling of the gel. Since no other solutes are added besides buffer, the mass increase after loading matches the value of protein released as measured by UV spectrophotometry ); i.e. protectant loading is zero within experimental error.

2. Adding the KCl to the buffer/protein solution without also adding PEG causes a significant increase in the mass loading of the gel (18.6%), but this is due simply to non-selective sorption of the salt due to the high gel swelling alone, so that the gel retains the salt upon drying. Little protein is absorbed or released from this gel. If high amounts of a particular protectant are desired in the gel, the gel should be made to swell in this solution.

3. Loading from KCl and PEG solution leads to a significant mass increase —9.2±2.9%, about half of this being protein, the other half protectant—i.e., salt and PEG. The gel swells much less in PEG solution that in KCl or buffer, so the absolute amount of protectant absorbed is reduced. However, the system is much more selective for protein; the estimated amylase partition coefficient is 16.4±0.9.

4. For amylase released from buffer-loaded gel, the retention of activity was 72±17% of the initial amylase solution. Activity retention was poorer from the KCl—loaded gel ( 48±6%). Possibly the extreme salt to protein ratio was too great to protect the amylase and the protectants may possibly have dehydrated and denatured the amylase somewhat. The best activity retention was seen with the loading system PEG-KC1. With this system, retention was virtually 100%, independent of release time interval, and significantly better than the other systems.

order of magnitude expected for a large molecule like amylase in a gel.

TABLE 3

Release Studies of Amylase from Dextran Gels

|  | Buffer avg of 3 trials | std. dev. | Buffer + KCl avg of 3 trials | std. dev. | Buffer + KCl + PEG avg of 3 trials | std. dev. |
|---|---|---|---|---|---|---|
| Dry Gel Wt., mg | 13.0 | 0.3 | 13.1 | 0.3 | 13.0 | 0.4 |
| Wet Loaded Gel Wt., mg | 134.3 | 2.7 | 135.5 | 5.2 | 45.3 | 1.0 |
| Swelling degree, mg wet/mg dry | 10.3 | 0.1 | 10.4 | 0.2 | 3.5 | 0.1 |
| Dry Loaded Gel Wt., mg | 13.3 | 0.1 | 15.5 | 0.7 | 14.2 | 0.4 |
| % Mass Loading | 2.6% | 2.0% | 18.6% | 2.7% | 9.2% | 2.9% |
| wet Released Wt., mg | 130.8 | 5.7 | 122.9 | 15.0 | 127.5 | 8.9 |
| Protein Released, mg based on 280 nm absorbance | 0.345 | 0.087 | 0.113 | 0.013 | 0.753 | 0.035 |
| "Protectant" Mass, mg (mg loading - mg protein released) | −0.012 | 0.274 | 2.320 | 0.414 | 0.447 | 0.328 |
| % Protein Loading (mg/mg, dry loaded gel) | 2.6% | 0.6% | 0.7% | 0.1% | 5.3% | 0.3% |
| % "Protectant" Loading (mg/mg dry loaded gel) | −0.1% | 0.2% | 14.9% | 2.0% | 3.1% | 2.3% |
| Protein Partition Coef. | 2.60 | 0.66 | 0.79 | 0.11 | 16.42 | 0.89 |
| Active Units Released |  |  |  |  |  |  |
| between 0–5 min. |  |  | 0.21 | 0.03 | 1.68 | 0.21 |
| between 5–10 min. |  |  |  |  | 0.79 | 0.19 |
| between 40–50 min. |  |  |  |  | 0.93 | 0.11 |
| between 270–390 min. | 0.29 | 0.07 |  |  | 1.08 | 0.07 |
| between 390–540 min. |  |  |  |  |  |  |
| Retention of Activity |  |  |  |  |  |  |
| between 0–5 min. |  |  | 48% | 6% | 115% | 14% |
| between 5–10 min. |  |  |  |  | 116% | 27% |
| between 40–50 min. |  |  |  |  | 102% | 12% |
| between 270–390 min. | 72% | 17% |  |  | 101% | 7% |
| between 390–540 min. |  |  |  |  |  |  |

Table 4 shows results of the heat inactivation experiments. Inital A and Final A are absorbance data used to calculate activity from the assay kit. The PEG-KCl loaded gel is seen to stabilize the amylase against heat denaturation, as the gels could be dried in the oven at 60° C. and stored there for at least 2 days and still retain about 80% of its activity. In contrast, an amylase solution was completely denatured after 20 hr at this temperature (data not shown).

EXAMPLE 3

Loading and Release of Ovalbumin

About 23 mg ovalbumin/ml PEG/salt solution were loaded into dextran gels using the procedures outlined in Example 2, except that in some experiments, the gels were not dried.

TABLE 4

Amylase Release from Amylase PEG-KC1 Loaded Dextran Gel, dried by heating for 48 h at 60° C.; amylase release into buffer.

| Vial | rel. time (min) | initial A | final A | Activity (U/L) | Units | Conc. (mg/ml) | Mass (mg) | U/mg | % Activity Ret'd |
|---|---|---|---|---|---|---|---|---|---|
| 4E | 5 | 0.039 | 0.122 | 290.71 | 0.87 | 1.68 E-02 | 50.400 | 17.3 | 86.1% |
| 7E | 5 | 0.035 | 0.123 | 308.22 | 0.92 | 2.09 E-02 | 62.700 | 14.7 | 73.4% |
| 4.1 | 5 | 0.035 | 0.107 | 252.18 | 0.76 | 1.54 E-02 | 46.200 | 16.4 | 81.5% |
|  |  |  |  |  |  |  |  | avg: | 80.3% |
|  |  |  |  |  |  |  |  | std. dev.: | 6.4% |

FIG. 1 is representative of the amylase release curves based on UV measurement of total protein released. The curve shows good trial-to-trial consistency of release. It is a classic diffusion controlled release curve that is linear when release is plotted here in normalized fashion against the square root of time. There is a slight lag time initially due to the fact that the gel must absorb some water first before the protein can be released. The diffusion coefficient of the protein release is of the order $5 \times 10^{-8}$ cm$^2$/sec, which is the The partition coefficient, K, for ovalbumin is equal to the concentration of protein in the gel divided by the concentration of protein in solution. In this particular study, the concentration of protein in the gel reflects the amount of solute which has been released; therefore, all protein released into the buffer solution is assumed to be the amount absorbed by the gel. This allowed for an estimate of the partition coefficients. Partition coefficients ranged from 3.4 to 6.9, depending on salt and protein concentration.

From ovalbumin calibration curves, the absorbance vs. time data was converted into concentration vs. time data. The amount of protein released in 3 ml buffer was calculated as the total volume of buffer solutions (3 mL) multiplied by the concentration at a particular instant. Finally, the total amount of protein released is determined as a function of time. The total amount of protein released is the amount of protein released at a specific time interval ($t_n$) plus the sum of the amount of protein removed at all previous time intervals (not including $t_n$). Release kinetic data (not shown) revealed diffusion-controlled release kinetics, similar to the amylase curve in FIG. 1.

The weight percent of loaded protein was calculated using the spectrophotometric data. It is the total amount of protein released from the gel divided by the weight of the dry gel or the swollen gel. The average estimated percent loadings ranged from 0.31±0.01 mg protein/mg initial dry gel for KCl loaded gels to 0.38±0.01 mg protein/mg initial dry gel for KBr loaded gels. Loadings of the protectant salt and polymer ranged from about 0.02 to 0.10 mg protectant/mg initial dry gel. The swollen gels show a slightly higher weight percentage than the dry gels.

Mass balance calculations were also performed assuming that sorption of salt equals the PEG and salt uptake into the gel. This value was substracted from the weight of the protein, PEG and salt-loaded gel. Loading calculated using mass balance ranged from 0.35 to 0.43 mg protein/mg dry gel, in reasonable agreement with the spectrophotometric data.

EXAMPLE 4

Loading and Release of Ovalbumin from HPC Gels

A series of experiments was performed to test loading and release of ovalbumin from a responsive hydroxypropylcellulose gel.

A. Synthesis of pH-Responsive HPC Disks

The crosslinking reaction of HPC with adipoyl chloride was performed as follows: Exactly 50 ml of N-methyl pyrolidone (Fisher Scientific, Catalog No. 03688-4) was added to 5 grams of hydroxypropylcellulose (Aqualon, Klucel 99-EF NF). The two materials were mixed on a magnetic stirrer for about 2 hours, while covered, to achieve a clear and colorless solution. This solution was then placed in a refrigerator for about 1 hour in order to achieve a solution temperature of 4°–8° C. To this solution, while stirring, I mL of cold (2°–8° C.) adipoyl chloride (Aldrich, Cat. No. 16,521-2) was added, and the resulting solution allowed to stir for 1 minute. After the addition of adipoyl chloride, the mixture was poured into molds consisting of two glass plates separated by a 2-mm thick buna rubber spacer. The crosslinking was allowed to proceed for 24 hr at room temperature. After the crosslinking reaction, the gel sheet was cut into disks 12.5 mm diameter with a cork borer, and washed in a vessel containing an excess of deionized water (Millipore Alpha-Q). After about 8 hours the water is decanted off, and the vessel filled with methanol (ACS grade). The gel is allowed to sit in methanol solution for 5 hours. This is followed by three more, 5 hour methanol washes.

The HPC gel made in this way was pH responsive. This was tested by making an HPC cylinder with the same reagents but using a pipette as a mold. The pipette was mounted in an airspace of a small, clear capsule (about 5 cm×4 cm×2 cm). Temperature of the capsule was regulated by equilibrating it with well stirred, temperature controlled water solution. A differential thermocouple arrangement permitted the monitoring of temperature differences between water and air within the capsule to about 0.005 deg. C. Water temperature within the capsule was measured to about 0.1 deg. C. with a digital thermocouple (mfg. by Cole-Parmer Scanning Thermocouple Thermometer #92800-00). Two sealed containers were partially filled with pure, degassed distilled water. One container also contained a port to allow addition of acid; the second container contains a port for addition of base. Use of a single container to generate a wide range of pH values from acid to base would lead to formation of neutral salt, which might have induced a volume change in the gel. A series of pH solutions was made, as described below, and then pumped through the bore of the tube at a flow rate of 3 ml/min. The diameter of the gel cylinder was observed at each pH and recorded through the optically clear walls of the capsule using a 10× microscope. Volumetric ratio changes of the gel with pH were determined by cubing the ratio of the gel string diameter to pipette bore. The pH solution was changed every 0.5 pH units and maintained to let the gel reach equilibrium. Then, the volume of the gel was measured. Water temperatures differed by no more than 0.1 degree C. during the experiments and were maintained at 25 degrees C. Low pH values were obtained by adding concentrated hydrochloric acid in increasing amounts to the pure, distilled water in one container. Above the pH value for pure, distilled water lacking any acid addition (pH 6), the second container was employed and sodium hydroxide (1N) was added. The pH was controlled by flowing dry nitrogen gas slowly through the headspace of each container to maintain a positive pressure and prevent entrance of ambient air into the container. pH was recorded continuously in each container by an Orion combination pH electrode (#91-56) immersed in the solution connected to an Orion #520 pH meter. This gel exhibited a volumetric dependency on pH.

A general method of gel disc preparation has been described by Antonsen, et al. (K P Antonsen, et al., *Biomat, Art. Cells & Immob. Biotech,* 21(1), 1–22 (1993)).

B. Loadings of Ovalbumin

The materials used were:

Buffer: $KH_2PO_4/Na_2PO_4$ (Buffer Salt, pH 6.86, Fisher Scientific, #B78).

Protein: Ovalbumin Grade II (A5253) Sigma Chemical (St. Louis, Miss.); 2.3 mg protein/mL soln.

Second Polymer: Polyvinyl Alcohol 87–89% hydrolyzed, Aldrich Chemical (36, 317-0) 10% by weight in loading soln.

Salt: No salt used The loading of ovalbumin into the gel was performed by equilibrating the gel in an ovalbumin solution. Ten ml of PVA or ovalbumin/PVA solution were added to 2.0 ml glass vials into which the HPC gels were placed. One gel (3.5 mg total weight) were placed in each vial. The gels and vials were stored at room temperature in a desiccator jar and the weights of the gels were recorded vs. time. A blot and dry method was used to weigh the gels. Once a constant weight was obtained, the gels were assumed to be equilibrated. Once equilibrated with the appropriate solutions, the gels were removed from solution and placed in a desiccator jar to dry.

The ovalbumin content was determined solely by mass balances. The amount of ovalbumin absorbed by the gel was assumed to be the difference between the dry loaded gel weight and the initial dry gel weight for gels loaded with, and without, PVA.

From mass balance calculations, the average percentage loading (n=3) of HPC gels with PVA, ovalbumin and buffer was 135.5% ±8.1%. The average percentage loading (n=3) of HPC gels without PVA was 38.3% ±21.5%. The estimated ovalbumin loaded is the difference between these numbers, or about 97%. Thus, almost all of the ovalbumin was loaded into the HPC gels.

Release Kinetics

The ovalbumin released from the dry gels was determined as follows: The phosphate buffer solution was used to leach out the ovalbumin from the ovalbumin-loaded gels. Three ml of phosphate buffer was placed in glass vials. At specified time intervals, a defined volume of released solution was removed from the original solution. This volume of released sample was placed in a vial. Immediately after the removal of the released sample, an identical volume of fresh phosphate buffer was placed back into the original releasing media. Therefore, a constant volume was maintained for the release experiments. This process was continued for approximately 10 hours of regulated sampling, with samples taken every 20 minutes for the first 2 hours and then every hour. This particular technique allowed for assay of total amount of released ovalbumin.

Release of ovalbumin into phosphate buffer after 24 hr was equal to 8 mg, or 23 mg/mg dry weight gel.

EXAMPLE 5

Loading and Release of Amylase from HPC Gels

The loading of α-amylase into HPC gels was performed by the same method as for ovalbumin with the following reagents.

Buffer: $KH_2PO_4/Na_2PO_4$ (Buffer Salt, pH 6.86, Fisher Scientific, #B78).

Protein: α-amylase, bacillus subtilis; mol. wt. 48,450; Calbiochem 1,000,000 units (cat #171568); 1.37 mg amylase/mL, soln.

Loading Polymer: PEG-PPG Copolymer (50/50 by weight), PLURONIC® P105, mol. wt. approx. 6,500 (BASF Performance Chemicals), 10% by weight in loading solution.

Salt: KI, ACS grade (Fisher Scientific, Cat. #P410), 0.22M.

Gels were loaded as above and then dried in desiccator at room temperature.

The release of α-amylase from HPC gels was performed by placing the dried gels in 3 mL release buffer (release buffer=0.005M $KH_2PO_4$, 0.005M $Na_2PO_4$, 0.01M $CaCl_2$) in glass vials. These vials were hand shaken initially and at various intervals during release. At timed intervals, the liquid was carefully removed from the vials and replaced with fresh buffer.

A bioactivity assay was performed using a Sigma Chemical Assay Kit #577 (based upon colorimetric measurement of the enzymatic release of p-nitrophenol from the substrate 4,6 ethylidene $(G_1)$-p-nitrophenol $(G_1)$-α, D-maltoheptaside). The concentration assay for amylase is run using a UV/VIS spectrophotometer (Shimadzu 160U) at 280 nm. The bioactivity of the α-amylase was determined at selected intervals, and the concentration of the enzyme was assayed at all intervals.

Characteristic release curves for α-amylase from the HPC gel (not shown) revealed a diffusion-controlled release pattern with release as a function of the square root of time showing a linear relationship. The released enzyme maintained at least 40% of its original bioactivity over the release interval of 24 hours.

B. Utilities/Formulations:

Polymer networks of the invention loaded with a solute (i.e., a biologically active solute) and its appropriate protectants find use as delivery vehicles in agricultural, pharmaceutical or veterinary applications. The techniques described herein may be used to load oral dosage forms (i.e., tablets), injectable gel microspheres, reservoirs of transdermal devices and the like. In one embodiment of the present drug delivery method, a responsive gel is loaded with a biologically active solute and a protectant moiety at one temperature using the method of the invention and undergoes a volumetric change (i.e., expansion or collapse) to deliver the entrained biologically active solute at another temperature. Delivery of the solute may be modulated by a temperature higher than the temperature of the gel in its loading mode (See Gutowska et al., *J. Controlled Release*, 22: 95–104 (1992)—using NIPA to release heparin at high temperature). In another embodiment, a gel that is not a responsive gel is loaded using the present methods and simple passive diffusion of solute out of the gel provides the necessary release.

In a further drug delivery embodiment, a loaded responsive gel expands to release a drug during exposure to pH conditions that are different than the pH conditions to which it is exposed in the loading mode. Without wishing to be bound by any theory, a loaded cellulose ether gel such as HPC with an LCST near body temperature (e.g., 42° C.) should have its LCST shifted to a lower temperature at lower pH. This is because very few —COOH and/or —OH groups are ionized at low pH and the gel would tend to have a reduced hydrophilicity. At higher pH, many —COOH and/or —OH groups will be ionized and the LCST is shifted to a higher temperature due to increased hydrophilicity. Around body temperature, the gel is therefore very sensitive to pH change and would be collapsed at low pH (i.e., that of the stomach, where the drug would be retained within the polymer network) and expanded at higher pH (i.e., that of the intestine, where the polymer network would expand and release the drug). A reversible gel may be made from starting materials (i.e., cellulose ethers of various configurations) that vary in their hydrophobic/hydrophilic nature when ionized, so that the methods described herein may be used to make a loaded, reversibly responsive, pH-sensitive gel with an LCST designed to match the application. The LCST of cellulose ethers is well known and can be easily determined and verified. Exemplary LCST's (degrees C.) are 49° (MEC); 42°–46° (HPC); 59° (methyl(hydroxypropyl) cellulose); 60° methyl(hydroxyethyl)cellulose; and 55°–70° (ethyl(hydroxyethyl)cellulose).

Loaded polymer networks of the invention may be used to coat medical devices to improve the surface properties and to incorporate a desirable medicament into the coating.

Loaded polymer networks of the present invention also find use in the agricultural release of pest control substances (i.e., solutes) such as pesticides, pheromones, fungicides and herbicides, including viruses and bacteria. Various controlled release devices or encapsulation products may be used with the loaded gels of the invention that are adapted to deliver a cleaning substance selected enzymes, detergents, or bleaches. When the loaded responsive polymer gels are chosen so that they are capable of delivering a substance into an organic solvents, such as paints or similar products, controlled release devices comprising the polymer gel networks of the invention may be formulated.

Loaded polymer networks of the present invention also find use as wound dressings. For example, a medicament like hyaluronic acid, along with one or more protectants, may be loaded into a polymer network that itself is incorporated into a bandage, gauze or other conventional wound dressing. Upon activation by an appropriate environmental trigger such as a temperature change or a change in pH, the gel delivers the entrained medicament to the wound environment. If the gel is triggered to expand and release the medicament, it may also incorporate wound exudates at the same time.

Loaded polymer networks of the invention also find use as iontophoretic devices. Iontophoretic function of a polymer network of the invention may conveniently be studied in vitro in a commercially available Franz-type transport cell. A polymer network of the invention is loaded with a drug according to procedures described herein. The loaded gel is placed in the reservoir of a well type electrode. The upper (donor) portion of the cell is separated from the buffer-filled bottom (receptor) portion by a membrane (e.g., porcine skin or a synthetic membrane). In a typical protocol, current is applied to the anode which drives the positively charged drug through the membrane into the receptor solution. The amount of drug in the receptor solution is assayed using, for example, HPLC.

Polymer networks and biologically active solutes and protectants that are loaded within the network may be used in pharmaceutically-effective amounts, with or without a compatible carrier. The term "carrier" includes any liquid, gel, capsule, fluid, ointment, cream, lotion or the like, which is encapsulates or otherwise incorporates the loaded gels of the present invention. Carriers should be suitable for use in, or on a subject and should not interact with components of the polymer network in a deleterious manner. The term "compatible", as used herein, means that the components of the pharmaceutical compositions are capable of being commingled with the polymer network of the present invention, and with each other, in a manner such that there is no interaction which would substantially reduce the pharmaceutical efficacy of the pharmaceutical. A "pharmaceutically-effective amount" of a biologically active material or polymer network containing the material is that amount which produces a result or exerts an influence on the particular condition being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such a peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogen-free water; isotonic saline; phosphate buffer solutions; cocoa butter (suppository base); emulsifiers, such as the Tweens [Registered ™]; as well as other non-toxic compatible substances used in pharmaceutical formulations. Wetting agents and lubricants such as sodium lauryl sulfate, as well as coloring agents, flavoring agents, excipients, tableting agents, stabilizers, antimicrobials, antioxidants, and preservatives, can also be present. Other compatible pharmaceutical additives and actives (e.g., NSAID's; pain killers; muscle relaxants) may be included in the pharmaceutically-acceptable carrier for use in the compositions of the present invention. For example, local anesthetics (e.g., benzyl alcohol; lidocaine) may be included in the pharmaceutically-acceptable carrier.

The formulations include, but are not limited to, those suitable for oral, buccal, rectal, topical, nasal, ophthalmic or parenteral (including subcutaneous, intramuscular and intravenous) administration, all of which may be used as routes of administration for practicing the present invention. Other suitable routes of administration include intrathecal administration directly into spinal fluid (CSF), direct injection onto an arterial surface to prevent re-stenosis, and intraparenchymal injection directly into targeted areas of an organ.

Formulations of the present invention suitable for oral administration may be presented as discrete units such as capsules, cachets, tablets or lozenges, each containing a predetermined amount of the potentiating agent as a powder or granules; as liposomes containing a loaded gel; or as a suspension in an aqueous liquor or non-aqueous liquid such as a syrup, an elixir, an emulsion or a draught.

Formulations suitable for parenteral administration conveniently comprise a sterile aqueous preparation of the active solute, which is preferably isotonic with the blood of the recipient.

Nasal spray formulations comprise purified aqueous solutions of the active solute with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

In addition to the aforementioned ingredients, the formulations of this invention may further include one or more accessory additives incorporated into the gel selected from diluents, buffers, biocides (e.g., chlorhexidine gluconate, triclosan, povidine-iodine, and the like), adhesives (e.g., lectin, pectin, fibronectin, and the like), flavoring agents, binders, anti-microbials, skin permeation enhancers, disintegrants, surface active agents, thickeners, lubricants, preservatives (including antioxidants), protectants (e.g., sugars, amino acids, nonionic surfactants) and the like.

The pharmaceutical compositions may be in the form of a sterile injectable aqueous or oleaginous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectibles.

Another embodiment of the invention is a crosslinked, responsive polymer gel network comprising polymer chains interconnected by way of multifunctional crosslinker. The polymer chains and crosslinker have a known acceptable toxicological profile, hereinafter "KATP". It is desirable that such responsive polymer gels that are environmentally safe and safe for use in humans. For purposes of clarity, the following outlines several features and aspects of the invention.

TABLE OF CONTENTS:

I. Morphology, definitions

II. Design Pathways

III. Starting Materials
  A. Polymer
  B. Crosslinker
  C. Functional Groups
  D. Additives
IV. Responsive Gel Networks
V. Methods of Preparing Polymer Networks
  A. General Considerations
  B. Microporous Gels
VI. Biologically Active Compounds
VII. Utilities/Formulations
  A. Loading Biologically Active Compounds into Polymer Networks
VIII. Examples
I. Morphology, definitions The materials of the present invention are three-dimensional, permanently crosslinked polymer networks. As defined herein, a "polymer network" is that three-dimensional structure resulting from the crosslinking of polymers. Preferred polymers are chemically-crosslinked. "Chemically crosslinked" means that a multifunctional chemical reagent is added during synthesis which reacts with, and interconnects via covalent bonding, two or more polymer chains. The term "chemically crosslinked" is not meant to include gamma radiation, photochemical, electron beam, or ultraviolet crosslinking when these methods are intended to replace a chemical moiety used as a crosslinker. Thus, direct crosslinking of hydroxypropyl cellulose with itself using radiation is not intended to be included within the scope of this invention.

The multifunctional chemical reagent is the "crosslinker". The form that the crosslinker takes once the polymer network has been formed is defined as the "crosslinkage". For example, and as discussed more fully below, succinyl chloride is a crosslinker that may not have a KATP but, once it is reacted in solution and crosslinked, it converts to succinic acid crosslinkage which does have a KATP. It will be understood by those having ordinary skill in the art that, not every single crosslinking reaction will produce the desired KATP crosslinkage; some defects may arise. Nevertheless, within the constraints of good manufacturing practice for materials of this type that are well known to those of ordinary skill in the art, it is considered that gels of the present invention have crosslinkages that all have a KATP, although the starting material crosslinker (e.g., precursor acyl halide derivative) may not have a KATP. Likewise, the polymer chains themselves may have impurities or other imperfections that are considered to be within tolerance requirements for materials of this type when used for the particular purposes of the present invention. Similarly, within the constraints of good manufacturing practice for materials of this type that are well known to those of ordinary skill in the art, it is considered that gels of the present invention all have a KATP.

In particular, the preferred three-dimensional polymer networks are homogeneous or microporous gels. The term "gel" refers to materials between the liquid and solid state containing enough solvent molecules to cause macroscopic changes in the sample dimension. The term "gel" also includes polymer gel networks in which virtually all liquid (i.e., solvent) has been driven off, leaving a "dry" gel. The term "microporous" refers to two-phase systems of a continuous solid phase containing numerous pores filled with fluid. A "microstrticture" as defined herein, refers to those structures of a gel (e.g., pores, voids, walls and the like) observable under a scanning electron, or other, microscope and ranging in size from 0.01 to about 100 microns. Gels containing pores in the size range 0.01 to about 10 microns are 'microporous'. If some of the pores are interconnected, the gel is typically called an "open-cell" gel. If all the pores in the gel are interconnected to each other, the gel is a "bicontinuous" gel. If the pores are discrete (not connected to each other), so that the internal space of each pore is independent of the other pores, the gel is a "closed-cell" gel. The present invention encompasses as all these morphological forms and combinations of these forms.

Microporous responsive gels may be "fast response" gels. As defined herein, "fast response" means that the gel reaches 90% of its maximum volumetric swelling or 90% of its minimum volumetric collapse in a time that is at least ten times faster than a comparable non-porous gel of the same geometry when both gels are subjected to a similar change in an environmental condition.

The polymer gel network materials described herein may also be employed in a variety of forms. For example, the materials may be used as films or membranes, tubes, hollow fibers, solid fibers, molded objects, solid particles, capsules, micelles or liposome-like structures. They may also be applied as coatings on solid surfaces (e.g., catheter tips) or in the pores of porous solids, as solutions, particulate suspensions and the like. Coatings may be applied to and/or attached to polymers, metals, ceramics, glasses, carbons and the like.

II. Design Pathways

The polymer gel networks of the present invention and their component parts are intended to have a known acceptable toxicological profile (hereinafter "KATP"). This term refers to the ability of a given polymer gel network or component thereof to successfully pass regulatory approval by an appropriate governmental body or industry group responsible for the safety of drugs, cosmetics, medical devices, pharmaceuticals, food additives, food processing and the like when the drugs, cosmetics, medical devices, pharmaceuticals, food additives, food processing and the like, are used in animals, including humans. More particularly, and at least in the United States, a polymer network of the present invention is considered to have a KATP if the network, and its polymer/crosslinker components, are considered by the U.S. Food and Drug Administration ("U.S. FDA") to be safe for a particular use as cited in Section 21 of the Code of Federal Regulations ("21 C.F.R."), relevant sections of which are described below and incorporated herein by reference. Moreover, certain industrial groups have also provided lists of materials that are intended to be included within the scope of this invention, such groups in the United States including the Cosmetic, Toiletries and Fragrances Association (hereinafter "CTFA").

It will be understood that the U.S. Food and Drug Administration will only approve materials for a specific use and for a particular drug and dosage at issue. For example, materials that are considered to have an KATP suitable for the present invention include those on the "Generally Regarded as Safe" (GRAS) list promulgated by the Food and Drug Administration at 21 C.F.R.182.1–182.8997, when used for the purpose indicated in accordance with good manufacturing practices. GRAS materials useful in forming crosslinked polymer networks of the invention include methylcellulose (21 C.F.R. 182.1480); adipic acid (21 C.F.R. 184.1009) and succinic acid (21 C.F.R. 184.1091). Other materials that are considered to have a KATP are those that are permitted for direct consumption as food additives (amino acids- 21 C.F.R. 172.320), or as binders/fillers, film forming agents and thickeners for food such as ethylcellulose (21 C.F.R. 172.868); hydroxypropylcellulose (21 C.F.R. 172.870); methyl ethylcellulose (21 C.F.R. 172.872); and hydroxypropylmethylcellulose (21 C.F.R. 172.874); modified food starch (21 C.F.R. 172.892). Materials suitable for treating, processing, or packaging food are also considered to have a KATP under the design pathways described herein. Exemplary substances include: polyvinylpyrrolidone (21 C.F.R. 173.55); adipic acid, fumaric acid, sebacic acid, and maleic acid (21 C.F.R. 175.300 (b) (vii) (a)); carboxymethylcel lulose, ethylcellulose, ethyl hydroxyethylcellulose, hydroxypropylinethylcellulose, and methyl cellulose (21 C.F.R. 175.300 (b) (xvi)). It will also be understood that the polymer gel in its crosslinked form must have an aqueous leachate that has a KATP or the aqueous leachate must contain residual moieties (i.e., materials left over from synthesis) such that the solvent is within acceptable limits promulgated by the appropriate regulatory body such as the U.S. FDA. FDA test procedures for determining leachates and residuals from polymeric coatings may be found in 21 C.F.R. 175.300 (Table 2).

Other materials that can functionalize the polymers of the invention and are considered to have a KATP under the pathways described herein are surfactants such as diethanolamide condensates, n-alkyl ($C_8$–$C_{18}$)amine acetates, and di-n-alkyl ($C_8$–$C_{18}$) dimethyl ammonium chloride (21 C.F.R. 172.710).

From these considerations, a number of design pathways have been developed to allow persons having ordinary skill in the art to select materials which have a KATP and which are suitable as building block precursors of the polymer networks described herein.

Pathway Number 1: The individual polymer(s) precursor, the crosslinker used in the synthesis, the final three-dimensional polymer network that is to be used in a particular context (e.g., food separation, drug release, medical devices, cosmetics) and, optionally, the liquid solvent incorporated within a polymer network, must all have a KATP for that particular use or must have a KATP for a related use. Less preferred, although still acceptable under Pathway 1, is the corollary that the crosslinked polymer, as well as the final three-dimensional polymer network that is to be used in a particular use context, e.g., food separations, medical devices, drug release, cosmetics), have a KATP suitable for a different use.

Pathway Number 2: This pathway concerns the methods for making desirable KATP polymer gels. The polymer and crosslinker precursors and any processing aids (i.e., surfactants, anti-foaming compounds, and the like) used in synthesis of a KATP gel must also be used in processes for making other materials that have a KATP for the same, or for a related use. Less preferred, although still acceptable under pathway 2, is the corollary that the precursors and aids are used in other processes for making materials that have a KATP for a different use.

A polymer network falling within any single pathway, or any combination of pathways, is suitable and is intended to be encompassed within the scope of the invention.

What follows are some examples, by no means exhaustive, of the applications of these heuristics:

1. One would like to develop a gel of the invention suitable for use in food separations. It is known that cellulose ethers (i.e., hydroxypropylcellulose-HPC) are suitable as polymer backbones since they have a KATP when used for food additives (See Aqualon Product Data Sheet No. 494.3, Aqualon Company, Little Falls Centre One, 2711 Centreville Road, PO Box 15417, Wilmington, Del. 19850-5417). Cellulose ethers may be crosslinked with adipic acid and both HPC and adipic acid have KATP's for use as food additives (21 C.F.R. 172.870), thus satisfying Pathway 1. Moreover, adipoyl chloride may be used in the synthesis of the adipic acid crosslinkage (See S. H. Pine et al., *Organic Chemistry*, McGraw-Hill, p. 319 (1980) and Example 1, infra). Adipoyl chloride is used in the production of commercial penicillins (See, for example, R. G. Laubeck et al., "Gas Chromatographic Determination of Carboxylic Acid Chlorides and Residual Carboxylic Acid Precursors Used in the Production of Some Penicillins", *J. Chrom. Sci.*, Vol. 14, (May 1976)), which is consistent with Pathway 2. Further, an aqueous leachate from a polymer gel consisting of HPC crosslinked with adipic acid would be adipic acid and/or the cellulose ether (both KATP materials).

2. One would like to develop a gel of the invention suitable for use in parenteral drug release (Siegel et al., *J. Contr. Release*, 8: 179–182 (1988); Hoffman, *J. Controlled Release*, 6: 297–305 (1987)). Similar considerations apply to developing suitable pathways for selection of these materials. Cellulose ethers (i.e., hydroxypropylcellulose-HPC) are suitable as polymer backbones since they have a KATP when used for food additives (Aqualon Product Data, supra). Cellulose ethers may be crosslinked with adipic acid and both HPC and adipic acid have KATP's for use as food additives (see above), thus satisfying Pathway 1. Moreover, adipoyl chloride may be used in the synthesis of the adipic acid crosslinkage (see above), thus satisfying Pathway 2. Further, an aqueous leachate from a polymer gel consisting of HPC crosslinked with adipic acid would be adipic acid and/or cellulose ether.

3. One would like to develop a pH-sensitive polymer gel suitable for use in agricultural controlled release. Cellulose ethers (i.e., hydroxypropylcellulose-HPC) are suitable as polymer backbones since they have a KATP when used for food additives (Aqualon Product Data, supra). Cellulose ethers may be crosslinked with adipic acid and both HPC and adipic acid have KATP's for use as food additives (see above), thus satisfying pathway 1. Surfactants such as diethanolamide condensates, n-alkyl (—$C_8$–$C_{18}$)amine acetates, and di-n-alkyl ($C_8$–$C_{18}$) dimethyl ammonium chloride (21 C.F.R. 172.710), suitable for use with pesticides, may be added to the gel, satisfying Pathway 2 that starting materials may be used in processes for making other KATP materials.

Persons having ordinary skill in the art may readily determine if a particular material is suitable for use in the polymer networks of the present invention. Such persons need access to governmental regulatory agency rules that describe acceptable materials for a particular use. See above-cited FDA regulations. Those having ordinary skill in the art will readily appreciate that specific materials considered to have a KATP will not necessarily be the same among countries having governmental agencies analogous to the U.S. FDA. Nevertheless, such persons will be able to ascertain which materials would have a KATP suitable for use in foreign countries by contacting the relevant, counterpart agency in that country. For example: in France the counterpart to the U.S. FDA is the Agence Francaise du Medicament- 143–145, boulevard Anatole France- 93200 Saint Denis; in the United Kingdom, the counterpart agency is the Medicines Control Agency, Market Towers, London, SW8 5NL; in Japan, the counterpart agency is the Ministry of Health and Welfare (drugs and devices for human use) and the Ministry of Agriculture and Fisheries (drugs and devices for non-human use); in Canada, the counterpart agency is the Drug Regulatory Affairs Division (drugs and devices for human use) and the Department of Agriculture (drugs and devices for veterinary use); in Germany, the counterpart agency is the Bundesgesundheitsamt, Institut fur Arzneimittel, Berlin.

III. Starting Materials

A. Polymer

Polymeric starting materials most suitable for the present networks are crosslinkable materials polymerized via peptide bonds, phosphate ester bonds and ether bonds. Exemplary polymers are natural product polymers derived from a living organism (i.e, of algal, microbial, animal, plant origin). Exemplary algal natural polymers include agar, furcelleran, alginate, carageenan. Exemplary plant natural polymers include starch, cellulose, pectin, gum arabic, guar gum, tracaganth, ghatti seed gums, locust bean gum. Exemplary microbial polymers include xanthan, pullalan, dextran, gellan. Exemplary animal polymers include chitin, chitosan, heparin, hyaluronic acid and collagen.

Many of these are already KATP materials that include water-soluble, linear polymers such as polysaccharides (e.g., cellulose, food starch-modified (21 C.F.R. 172.892), chitin, chitosan, hyaluronic acid, xanthan gum (21 C.F.R. 172.695), chondroitin sulfate, heparin, and the like) and hydroxyalkyl, alkylhydroxyalkyl and alkyl-substituted cellulose derivatives such as cellulose ethers. Exemplary cellulose ethers include methylcellulose (MC), hydroxyethylcellulose (HEC), ethylhydroxyethylcellulose (EHEC), hydroxyethylmethylcellulose (HEMC), hydroxypropylmethylcellulose (HPMC), hydroxypropylcellulose (HPC), carboxymethylcellulose (CMC), and hydroxymethylcellulose (HMC). Cellulose ethers suitable for use in the present invention are readily available under a variety of trade names from a variety of manufacturers, for example: MC ("Methocel A"—Dow Chemical Company; "Metulose SM"—Shinetsu Chemical Company); HPMC ("Methocel E"—Dow Chemical Company; "Celacol HPM"—British Celanese Ltd.); HEC ("Cellosize WP"—Union Carbide Corporation); HPC (Aqualon Inc.).

Responsive polymers of amino acids such as poly(L-proline), and poly(valine-proline-glycine-X-glycine) [where X=tyrosine, phenylalanine, leucine, valine, glutamic acid, lysine, glycine, and other amino acids], as well as polypeptides like gelatin may also be used. Polynucleotides such as ribo- and deoxyribonucleotides are also suitable for crosslinking according to the invention.

Responsive polymers suitable for synthesis of KATP networks may also be KATP synthetic polymers such as polyethylene glycol (PEG)- e.g., 21 C.F.R. 172.210, 172.770, 172.820, 173.310; polyvinylalcohol (PVA- 21 C.F.R. 175.300 (xv)); polyethylene oxide (21 C.F.R. 172.770) and the like.

B. Crosslinkers

Crosslinkers are those chemical reagents with suitable KATP that are capable of linking polymer backbones. Specific crosslinkers will depend upon the polymer but preferred crosslinkers for polysaccharides, especially modified food starches and cellulose ethers, are multifunctional carboxylic acids, such as adipic acid (hexanedioic acid: HOOC(CH$_2$)$_4$COOH), succinic acid (HOOC(CH$_2$)$_2$COOH), malonic acid (propanedioic acid: CH$_2$(COOH)$_2$), sebacic acid (decanedioic acid: HOOC(CH$_2$)$_8$COOH), glutaric acid (pentanedioic acid: HOOC(CH$_2$)$_3$COOH), or 1,10 decanedicarboxylic acid. Dicarboxylic hydroxyacids may also have suitable KATP's such as tartaric acid and malic acid as well as multifunctional carboxylic acids such as 1,2,3,4-butanetetracarboxylic acid.

Persons having ordinary skill in the art will readily appreciate that esterification reactions between the hydroxyl groups of the ether and the carboxyl group on the preferred crosslinkers provides the crosslinkage arrangement. It will be further understood that certain ethers will participate in more active crosslinking than others. It has been found that adipic acid will not produce a useful crosslinkage with HPC and HPMC while it will crosslink HEC. This is probably due to the steric hindrance to esterification of the crosslinker afforded by the secondary and tertiary alcohols of HPC and HPMC, as opposed to the less sterically hindered primary alcohols of HEC.

Unsaturated dibasic acids have been used to physically crosslink water soluble polymers by application of drying and/or heat. See, for example, U.S. Pat. No. 3,379,720 (Reid, incorporated herein by reference). Unfortunately, the heat required to crosslink water soluble polymers within a reasonable time of several hours is very high, ranging from 90° C. (2–3 hour gelation) to 200° C. (1–2 minute gelation). This may render the Reid method unsuitable for use with heat labile, biologically active compounds. At room temperature, the Reid methodology produced a gel in 10–30 days.

One of the present methods for crosslinking directly with multifunctional carboxylic acids involves azeotropic distillation to ensure that the water formed during the esterification reaction is continually removed from the reaction system. However, this method is limited to highly reactive compounds. See Examples.

It has, however, been discovered that a preferred method of effective crosslinking may be accomplished in 3–4 hours by using acyl halide derivatives of multifunctional carboxylic acids as the crosslinker reagents added to the polymer solution. These acyl halides preferably are chloride derivatives such as adipoyl chloride, sebacoyl chloride, succinyl chloride, and the like. Acyl chloride derivatives of multifunctional carboxylic acids are very unstable in water and will react almost immediately to form the corresponding acid in solution (e.g., S. H. Pine et al., *Organic Chemistry*, supra, p. 319) and it is this acid, not its halide derivative, that becomes incorporated into the final form of the polymer network as the crosslinkage. As a result, one embodiment of the synthesis requires use of anhydrous conditions and anhydrous solvents but without the need for azeotropic distillation . See Examples. Furthermore, because the halide derivative is so reactive with water, aqueous leaching of a polymer network with any residual halide derivative will necessarily yield the acid form of the crosslinker in the leachate, not the halide derivative. Thus, the leachate is a KATP material.

C. Functional Groups

The three-dimensional polymer networks described herein may also be functionalized during synthesis with one or more surfactants, affinity ligands (e.g., monoclonal antibodies), chelators, enzymes, and the like that are immobilized in or on the polymer network. The term "immobilize" refers to physical trapping of a functionality within a polymer network as well as chemical bonding of a functionality via covalent, or other bonding, within a polymer network. Methods of immobilizing such functionalities to polymer networks are well known to the practitioner. See, for example, Hoffman and Monji, U.S. Pat. No. 4,912,032, McCain et al., U.S. Pat. No. 4,737,544, O'Driscoll et al., U.S. Pat. No. 3,859,169, incorporated herein by reference.

For example, immobilization of a ligand within KATP polymer gel networks allows the ligand to be exposed to, and/or isolated from, an environment by changing the gel's volume (see discussion on "responsive" gels, below). That is, a substance may be delivered to or removed from an environment by employing a ligand immobilized within a responsive KATP polymer gel of the present invention. The immobilized ligand may be selected for its capability of specifically binding with a substance although the ligand may also bind non-specifically.

A ligand (e.g., an enzyme or antibody) may be physically trapped and protected within a polymer gel or may be immobilized to a polymer chain by linkages that are labile to enzymes or aqueous solvent having a specific pH or temperature. A drug, antibody, or other molecule may be immobilized to, for example, cellulose ether moieties and the gel kept in a dry or shrunken state. When such a gel is swollen, it will incorporate solvent and if the solvent can degrade the labile linkage(s), the drug or antibody or other molecule will be released from the gel into the environment.

The material immobilized in the KATP polymer gels described herein may also be a binding component of an affinity binding pair. Suitable binding pairs include an antibody which binds with an antigen or hapten of interest; a receptor that binds with a hormone, vitamin, dye or lipid binding partner in solution; lectins that bind with polysaccharides; DNA or RNA that binds with complementary DNA,RNA, or oligonucleotides; ions that bind with chelators; and the like.

In another embodiment, a chemically active reactant may be immobilized to provide a means for controlling a reaction. Using the preferred responsive gels described below, reactions may be cycled on and off as exposure of the immobilized reactant to a reaction condition is regulated by altering the volumetric changes of the gel containing the reactant. Such a system could include an enzyme or antibody immobilized in or on a KATP gel of the present invention to catalyze a reaction with a substrate in a solution of interest. See for example, Hoffman and Monji, U.S. Pat. No. 4,912,032, incorporated herein by reference.

Most preferably, the functional moieties (e.g., affinity ligands) also have a known acceptable toxicological profile.

D. Additives

"Additives" are defined herein as materials incorporated into a responsive polymer gel network of the invention that have a KATP suitable for the particular use of that gel. Additives include, but are not limited to, stabilizers, biocides, anti-microbials, adhesives.

IV. Responsive Gel Networks

The most preferred polymer networks of the invention are gels that are "responsive", i.e., when challenged with an environmental change, the environmental change affects the gel by causing the entire gel, or a component thereof, to undergo a reversible volumetric change in which the gel expands from a less liquid-filled state or dry state to a more liquid-filled state; or collapses from a more liquid-filled state to a less liquid-filled state. Polymer gels used in the present method may be expanded by either (i) contacting a dried gel with a solvent and allowing the gel to non-reversibly swell with solvent and incorporate any moiety (e.g., a drug, affinity ligand) contained in the solvent; (ii) initiating a reversible volumetric expansion of the gel to incorporate solvent (and any moiety contained therein) by triggering the expansion with a stimulus; or (iii) a combination of (i) and (ii). In this context, the term "incorporate" refers to both absorption of a material inside the gel network and adsorption of a material on a surface of the gel.

The degree of volumetric change between collapsed and expanded states of the preferred "responsive" gels at their particular environmental transition region is quantitively much greater than the volume change of the gel outside the environmental transition region. Equations describing this volume behavior are not simple monotonic functions (as they are for conventional hydrogels) but contain one particular environmental transition where the volume change is much larger than at other environmental transitions for the same gel.

The primary requirement of a gel of the invention is that the entire gel, or a component, undergo a volume change. The gel as a whole may meet these requirements. Nevertheless, the gel may itself include several other components as long as at least one component(s) provides the required property.

For instance, the gel may be a single material such as a single polymer network which meets the volumetric response requirement. The gel may also be a co-polymer, whether a random, alternating, or block co-polymer, that has a KATP and which meets the volumetric response requirement. The gel may also include two or more polymers, each component polymer having a KATP so long as the result is a physical polymer blend, wherein at least one polymer meets the volumetric response requirement.

The gel may also be an interpenetrating polymer network (IPN) in which each KATP polymer maintains its properties. An IPN may possess only a volume change property such as an IPN of HPC and carboxymethylcellulose. A responsive gel may also be combined in an IPN with a sorptive-type gel to meet the requirements of vapor extraction, drug delivery, electrophoresis, or other delivery system. Thus, a purely responsive polymer may itself be combined in an IPN with a polymer that has a sorptive component. The IPN may possess both properties, however, so that at least one polymer member of the IPN provides the sorptive property and at least another polymer member provides the volume change property. This type of configuration is particularly useful in drug delivery systems.

The reversible volume change of the entire gel, or a component thereof, may be either continuous or discontinuous. A "continuous" volume change is marked by a reversible change in volume (i.e. a collapse or swelling) that occurs over a relatively large change in environmental condition. Moreover, there exists at least one stable volume near the transition between the swollen and collapsed states.

Gels of the invention may undergo a "discontinuous" volume change in which the reversible transition from swollen to collapsed states, and back again, occurs over an extremely small change in environmental condition, such as less than 0.1 degree C. or 0.1 pH unit. Such reversible gels are often called "phase-transition" gels. See, for example, Hirotsu et al., *J. Chem. Phys.* 87: 15 July 1987 describing synthetic polymeric gels that undergo phase transitions. There is no stable volume between the swollen and collapsed states at the phase-transition and, in theory, the expansion and/or collapse occurs over an infinitesimally small environmental change. A gel undergoing a continuous phase-transition may have a similar order of magnitude total volume change as a gel undergoing a discontinuous phase-transition.

On a molecular level, the preferred responsive gels are sensitive to small changes in a restricted repertoire of environmental "trigger" conditions consisting primarily of temperature, pH, solvent concentration, and ion concentration. On a macroscopic level, any of a variety of environmental changes may be imposed on the gel which allows the specific trigger to induce a volume change. These environmental conditions may, but not necessarily, be the same as the trigger and include, but are not limited to, a change in temperature, electric field, photon energy, pH, solvent composition, ion concentration, concentration of biomolecules, pressure, and the like. The preferred gels of the invention may be combined with a material that acts as a molecular "transducer", converting an environmental condition into an appropriate trigger. For example, a dye may be introduced into a temperature-triggered responsive gel. The dye is designed to trap light of a given wavelength and convert the light energy into heat, thus triggering the gel to undergo a temperature-induced volume change. See also, A. Suzuki and T. Tanaka, *Nature:* 346: 6282 (1990), incorporated herein by reference.

The volumetric changes of gels described herein result from competition between intermolecular forces, usually electrostatic in nature, that act to expand the polymer network; and at least one attractive force that acts to shrink it.

Volumetric changes in aqueous gels are driven primarily by four fundamental forces: ionic, hydrophobic, hydrogen bonding and van der Waals bonding interactions, either alone or in combination. Each of these interactions may be independently responsible for a volume transition in preferred gels of the invention. Each of these fundamental forces is most strongly affected by a particular trigger. Changes in solvent concentration most strongly affect the van der Waals interaction; changes in temperature most strongly affect hydrophobic interactions and hydrogen bonding; and changes in pH and ion concentration most strongly affect ionic interactions.

Thus, a gel whose volume change is governed by ionic interactions would include components that are weakly acidic and weakly basic, such as poly(methylmethacrylate)/dimethylaminoethyl methacrylate (See Siegel and Firestone, *Macromolecules,* 21: 3254–3259 (1988)) and cellulose ethers such as HPC crosslinked by methods described herein. Gels of this type are sensitive to pH. See Example 6.

Gels whose volume change is governed by hydrogen bonding will collapse with a decrease in temperature and are exemplified by interpenetrating polymers that comprise acrylamide as one polymer, acrylic acid as the other polymer, and water as the liquid medium. Gels whose volume change is governed by hydrophobic interactions will collapse when challenged with an increase in temperature and are exemplified by N-isopropylacrylamide. Gels whose volume change is governed by van der Waals interactions will behave similarly to those governed by hydrophobic interactions.

Gels may be formulated in which the volume change is governed by more than one fundamental force. In particular, gels consisting of copolymers of positively and negatively charged groups meet this requirement. In these gels, polymer segments interact with each other through ionic interactions and hydrogen bonding. The combination of these forces results in the existence of several pH-driven phases. See Annaka and Tanaka, *Nature* 355: 430–432 (1992), incorporated herein by reference.

Volumetric changes in gels can be derived from their equations of state that relate three characteristic state variables of the gel: volume (V) or equivalent density of the polymer network ($\phi$), temperature (T) plus polymer-solvent interaction parameter ($\Delta F$), and the osmotic pressure($\pi$). At equilibrium, the osmotic pressure of a gel must be zero ($\pi=0$).

Without wishing to be bound by any particular theory, and as but one example of the theories developed in the field, one may determine the temperature (Tc) of the phase transition where ($\Theta$) is the theta temperature of the polymer network in the solvent, and $\phi_o$ is the concentration of the polymer network when in a random walk configuration, using equation 1.

$$T_c = \Theta(1 \pm 22.5\phi_o) \quad \text{(Equation 1)}$$

Figure 3:
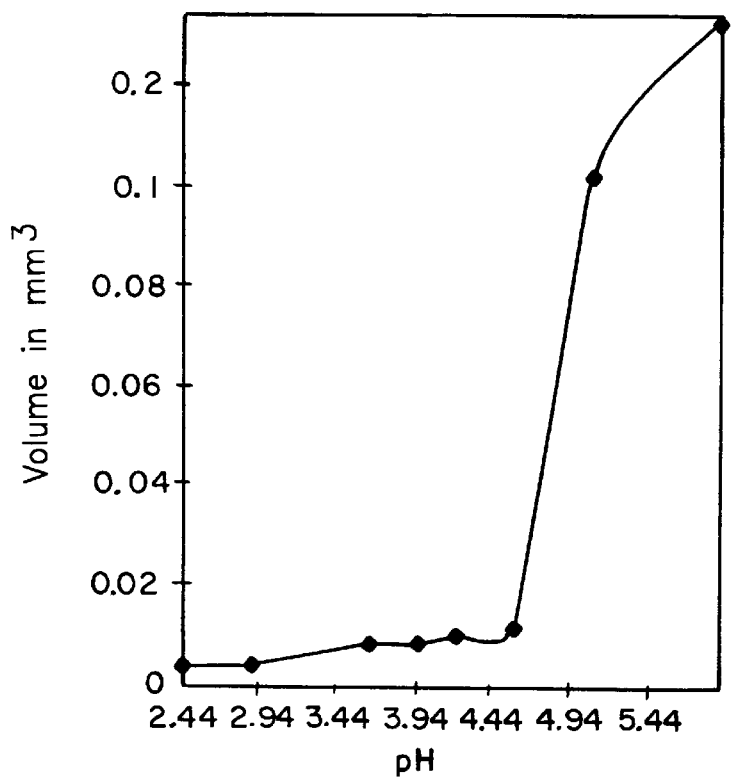
FIG. 3 is a pH-volume relationship for a crosslinked modified food starch gel of the invention.
Figure 4:
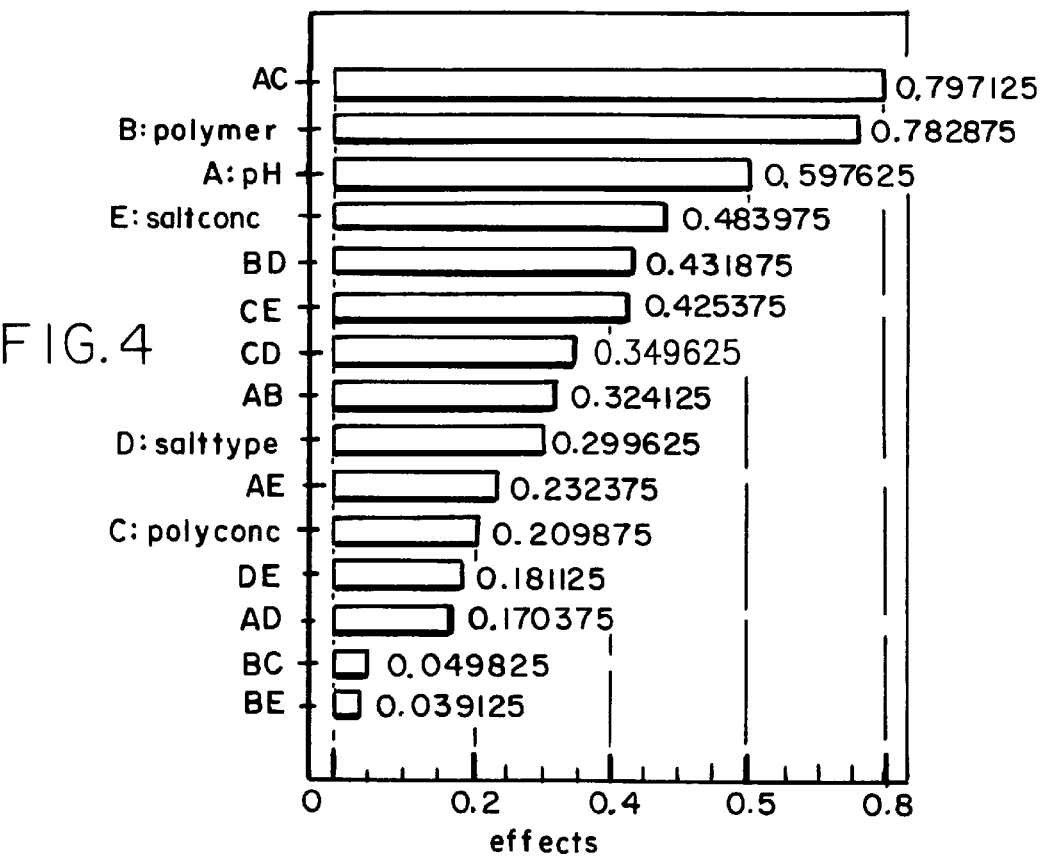
FIG. 4 is a Pareto chart relating to loading solution factors of biologically active solutes (peroxidase) loading into crosslinked polysaccharide gel network (HPCAA hydrogel)
Figure 5:
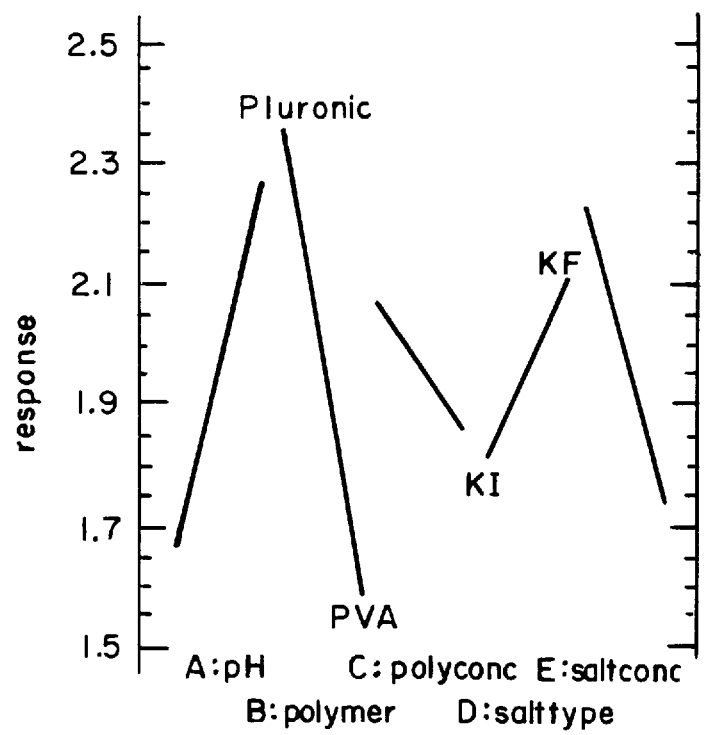
FIG. 5 illustrates the main effects of loading solution factors on enzyme partitioning into HPCAA hydrogels.
Figure 6:
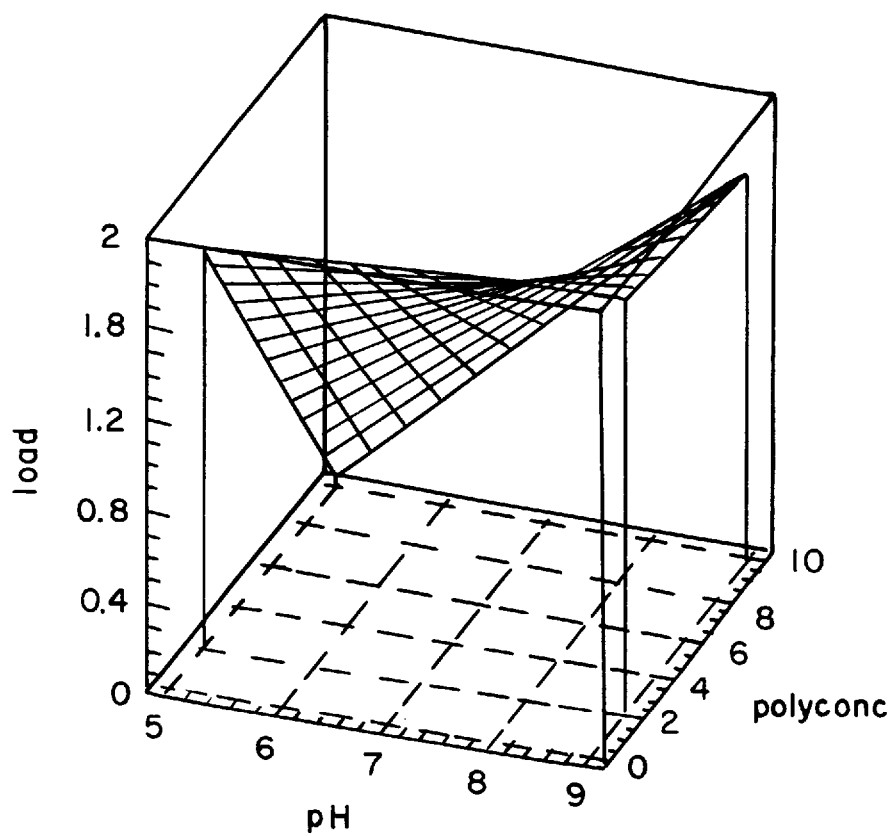
FIGS. 6–9 illustrate representative response surface plots of loading optimization in connection with PVA.
Figure 7:
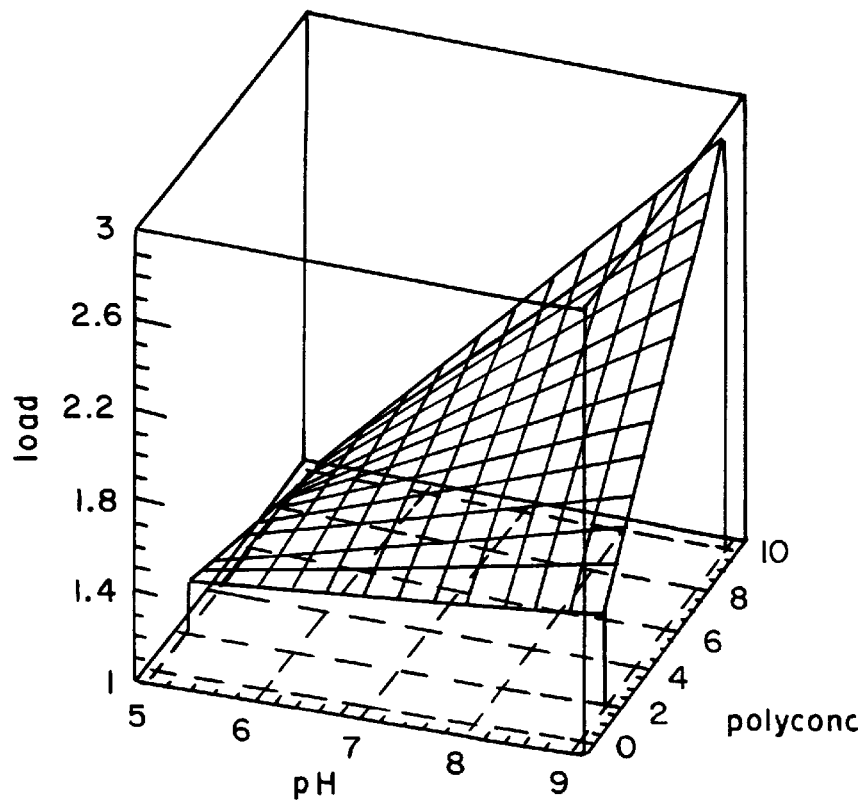
Figure 8:
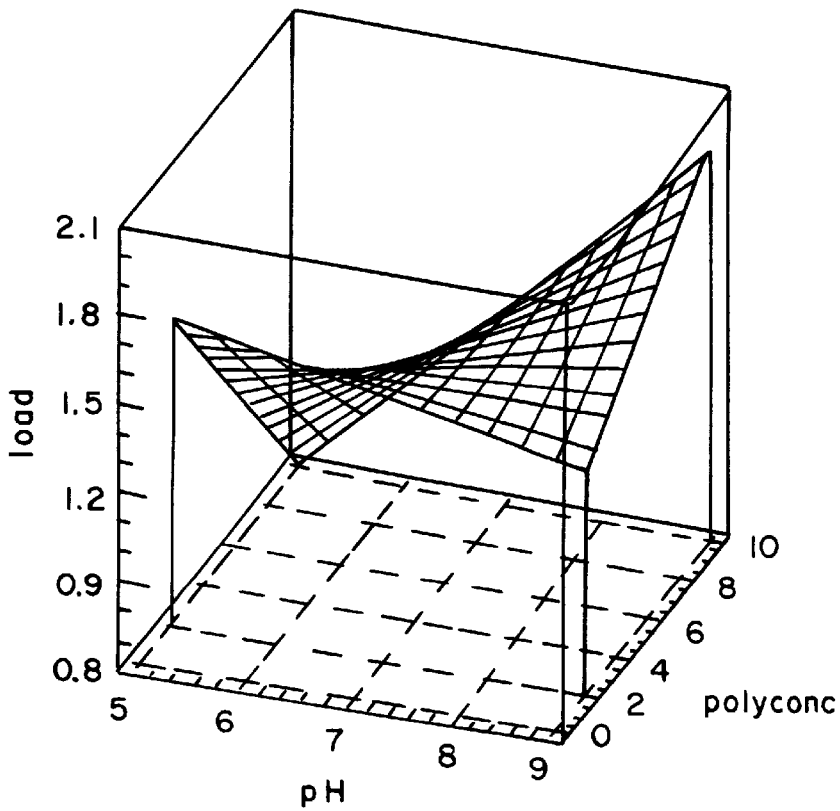
Figure 9:
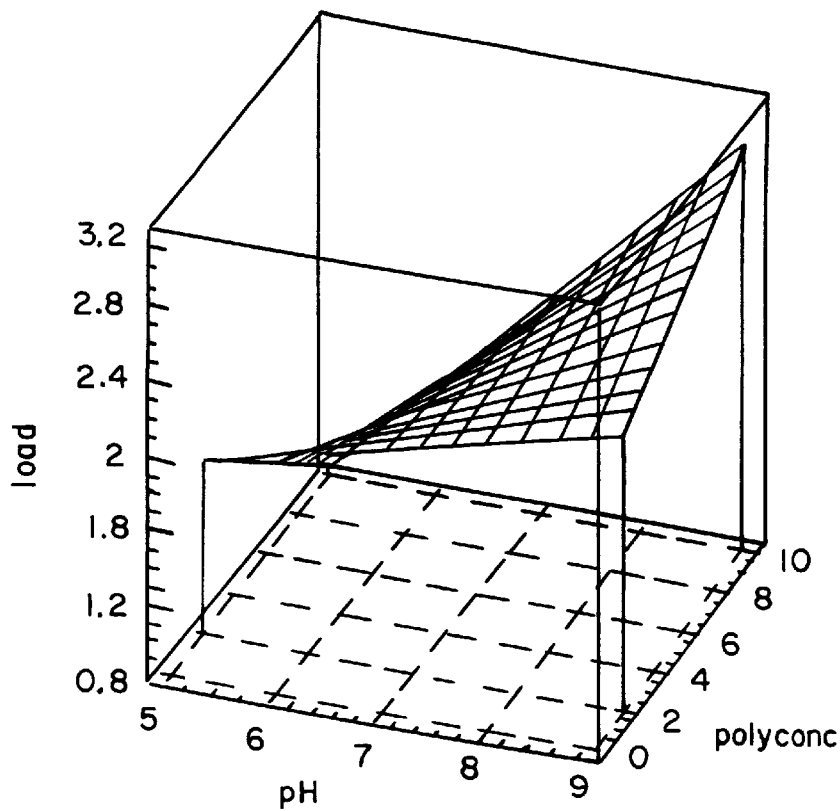
Figure 10:
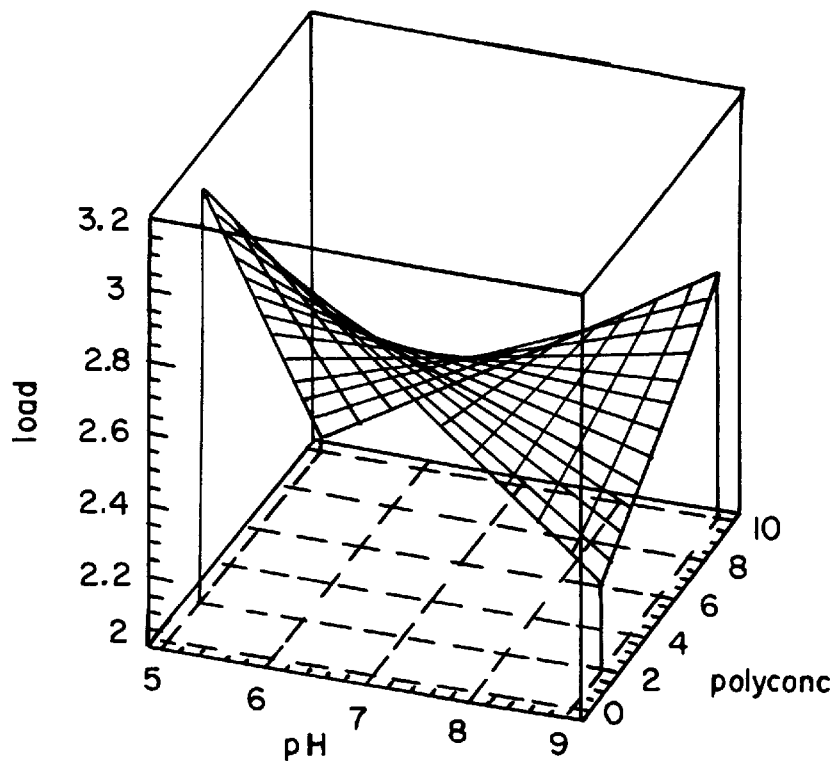
FIGS. 10–13 illustrate representative response surface plots of loading optimization in connection with PLURONIC®.
Figure 11:
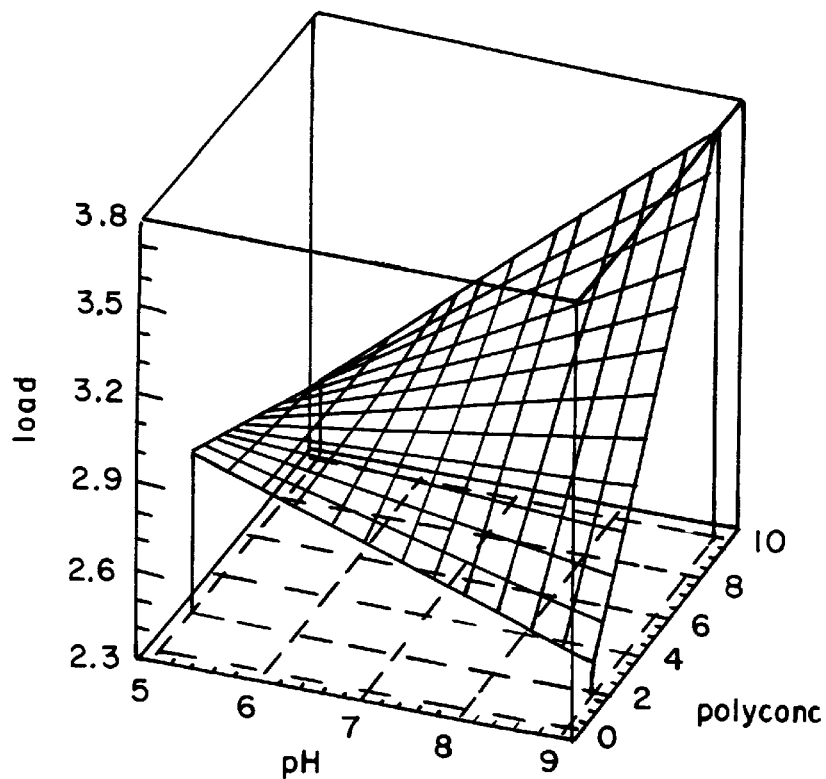
Figure 12:
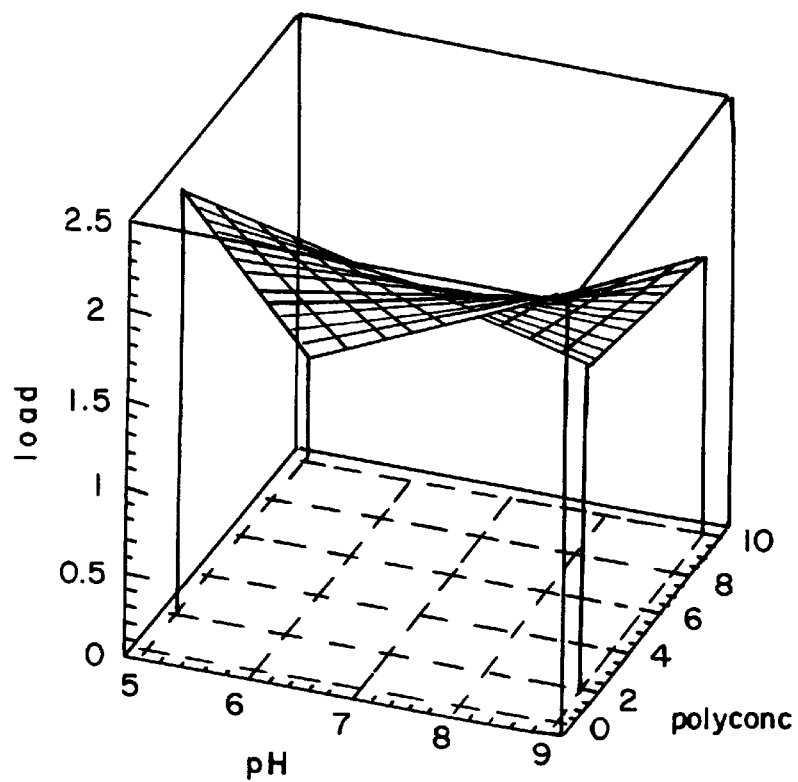
Figure 13:
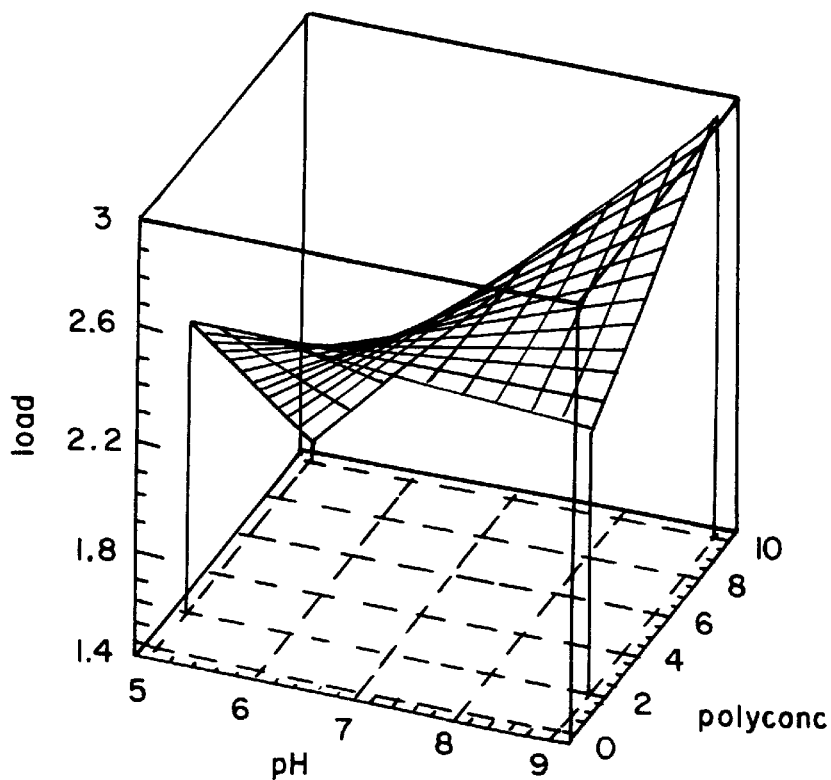
Figure 14:
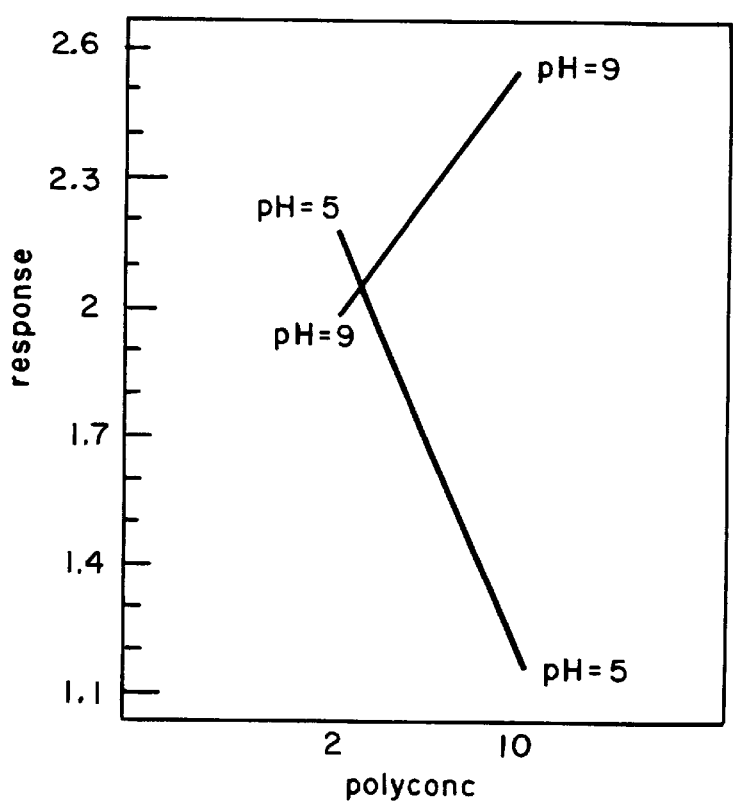
FIGS. 14–19 are plots illustrating interactions between loading solution variables and their effects on protein loading into environmentally safe, crosslinked polysaccharide gel networks.
Figure 15:
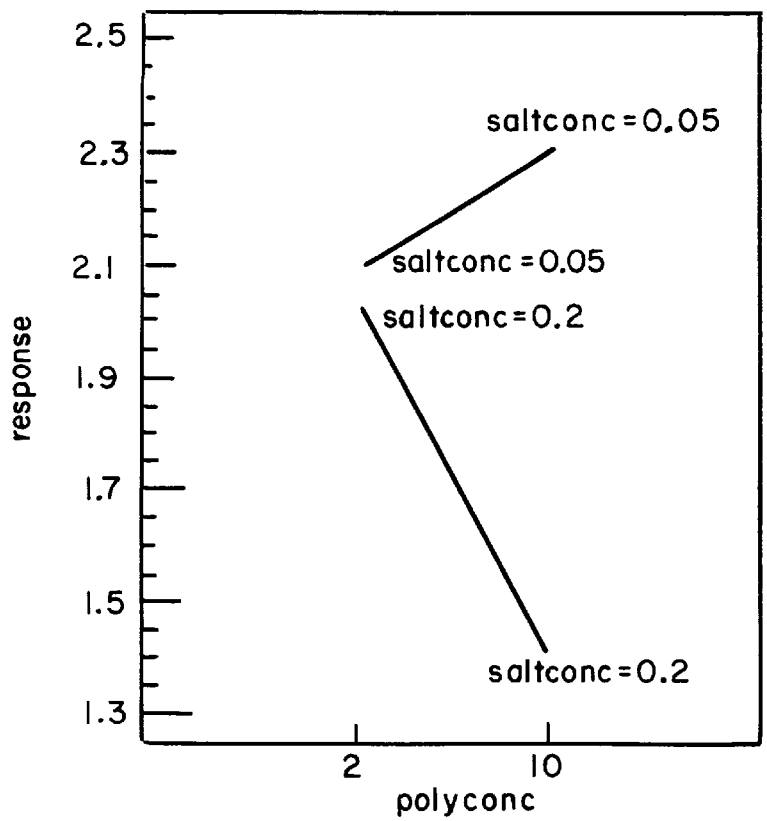
Figure 16:
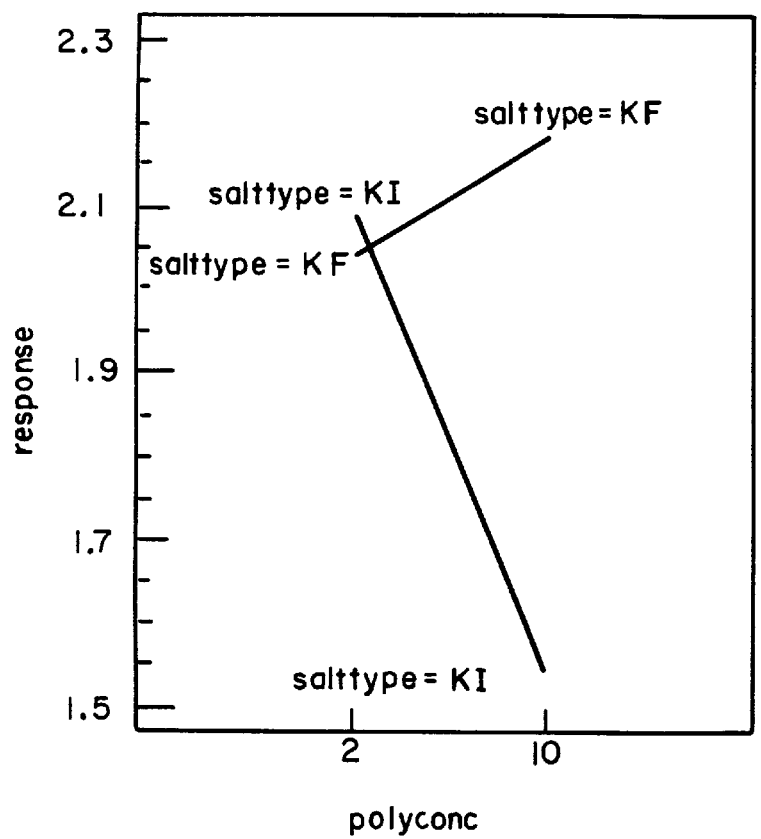
Figure 17:
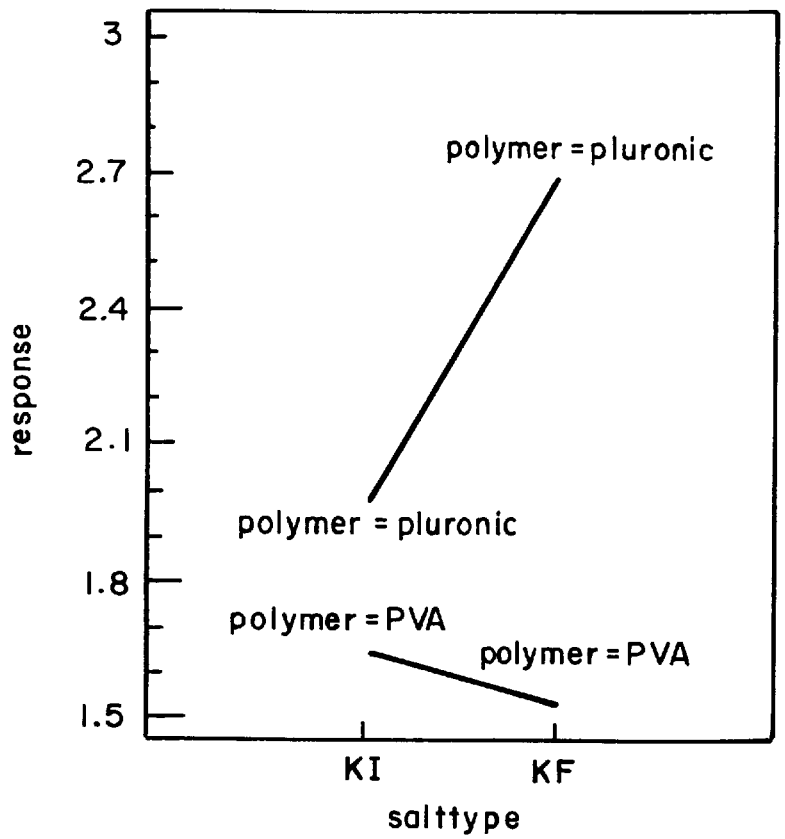
Figure 18:
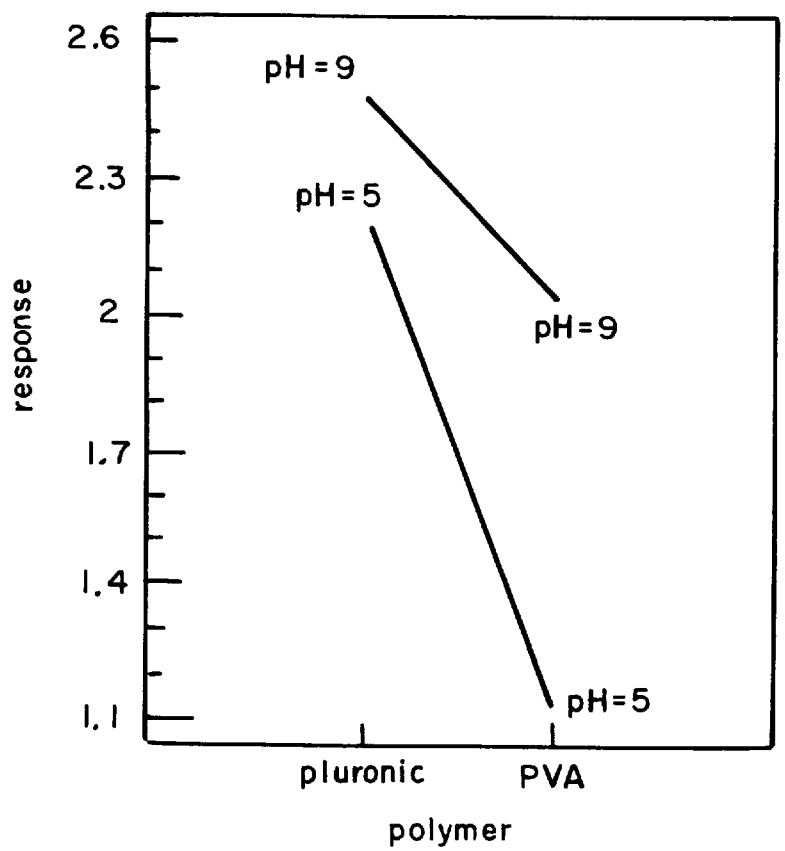
Figure 19:
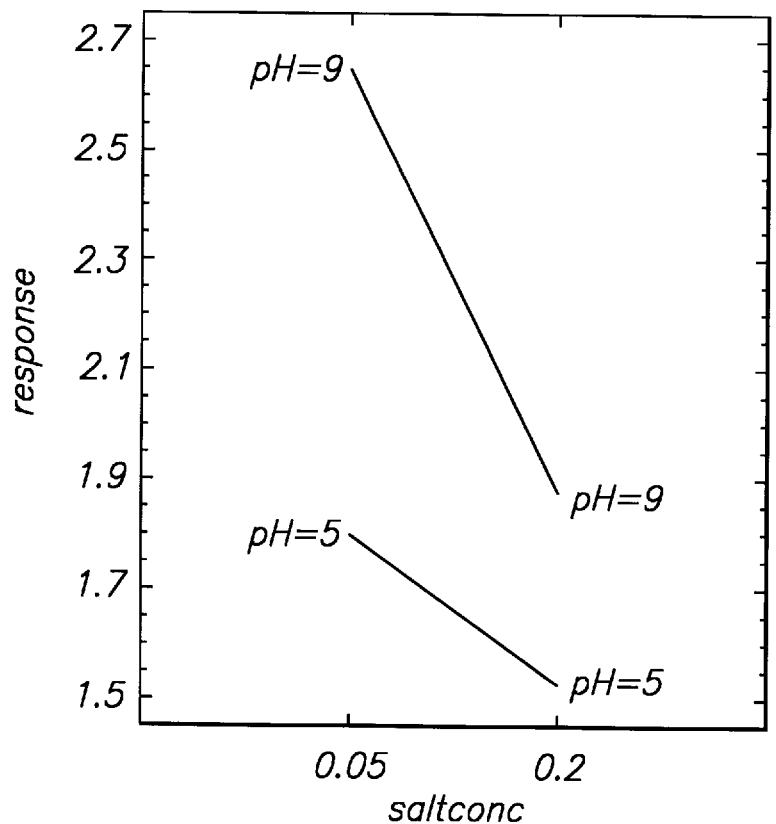

The sign in the denominator is plus for gels which collapse at lower temperature (see FIG. 4 and Example 9) and minus for gels which collapse at higher temperatures (see FIG. 3 and Examples 6 and 7).

Three osmotic pressures contribute to the total osmotic pressure of a gel, as shown below in equations 2, 3, 4 and 5.

$$\pi = \pi_{rubber} + \pi_{affinity} + \pi_{ion} \quad \text{(Equation 2)}$$

$$\pi_{rubber} = v_o kT\{\phi/2\phi_o) - (\phi/\phi_o)^{1/3}\} \quad \text{(Equation 3)}$$

$$\pi_{affinity} = v_o kT\{1n(1-\phi) + \phi\}\phi\Delta F(\phi/\phi_o)^2 \quad \text{(Equation 4)}$$

$$\pi_{ion} = v_o kT\{(\phi/\phi_o)\} \quad \text{(Equation 5)}$$

Here, $V_o$ denotes the number of effective crosslinks of the network when it is in the random walk configuration whose density is denoted by $\phi_o$. This state is referred to as the reference state. The rubber elasticity, $\pi_{rubber}$, which originates from the configurational entropy of the polymer network, provides a restoring pressure back to the reference polymer network density. When a polymer network is expanded, a negative pressure is created in the network and shrinks back. On the other hand, when it is contracted, the pressure acts to expand to the original reference state. Secondly, the polymer-polymer and polymer-solvent interactions give rise to another osmotic pressure, $\pi_{affinity}$. In a poor solvent, the polymer network tends to shrink, whereas in a good solvent a gel tends to swell. The last factor is the osmotic pressure due to ionization of the polymer network, $\pi_{ion}$. The counter-ions within the gel create a gas-type pressure to expand the gel in proportion to the density of counter-ions as well as the absolute temperature, kT, where k is the Boltzmann constant.

These three osmotic pressures compete with each other and the gel volume is equilibrated in a condition at which these three osmotic pressures balance at $\pi=0$. There is a special condition at which the competing pressures become equal to each other, at which point the volume change occurs. When the ionization pressure is large, as in the case of extensively ionized gels, the volume change is physically dramatic and discontinuous. With increased ionization, the volume change becomes large. There exists a minimum critical concentration of ionic component within a gel sorbent for each solvent system employed in order to achieve reversible discontinuous volume change of the gel sorbent. This minimum ionic concentration can be determined for each polymer network and solvent system.

The equations above qualitatively explain all of these aspects of volumetric changes. See T. Tanaka, D. J. Fillmore, S-T. Sun, I. Nihio, G. A. Swislow, and A. Shar, *Phys. Rev. Letters,* 45 1636 (1980) and U.S. Pat. No. 5,100,933 (Tanaka et al.), incorporated herein by reference. See also, S. H. Gehrke, *Adv. Polymer Science* 110:81–144 (1993), for other theoretical descriptions.

Persons having ordinary skill in the art may readily test whether any particular polymer network is responsive by following the procedures, and using the apparatus described in Example 6 to measure the volumetric change of the network as a function of, for instance, temperature, solvent concentration, pH and the like.

V. Methods of Preparing Polymer Networks

A. General Considerations

Many techniques may be used to make the polymer networks of the present invention.

A general protocol for forming a KATP polymer network of the present invention using a crosslinkable polymer includes the steps of dissolving the KATP polymer(s) in a suitable solvent and allowing the polymer(s) and solvent to mix. A crosslinking agent is then added to the polymer solution and the solution and crosslinker are further mixed together. The resulting solution may be poured into a solid mold (e.g., between two glass plates) and the crosslinking reaction carried out. In one sequence, a chemical crosslinking reaction is carried out in the homogenous polymer state at room temperature to form a certain amount of polymer network. Total crosslinking time will vary but is generally less than 24 hours. The network is then removed from its mold, and repeatedly washed to leach out any leachable material present in the network. In principle, a polymer network can be made from any KATP polymer with side groups that can react with a di- or multi-functional crosslinking molecule.

The polymer solution may also be formed into beads or spheres using crosslinking in a non-solid mold where the reacting solution (polymer, crosslinker and catalyst, if needed) is dispersed in a non-solvent to form a droplet. The solution reacts within the droplet to form a bead. In this method, the non-solvent may be considered to be a "mold" for polymer network droplets.

U.S. Pat. No. 3,208,994 to Flodin et al., incorporated herein by reference, generally discloses methods of preparing polysaccharide gel beads using suspension crosslinking. One introduces a water soluble polysaccharide and crosslinker into a suspension medium tinder agitation to obtain suspended drops of the polysaccharide solution. Another method of preparing gel beads uses inverse emulsion polymerization, in which a monomer solution is introduced into a dispersion solvent to form monomer droplets and polymerization is initiated to form polymer gel beads. See, Hirose et al. *Macromolecules* 20, 1342-4 (1987), incorporated herein by reference. Preferably, an aqueous cellulose ether solution, a non-polar saturated hydrocarbon solvent, and a crosslinker are provided and admixed to form a two-phase system. The two-phase system is agitated sufficiently to form droplets of aqueous cellulose ether solution in the two-phase system. The agitation of the two-phase system is maintained to form crosslinked cellulose ether gel beads and the crosslinked cellulose ether gel beads are thereafter recovered from the two-phase system.

Polymer networks of the invention also may consist, in whole or in part, of polymers made by copolymeiization/ crosslinking of monofunctional and polyftinctional polymerizable monomers.

A preferred method for making KATP gels from cellulose ethers involve dissolving a sample of cellulose ether such as HPC or HPMC in an anhydrous solvent that does not contain active hydrogen, such as for example N-methyl pyrolidone (21 C.F.R. 176.300), dimethylsulfoxide (DMSO), dimethylformamide (DMF), and the like. The concentration of polymer in the solution may range from about 5–20% by weight of polymer per volume of solution, with a preferred concentration primarily a function of the kind of polymer used in the synthesis. The molecular weight of the cellulose ether should be at least about 20,000. Preferred molecular weights range from about 75,000 to about 150,000. The higher the molecular weight of the polymer, the sharper will be the volume change of the resulting responsive gel. This is because a higher molecular weight will result in formation of a more consistent three-dimensional polymer network. Molecular weights may range up to 1,000,000 or more although it will be understood that viscosity effects will place an upper limit on the molecular weight of the polymer starting material. Those having ordinary skill in the art may readily determine using the methods described herein the extent to which viscosity constraints interfere with the gel formation process and/or prevent the crosslinker from mixing with the polymer.

When synthesizing gels of the invention with a crosslinker reagent that is a dicarboxylic acid, azeotropic distillation is a preferred method. A first solvent such as DMSO is added to a distillation flask containing the polymer and crosslinker reagents. Both are mixed to achieve a clear solution. To this solution, a small amount (several hundred $\mu$L) of an acidified solution of first solvent is added, followed by the addition of a second solvent (e.g.,toluene). This solution is allowed to react under azeotropic distillation until a gel forms in the flask. The gel is then removed and placed in an excess of deionized water. The water is removed and excess primary alcohol, (e.g., methanol) is added to remove excess solvent. The gel is washed and then dried in a desiccator.

Synthesis of KATP gels using acyl halide derivatives of dicarboxylic acids generally occurs as follows: while stirring the cellulose ether polymer solution under anhydrous conditions, the solution is cooled slightly below room temperature (in some embodiments to between about 10–20 degrees C.) and a cold solution (in some embodiments between about 2–8 degrees C.) of a preferred acyl halide derivative of a multifunctional carboxylic acid is added as crosslinker to the polymer solution. This solution is stirred and then allowed to sit until gelation has occurred. Gelation time will necessarily vary and may occur within about 2 hours (e.g., for HPC) or as long as 24 hours (e.g., for HPMC). The polymer/crosslinker weight ratio is between about 12/1 and 8/1. The lower the ratio, the more highly crosslinked will be the resulting gel.

The reaction will not always produce polymer/ crosslinker/polymer covalent couplings and a number of incomplete crosslinks will occur that will leave one end of the acid chloride group unreacted. After the crosslinking reaction, any unreacted acid chloride is quantitatively reacted with water to produce a carboxylic acid group. Carboxylic acid groups in the polymer network will provide a pH and temperature responsive gel (See Example 6).

Alternatively, if it is desired to produce a gel which has basic (amine) groups rather than acid groups, this may be achieved for example by allowing the acyl halide, cellulose ether reaction product to react with a KATP diamine such as ethylenediamine or hexamethylenediamine (21 C.F.R. 175.300 (b) (3) (xxxii) to produce an amine-terminated amide. The amine-terminated amide will survive the workup. These amine groups will cause the gel to be pH and temperature responsive in a range different from the acid group-containing gel.

After the gel is formed, destruction of any remaining acid chloride groups is carried out by soaking the gel in distilled water for about 12 hours. Solvent is then removed by soaking the gel in an alcohol (e.g., methanol, ethanol and the like) for at least several hours so that the methanol can diffuse into the gel and the solvent can diffuse out of the gel. After several hours, the wash is drained off. This process is repeated at least 4–5 times. The gel is then washed 4–5 times with distilled water while it is being heated to between about 60-80 degrees C. for about 2 hours. Heating drives off any remaining alcohol, leaving gel and water. The process is repeated at least 3–5 times until the gel appears opaque at the elevated temperature. This opacity signifies that the gel has undergone a volumetric change at a lower critical solution temperature (LCST) and is therefore has temperature responsive characteristics. For HPC, the LCST is between 42 and 46 degrees C. The degree of responsiveness to pH may be assayed using the device and procedures given in Example 6. In the Examples, all the gels were pH responsive and all gels except that of Examples 8, 11–16 were also temperature responsive.

Persons having ordinary skill in the art may readily determine if a particular KATP polymer material is capable of forming a polymer gel network by following the synthesis procedures described herein. Moreover, methods to determine the degree of crosslinking are conventional and are described, for example, in "Hydrogels in Medicine and Pharmacy", N. A. Peppas and B. D.Barr-Howell (eds), Vol. 1, CRC Press, Boca Raton, Fla. (1986). The degree of crosslinking of polymer gels may also be measured by uniaxial compression tests. Briefly, a cylindrical gel disk (approximately 25 mm in diameter) is first swollen to equilibrium in water at 25° C. and weight, thickness, and diameter measured using a balance, micrometer, and a ruler, respectively. The gel sample is placed in a water-filled Petri dish and a constant strain applied by adjustment of a micrometer. The relaxation of the applied stress was monitored by computer until the equilibrium, relaxed state was reached. Then the strain is increased in steps and equilibrium value of stress at each point recorded. Next, the equilibrium stress is plotted versus the strain function ($\alpha - \alpha^{-2}$) where $\alpha$ is the ratio of deformed thickness to the unstrained thickness of the sample. This plot is expected to be linear for $\alpha > 0.90$. The shear modulus is obtained from the slope of the initial linear region of the plot using the equations of Mark, *Physical Properties of Polymers*, Am. Chem. Soc., Wash. D.C.,(1984), incorporated herein by reference. The crosslink density of the gel sample is calculated from the equations derived by Harsh et al., *J. Control Release*, 1991, for non-porous gels, incorporated herein by reference, e.g.

$$G = RT \rho x \ (\phi 2f/\phi 2)^{2/3}$$

where:
$\rho x$ is the crosslink density;
$\phi 2f$ is the polymer volume fraction at the network formation; and
$\phi 2$ is the polymer volume fraction of the gel during the experiment.

B. Microporous Gels

Microporous KATP gels are encompassed by the invention. A gas phase is dispersed throughout a fluid polymer phase and the resulting porous material is solidified. In such microporous materials, the cell or pore size is generally of the order of 100–200 microns or larger. See Aubert et al., *Macromolecules,* 21: 3468 (1988), incorporated herein by reference.

Another method for fabricating microporous gels is to disperse solid particles in a polymer melt or in a polymer solution. The polymer solution or melt is solidified either by chemical crosslinking or by physical means such as freezing. After solidification of the polymer, the solid particles are leached away. See Mikos et al, *Mater. Res. Soc. Symp. Proc.,* 252, pp. 353–358 1992., incorporated herein by reference.

Microporous gels may also be formed by a process in which co-monomers including crosslinker are polymerized in one phase of a bicontinuous microemulsion, while the other phase forms the cells or pores. See Hainey, et al., *Macromolecules,* 24: 117–121 (1991), incorporated herein by reference. Materials made by this process have a pore size ranging from 1–30 microns. This technique is limited by the ability to find a suitable solvent and non-solvent for the comonomers and emulsifying agent which will form a bicontinuous emulsion.

A preferred process for making microporous gels of the present invention and for developing design controls that regulate the microstructure of the final product, is the phase inversion process. "Phase inversion", hereinafter called "phase separation", refers to the process by which a polymer solution containing one or more polymer precursors, in which the solvent is the continuous phase, inverts into a three- dimensional network or gel where the polymer(s) are now the continuous phase. Phase separation occurs when polymer becomes insoluble in the solvent upon changing the system conditions. See Kesting, "Synthetic Polymeric Membranes: A Structural Perspective", J. Wiley and Sons, NY, 1985, incorporated herein by reference. Thus, one method of the invention includes contacting a dissolved polymer with another solvent that effectively removes the solvent from the polymer and precipitates the polymer out of solution, forming a microporous interconnected structure that is crosslinked to convert it into a responsive gel.

Most preferred are methods in which temperature induces phase separation. These processes use a substance that is a good solvent for the polymer at one temperature, but is a poor solvent at another temperature. Temperature may be easily controlled so that this method generally is reproducible, since heat transfer is much faster than mass transfer.

A preferred method described herein for making microporous volume change gels can be applied to make crosslinked microporous gels from any crosslinkable polymer-solvent system which phase separates with changes in temperature. Many aqueous-soluble polymers phase separate with changes in temperature. Even aqueous polymer solutions which don't phase separate at a particular temperature can be forced to phase separate at another temperature by adding, for example, an organic solvent such as ethanol or a suitable salt, such as for example 1M NaCl.

Microporous gels may be "fast response" gels. As defined herein, "fast response" means that the gel reaches 90% of its maximum volumetric swelling or 90% of its minimum volumetric collapse in a time that is at least ten times faster than a comparable non-porous gel of the same geometry when both gels are subjected to a similar change in an environmental condition. Methods of making and using fast response gels may be found in co-pending PCT application number PCT/US94/05400, filed 13 May 1994 now U.S. Ser. No. 08/737,404 (35 U.S.C. Section 371(c) (2): "Microporous Fast Response Gels and Methods of Use"- Gehrke and Kabra).

VI. Loading Biologically Active Solutes into Polymer Gel Networks

It will be understood that there are many methods available to load biologically active solutes into a polymer gel. Two general methods of drug loading into gels have been used: (i) formation of a hydrogel in the presence of the solute (i.e., drug); and (ii) swelling of a preformed gel in a solution (i.e, an organic solvent) of the solute (i.e., drug). See, for example, Kim et al., *Phar. Res.* 9: 283–289 (1992). Loading are generally on the order of about 3 percent by weight.

Gref et al., *Science,* 263: 1600–1602 (1994) have developed biodegradable nanospheres using amphiphilic polymers that phase-separated during emulsification. Up to 45 percent by weight of drug loading was achieved by dissolving the drug in the same organic solvent that dissolved the copolymer. Although drug loading is high using this method, the drug must be dissolved in an organic solvent.

Recently, principles for isolating and purifying proteins from solution by sorption into a crosslinked polymer gel phase have been derived, the sorption driven by addition of a substantially immiscible, second polymer phase to the protein solution. Gehrke et al., *Biotechnol. Progr.*, 7: 355–358 (1991), incorporated herein by reference. This method, also called "solution-controlled gel sorption", is based, in part, on the discovery that the general principles of two-phase aqueous extraction used for purifying proteins can be extended to be used in which one of the phases is a crosslinked gel. In two-phase aqueous extraction methods of protein purification, a protein is made to partition selectively into one of two immiscible aqueous polymer solution phases which are in contact with each other.

In particular, high loadings of solutes into gels may be obtained with solution controlled gel sorption using a second, loading polymer phase. In the presence of a salt solution, the second loading polymer and salt have a synergistic effect which causes partitioning and sorption (exceeding 20% by weight) of the solute into the polymer gel. The second loading polymer need not be a gel but is most preferably soluble in the same solvent that is the gel's solvent.

This is the methodology used herein for loading a solute into a crosslinked gel.

This partitioning behavior is governed by properties such as molecular weight of the polymers, the type and concentration of salts and the relative hydrophobicity/hydrophilicity of the solute. Differences in the various interaction energies between the solute and the different polymers leads to a partition coefficient (concentration of solute in the gel/concentration of the solute in the second loading polymer) greater than one (i.e., preferential loading by the gel) or less than one (i.e., preferential loading by the second loading polymer).

The general method used for solute loading into a crosslinked gel phase is briefly as follows:

Crosslinked gels are pre-equilibrated with solute-free, loading polymer solutions. The equilibrated gels are then separated from the loading polymer solution. To each gel, a solution with the same loading polymer concentration as the pre- swelling solution but including a solute and a salt is added. The tube is then agitated to mix gel and salt/solute solution. Equilibrium is reached in less than 15 minutes, (see Gehrke et al., 1991, supra) and the gel separated from the remaining solution. The solute concentration in the second, loading polymer phase may be determined by a variety of methods, depending upon the solute of interest. For spectrophotometric assays, light absorbance is measured at 280 nm for proteins; at 630 nm for blue dextran; and at 520 nm for Vitamin B12 with a UV/VIS spectrophotometer. The concentration of solute in the gel phase is determined by a mass balance.

Cellulose ethers are advantageous for loading by this method. Because the degree of substitution of the anhydroglucose unit has a great effect on the degree of hydrophilicity, cellulose ethers differ in their hydrophilic nature. There are a number of immiscible polymer gels that are mainly water and that are close to each other on a spectrum of relative hydrophobicity-hydrophilicity. This means that phase systems formed by these polymers, including cellulose ethers, can be expected to be selective in separating substances which themselves are mainly water; that is substances that fall within the same part of the solvent spectrum. Examples are particles and macromolecules of biological origin. Aqueous solutions of the following polymers are mutually immiscible and are ranked in order of increasing hydrophobicity: dextran sulfate, carboxymethyl dextran, dextran, hydroxypropyldextran, methylcellulose, hydroxypropylcellulose, polyvinylalcohol, polyethylene glycol and polypropylene glycol.

Solute is recovered from the loaded polymer as follows: Solute is chosen to have a very low partition coefficient in pure buffer, lacking any polymer. The solute contained in the loaded gel after the partitioning experiment is recovered by adding pure buffer lacking any to the loaded gel. The gel is separated by centrifugation from any supernatant and the concentration of the solute in the supernatant measured using a spectrophotometer. This procedure is repeated until the solute concentration in the supernatant is negligible.

With a reversibly responsive gel, solute recovery is accomplished by causing the gel to undergo to volumetric collapse using established methods. See, for example, Cussler, U.S. Pat. No. 4,555,344, incorporated herein by reference.

VII. Biologically Active Solutes

The biologically active solutes that may be loaded into the polymer networks of the present invention are any substance having biological activity, including proteins, polypeptides, polynucleotides, nucleoproteins, polysaccharides, glycoproteins, lipoproteins, and synthetic and biologically engineered analogs thereof.

Examples of biologically active solutes that might be utilized in a delivery application of the invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C.F.R. 330.5, 331 through 361; 440–460; drugs for veterinary use listed by the FDA under 21 C.F.R. 500–582, incorporated herein by reference, are all considered acceptable for use in the present novel polymer networks.

Drugs that are not themselves liquid at body temperature can be incorporated into polymers, particularly gels. Moreover, peptides and proteins which may normally be lysed by tissue-activated enzymes such as peptidases, can be passively protected in gels as well.

The term, "biologically active solute" includes pharmacologically active substances that produce a local or systemic effect in animals, plants, or viruses. The term thus means any substance intended for use in the diagnosis, cure, mitigation, treatment or prevention of disease or in the enhancement of desirable physical or mental development and conditions in an animal, plant, or virus. The term "animal" used herein is taken to mean mammals such as primates, including humans, sheep, horses, cattle, pigs, dogs, cats, rats, mice; birds, reptiles, fish, insects, arachnids and protists (e.g., protozoa) and prokaryotic bacteria. The term "plant" means higher plants (angiosperms, gymnosperms), fungi, and prokaryotic blue-green "algae" (i.e., cyanobacteria).

The biologically active solute may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic. Examples of proteins include antibodies, enzymes, steroids, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules.

Classes of biologically active solutes which can be loaded into crosslinked gels using the methods of this invention include, but are not limited to, anti-AIDS substances, anti-cancer substances, antibiotics, immunosuppressants (e.g., cyclosporin) anti-viral substances, enzyme inhibitors, neurotoxins, opioids, hypnotics, antihistamines, tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, anti-pyretics and anti-inflammatory agents such as NSAID'S, local anesthetics, ophthalmics, prostaglandins, anti-depressants, anti-psychotic substances, anti-emetics, imaging agents, specific targeting agents, neurotransmitters, proteins and cell response modifiers.

A more complete listing of classes of solutes suitable for loading into polymers using the present methods may be found in the *Pharmazeutische Wirkstoffe*, ed. A. Von Kleemann and J. Engel, Georg Thieme Verlag., Stuttgart/New York, 1987, incorporated herein by reference.

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir( ), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms.

Examples of antibiotics include penicillin, tetracycline, chloramphenicol, minocycline, doxycycline, vanomycin, bacitracin, kanamycin, neomycin, gentamycin, erythromicin and cephalosporins.

Anti-viral agents are substances capable of destroying or suppressing the replication of vinises. Examples of anti-viral agents include a-methyl-P-adamantane methylamine, 1,-D-ribofuranosyl-1,2,4-triazole-3 carboxamide, 9-[2-hydroxyethoxy]methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(alpha-diethylaminopropionyl)- phenothiazine hydrochloride, calmidazolium chloride, hemicholinium-3,3, 5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine HCl, hydralazine HCl, clorgyline HCl, deprenyl HCl,L(-)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1 -methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate, S (-)-, 3-iodotyrosine, alpha-methyltyrosine, L-, alpha -methyltyrosine,D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1 -methyl-4-phenyl-2,3- dihydropyridinium perchlorate, N-methyl-4-phenyl- 1,2,5,6-tetrahydropyridine HCl, 1-methyl-4-phenylpyridinium iodide.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include norbinaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, and the like.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, Chk and ethosuximide.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds include betaxalol, pilocarpine, timolol, and combinations of timolol and its salts with pilocarpine.

Anti-parasitic, -protozoal and -fungals include ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are ail recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (pDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor and bone growth/cartilage-inducing factor (alpha and beta).

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

VIII. Utilities/Formulations

Polymer networks of the present invention have a wide variety of uses.

A number of applications for the responsive gels of the invention are listed in Gel Science, Inc. brochures "Gel Sciences, the leader in Engineered Response Gels", G001-2/94-10M; "Separations", S001-2/94-10M, and "Controlled Release", CR001-2/94-10M, which are included herein by reference. These applications include: 1) Separations, or reduction in the solvent level, of water or reduction in the water level of a number of products including protein, food protein, other food components; 2) Medical, pharmaceutical and diagnostic applications including electrophoresis, iontophoresis, free drug assay, spinal fluid diagnostics, assay, blood ultracentrifugation, cell culturing, wound dressing, exudate absorption and bacterial indicators; and 3) Toys, in which the toy needs to be biologically inert and safe.

In food separations or pharmaceuticals, responsive gels of the present invention may be used to selectively incorporate a solvent from a solute or separate a protein (or a drug or other solute) from a solution. The polymer networks of the invention are thus generally applicable to any process of selectively excluding a solute from a solvent by selectively incorporating the solvent. The term "selectively incorporating" refers to procedures whereby all, or a portion of a low molecular weight solvent (e.g., water) is selectively removed by a polymer network from a solution of a higher molecular weight solute (e.g., synthetic or natural polymers, organic compounds, proteins, suspended particles and the like). The term "high molecular weight solute" refers to solutes having a molecular weight of at least about 250. Solvent/solute systems that may be utilized in the present invention include systems in which solute is dissolved and those in which solute is dispersed or suspended in solution. The polymer gel network does not necessarily incorporate the solute if the solute is large enough. The fluid remaining after sorption is concentrated with solute and may be removed.

A preferred separations process functions by first contacting a solvent and solute with a polymer gel network of the invention capable of selective incorporation of the solvent. The gel physically expands as the entire gel, or a sorptive component thereof, accumulates solvent within the interior of the gel. At least part of the solvent is thereby incorporated by the gel, but solute is excluded from entering the gel. After expansion of the gel, the concentrated solute external to the swollen gel is separated from the swollen gel by centrifugation, filtration, or other conventional methods. The expanded gel may be discarded. The gel may also be collapsed such that solvent is released. This "regeneration" step is preferred so that the solvent-incorporating polymer gel is returned to a condition where it is again available to selectively accumulate solvent. See Cussler, U.S. Pat. No. 4,555,344, incorporated herein by reference. Polymer gels used in this method may be expanded by either (i) contacting a gel with a solvent containing a solute and allowing the gel to non-reversibly swell and selectively incorporate the solvent; (ii) initiating a reversible volumetric expansion of the gel to selectively incorporate solvent by triggering the expansion with a stimulus; or (iii) a combination of (i) and (ii).

Expansion is particularly advantageous and energy efficient for initiating selective incorporation when a convenient environmental trigger is available. Solvent incorporated by polymer gels can preferably be disgorged by initiating a volumetric gel collapse. In preferred embodiments of the invention, therefore, a solvent-containing polymer gel of the invention is challenged with an environmental change (e.g., pH: see Example 6) and the environmental change affects the gel by causing the entire gel, or a component thereof, to undergo a collapse. The collapsed polymer gel can then be separated from the disgorged solvent by, for example, filtration and/or centrifugation. Reversible collapse of the polymer gels is particularly useful for regenerating the gel because, after the polymer gel is collapsed, it may be re-expanded. The solvent released during this regeneration may be recycled from the system or discharged as waste solvent.

In an analogous manner, responsive gels of the present invention may be used to selectively incorporate a solute from a solvent to separate a protein (or a drug or other solute) from a solution. The polymer networks of the invention are thus generally applicable to any process of selectively excluding a solute from a solvent by selectively incorporating the solute. A preferred separations process functions by first contacting a solvent and solute with a polymer gel network of the invention capable of selective incorporation of the solute. Typically, the gel will contain an immobilized ligand that will form a binding pair with the solute of choice. The gel physically expands as the entire gel, or a sorptive component thereof, accumulates and binds solute within the interior of the gel. At least part of the solute is thereby incorporated by the gel. After expansion of the gel, the concentrated solvent external to the swollen gel is separated from the swollen gel by centrifugation, filtration, or other conventional methods.

Drug delivery from acrylate-based hydrogels has been described by Kou et al., *J. Control Release*, 12: 241–250 (1990). In one embodiment of the present drug delivery method, a KATP responsive gel is loaded with a biologically active compound at one temperature and induced to undergo a volumetric collapse to disgorge the entrained biologically active compound at another temperature. Delivery of the compound may be modulated by a temperature higher than the temperature of the gel in its loading mode (See Gutowska et al., *J. Control Release*, 22: 95–104 (1992)- using NIPA to release heparin at high temperature).

Polymer gels of the present invention incorporating, for example, a medicament like hyaluronic acid, may be incorporated into a bandage, gauze or other conventional wound dressing. Upon activation by an appropriate environmental trigger such as a temperature change or a change in the energy of incident light, the gel collapses and disgorges the entrained medicament to the wound environment. If the gel is triggered to expand and release the medicament, it may also incorporate wound exudates during the expansion. See, for example, U. S. Pat. No. 4,659,700, incorporated herein by reference.

In another embodiment, a microporous KATP responsive gel is loaded with a biologically active compound at one temperature and induced to undergo a volumetric expansion at another temperature to allow fluid from the environinent of use (e.g., blood, lymph) to enter the expanded gel and biologically active compound to exit the expanded gel via diffusion through the pores. In a preferred drug delivery embodiment, the gel expands to release a drug during exposure to pH conditions that are different than the pH conditions to which it is exposed in the loading mode. Without wishing to be bound by any theory, a cellulose ether gel such as HPC with an LCST near body temperature (e.g., 42° C.) should have its LCST shifted to a lower temperature at lower pH. This is because very few —COOH and/or —OH groups are ionized at low pH and the gel would tend to have a reduced hydrophilicity. At higher pH, many —COOH and/or —OH groups will be ionized and the LCST is shifted to a higher temperature due to increased hydrophilicity. Around body temperature, the gel is therefore very sensitive to pH change and would be collapsed at low pH (i.e., that of the stomach, where the drug would be retained within the polymer network) and expanded at higher pH (i.e., that of the intestine, where the polymer gel network would expand and release the drug). A responsive gel may be made from starting materials (i.e., cellulose ethers of various configurations) that vary in their hydrophobic/hydrophilic nature when ionized, so that the methods described herein may be used to make a reversibly responsive, pH-sensitive gel with an LCST designed to match the body temperature of a desired subject. The LCST of preferred cellulose ethers is well known and can be easily determined and verified. Exemplary LCST's (degrees C.) are 49° (MEC); 42°–46° (HPC); 59° (methyl (hydroxypropyl)cellulose: HPMC); 60° methyl (hydroxyethyl)cellulose; and 55°–70° (ethyl(hydroxyethyl) cellulose).

In another method of interest, immobilization and protection of a catalyst such as an enzyme within a responsive KATP gel enables the immobilized enzyme to be active and effective in environmental conditions in which the gel is expanded (See Example 6). Changing the environment (e.g., lowering pH) shrinks the gel and inactivates the enzyme by shutting off accessibility of the reactants in the solution to the catalyst.

In another method of interest, ligands that scavenge lipids are attached to KATP gels of the invention and are used to reduce the level of undesirable lipids present in the gastrointestinal tract of an animal. KATP cellulose ethers containing multiple reactive hydroxyl groups are particularly suitable for this purpose since the ligands may be bound thereto via stable ether linkages. Ligands for scavenging lipids are generally hydrophobic, capable of being attached to the polymer gel and may range from 1 to about 50% of ligand groups relative to the polymer. They are exemplified by straight chain aliphatics between $C_{12}$ and $C_{24}$, as well as cholesterol itself. Hydroxyl groups of ligands may be converted to epoxy groups for reaction with KATP cellulose ether polymers of the invention. Depending on the particular ligand chosen, lipids which can be removed include cholesterol, cholesterol esters, steroids, fat soluble drugs, fatty acids and fatty acid esters. See Nightingale and Hoffman, Future Perspectives of Biomedical Polymers, Dec. 4–6, 1992, Maui, Hi. Iontophoretic devices made of KATP polymers are also within the scope of the invention. Iontophoretic function of a KATP polymer gel network of the invention may conveniently be studied in vitro in a commercially available Franz-type transport cell. A KATP polymer gel of the invention is loaded with a drug according to any procedure, preferably those described herein. The loaded gel is placed in the reservoir of a well type electrode. The upper (donor) portion of the cell is separated from the buffer-filled bottom (receptor) portion by a membrane (e.g., porcine skin or a synthetic membrane). In a typical protocol, current is applied to the anode which drives the positively charged drug through the membrane into the receptor solution. The amount of drug in the receptor solution is assayed using, for example, HPLC. See, for example, U.S. Pat. No. 4,141,359, incorporated herein by reference.

Electrodes and other monitoring instruments may have polymer gels of the present invention incorporated within or on the electrode. The gel may have materials such as ligands, enzymes, and the like, immobilized in or on the gel network. See, for example, U.S. Pat. No. 4,274,420, incorporated herein by reference.

Polymer networks and biologically active solutes that are incorporated in, or on, the network may be used in pharmaceutically-effective amounts, with or without a compatible carrier. The term "carrier" includes any liquid, gel, fluid, ointment, cream, lotion or the like, which is suitable for use in, or on a subject and which does not interact with the other components of the polymer network in a deleterious manner. The term "compatible", as used herein, means that the components of the pharmaceutical compositions are capable of being commingled with the polymer network of the present invention, and with each other, in a manner such that there is no interaction which would substantially reduce the pharmaceutical efficacy of the pharmaceutical. A "pharmaceutically-effective amount" of a biologically active material or polymer network containing the material is that amount which produces a result or exerts an influence on the particular condition being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such a peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogen-free water; isotonic saline; phosphate buffer solutions; cocoa butter (suppository base); emulsifiers, such as the Tweens [Registered ™]; as well as other non-toxic compatible substances used in pharmaceutical formulations. Wetting agents and lubricants such as sodium lauryl sulfate, as well as coloring agents, flavoring agents, excipients, tableting agents, stabilizers, antimicrobials, antioxidants, and preservatives, can also be present. Other compatible pharmaceutical additives and actives (e.g., NSAID's; pain killers; muscle relaxants) may be included in the pharmaceutically-acceptable carrier for use in the compositions of the present invention. For example, local anesthetics (e.g., benzyl alcohol; lidocaine) may be included in the pharmaceutically-acceptable carrier. Adhesive formulations may also be incorporated into the polymer gels of the invention. Exemplary adhesive devices are described in U.S. Pat. Nos. 3,972,995 and 4,593,053, incorporated herein by reference.

The formulations include, but are not limited to, those suitable for oral, buccal, rectal, topical, nasal, ophthalmic (for example, see U.S. Pat. No. 2,976,576 to a contact lens composition, incorporated herein by reference) or parenteral (including subcutaneous, intramuscular and intravenous) administration, all of which may be used as routes of administration for practicing the present invention. Other suitable routes of administration include intrathecal administration directly into spinal fluid (CSF), direct injection onto an arterial surface to prevent re-stenosis, and intraparenchymal injection directly into targeted areas of an organ.

Formulations of the present invention suitable for oral administration may be presented as discrete units such as capsules, cachets, tablets or lozenges, each containing a predetermined amount of the potentiating agent as a powder or granules; as liposomes containing a loaded gel; or as a suspension in an aqueous liquor or non-aqueous liquid such as a syrup, an elixir, an emulsion or a draught.

Formulations suitable for parenteral administration conveniently may comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations can be prepared by a similar method to the nasal spray, except that the pH and isotonic factors are preferably adjusted to match that of the eye.

In addition to the aforementioned ingredients, the formulations of this invention may further include one or more accessory ingredient(s) selected from diluents, buffers, biocides (e.g., chlorhexidine gluconate, triclosan, povidine-iodine, and the like), adhesives (e.g., lectin, pectin, fibronectin, and the like), flavoring agents, binders, antimicrobials, skin permeation enhancers, disintegrants, surface active agents, thickeners, lubricants, preservatives (including antioxidants), surfactants, and the like.

The pharmaceutical compositions may be in the form of a sterile injectable aqueous or oleaginous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectibles.

The KATP polymer gels of the present invention may be fabricated into a cosmetic compositions by combining the gel with fragrance or other cosmetic material and incorporate the gel into a cosmetic carrier. The cosmetic carrier may take the form of fatty or nonfatty creams, milky suspensions or emulsion-in-oil or oil-in-water types, lotions, gels or jellies, colloidal or noncolloidal aqueous or oily solutions, pastes, aerosols, soluble tablets or sticks. Generally, the carrier contains from about 0.001% to about 10% by weight of the gel of the invention. Preferred ranges are about 0.1% to about 10%.

Cosmetic compositions according to the invention may also combined with surface active agents of the anionic, cationic or nonionic type, emulsifying agents, perfumes, solvents, fats, oils and mineral wax, fatty acids and derivatives thereof alcohols and derivatives thereof, glycols and derivatives thereof, glycerol and derivatives thereof, lanolin, beeswax, oleic acid, spermaceti, almond oil, castor oil, sorbitol and derivatives thereof, tragancanth gum, clay, magnesia, talc, metal stearates, chalk, magnesium carbonate, and the like. These materials are well-known in the cosmetic art and are discussed, for example, in Remington's *Pharmaceutical Science*, McCutcheon's *Detergents*, and Sagarin's *Science and Technology of Cosmetics*, all of which are incorporated herein by reference. Exemplary cosmetic compositions used according to the present invention are given in Example 17. The cosmetic compositions used in the method according to the invention may also contain agents such as antibiotics, anti-inflammatories or anaesthetics such as carbenicillin, chloramphenicol, gentamicin, penicillin G, polymyxin B, streptomycin, sulfacetamide, trifluridine, acyclovir, sulfadiazine, corticosteroids, nystatin, and miconazole.

The cosmetic compositions of the present invention may all contain various preservatives such as, butylated hydroxytoluene, methionine, cysteine, ascorbic acid, catalase, superoxide dismutase, glutathione, parabens and the like. The invention will now be illustrated with the following, non-limiting examples.

IX. Examples

EXAMPLE 6

Synthesis of pH and Temperature Sensitive Hydroxypropylcellulose Gel with Adipoyl Chloride Reagent Exactly 50 mL of N-methyl pyrolidone (Fisher Scientific, Catalog No. 03688-4) was added to 5 grams of hydroxypropylcellulose (Aqualon, Klucel 99-EF NF). The two materials were mixed on a magnetic stirrer for about 2 hours, while covered, to achieve a clear and colorless solution. This solution was then placed in a refrigerator for about 1 hour in order to achieve a solution temperature of 4°–8° C. To this solution, while stirring, 1 mL of cold (2°–8° C.) adipoyl chloride (Aldrich, Cat. No. 16,521-2) was added, and the resulting solution allowed to stir for 1 minute. A microcapillary pipette of about 340 $\mu$m bore (Fisher Scientific, Cat. No. 21-16A-2A) was dropped into the solution. A gel formed in and around the pipette in about 3 hours. The pipette was then removed from the gel and placed in a vessel containing an excess of deionized water (Millipore Alpha-Q). After about 8 hours the water was decanted off, and the vessel filled with methanol (ACS grade). The pipette containing the gel was allowed to sit in methanol solution for 5 hours. This was followed by three more, 5 hour methanol washes.

The pipette was mounted in an airspace of a small, clear capsule (about 5 cm×4cm×2cm). Temperature of the capsule was regulated by equilibrating it with well stirred, temperature controlled water solution.

A differential thermocouple arrangement permitted the monitoring of temperature differences between water and air within the capsule to about 0.005 deg. C. Water temperature within the capsule was measured to about 0.1 deg. C. with a digital thermocouple (mfg. by Cole-Parmer Scanning Thermocouple Thermometer #92800-00).

Two sealed containers were partially filled with pure, degassed distilled water. One container also contained a port to allow addition of acid; the second container contained a port for addition of base. Use of a single container to generate a wide range of pH values from acid to base would lead to formation of neutral salt, which might have induced a volume change in the gel. A series of pH solutions were made, as described below, and then pumped through the bore of the tube at a flow rate of 3 mL/min.

The diameter of the gel cylinder was observed at each pH and recorded through the optically clear walls of the capsule using a 10× microscope. Volumetric ratio changes of the gel with pH were determined by cubing the ratio of the gel string diameter to pipette bore.

The pH solution was changed every 0.5 pH units and maintained to let the gel reach equilibrium. Then, the volume of the gel was measured. Water temperatures differed by no more than 0.1 degree C. during the experiments and was maintained at 25 degrees C.

Low pH values were obtained by adding concentrated hydrochloric acid in increasing amounts to the pure, distilled water in one container. Above the pH value for pure, distilled water lacking any acid addition (pH 6), the second container was employed and sodium hydroxide (1N) was added. The pH was controlled by flowing dry nitrogen gas slowly through the headspace of each container to maintain a positive pressure and prevent entrance of ambient air into the container. The pH was orded continuously in each container by an Orion combination pH electrode (#91-56) immersed in the solution connected to an Orion #520 pH meter.

Figure 2:
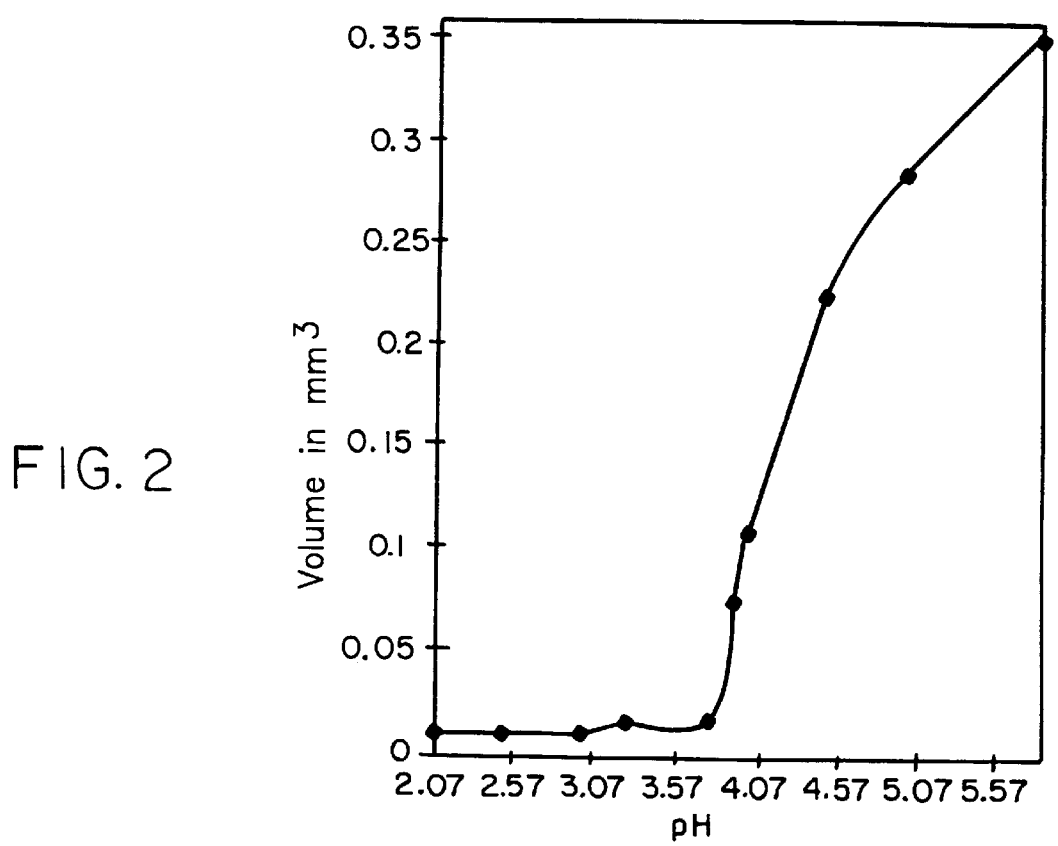
FIG. 2 is a pH-volume relationship for a crosslinked HPC gel of the invention.

This gel exhibited a volumetric dependency on pH illustrated in FIG. 2.

EXAMPLE 7

Preparation of Hydroxypropylmethylcellulose Gel with Adipoyl Chloride Reagent

Exactly 50 mL of N-Methyl Pyrolidone (Fisher Scientific, Catalog No. 03688-4) was added to 5 grams of hydroxypropylmethyl cellulose (Dow Chemical, Methocel E5 PREM), and was mixed for 2 hours at 45° C., while covered, to achieve a clear straw-colored solution. This solution was then placed in a refrigerator for 1 hour in order to achieve a solution temperature of 4°–8° C. To this solution, while stirring, 1 mL of cold (2°–8° C.) adipoyl chloride (Aldrich, Cat. No. 16,521-2) was added, and the resulting solution was allowed to stir for 1 minute. A gel formed in 12 hours. The gel was then removed, cut into 1×1×1 cm$^3$ cubes, and placed in an excess of deionized water (Millipore Alpha-Q). After 12 hours the water was decanted off, and the vessel was filled with an excess of Methanol (ACS grade), and the cubes were allowed to sit in methanol solution for 12 hours. This was followed by 3 more 12 hour washes. The cubes were then dried in a desiccator, and then swollen in deionized water. This gel was both pH and temperature sensitive.

EXAMPLE 8

Preparation of Starch Gel with Adipoyl Chloride Reagent

Exactly 50 mL of N-Methyl Pyrolidone (Fisher Scientific, Catalog No. 03688-4) was added to 5 grams of Modified Food Starch (National Starch, #6818:77-3), and was mixed for 2 hours at 45° C., while covered, to achieve a clear straw-colored solution. This solution was then placed in a refrigerator for 1 hour in order to achieve a solution temperature of 4°–8° C. To this solution, while stirring, 1 mL of cold (2°–8° C.) adipoyl chloride (Aldrich, Cat. No. 16,521-2) was added, and the resulting solution was allowed to stir for 1 minute. A gel formed in 12 hours. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water.

The pH responsiveness of this material was assayed by preparing the identical starch gel in pipettes according to the procedures of Example 6. The pH sensitivity was tested using the procedures and apparatus of Example 6 as well. FIG. 3 illustrates the sharp volume transition over a small change in pH (less than 0.5 pH units).

EXAMPLE 9

Preparation of pH and Temperature Sensitive HPC Hydrogel

Exactly 50 mL of N-Methyl Pyrolidone (Fisher Scientific, Catalog No. 03688-4) was added to 5 grains of Hydroxypropylcellulose (Aqualon, Klucel 99-EF NF), and was mixed for 2 hours at 45° C., while covered, to achieve a clear straw-colored solution. This solution was then placed in a refrigerator for 1 hour in order to achieve a solution temperature of 4°–8° C. To this solution, while stirring, 1 mL of cold (2°–8° C.) sebacoyl chloride (Aldrich, Cat. No. 13,178-4) was added, and the resulting solution was allowed to stir for 1 minute. A gel formed in 12 hours. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. The pH responsiveness of this material was assayed by preparing the identical gel in pipettes according to the procedures of Example 6. The pH sensitivity was tested using the procedures and apparatus of Example 6 as well.

EXAMPLE 10

Preparation of pH and Temperature Sensitive HPC Hydrogel

Exactly 50 mL of N-Methyl Pyrolidone (Fisher Scientific, Catalog No. 03688-4) was added to 5 grams of hydroxypropylcellulose (Aqualon, Klucel 99-EF NF) and was mixed for 2 hours at 45° C., while covered, to achieve a clear straw-colored solution. This solution was then placed in a refrigerator for 1 hour in order to achieve a solution temperature of 4°–8° C. To this solution, while stirring, 1 mL of cold (2°–8° C.) succinyl chloride (Aldrich, Cat. No. S645-2) was added, and the resulting solution was allowed to stir for 1 minute. A gel formed in 12 hours. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. The pH responsiveness of this material was assayed by preparing the identical gel in pipettes according to the procedures of Example 6. The pH sensitivity was tested using the procedures and apparatus of Example 6 as well.

EXAMPLE 11

Preparation of Hydroxyethylcellulose Gel with Adipic Acid Reagent

Exactly, 45 mL of DMSO (Fisher Scientific, Catalog No. 03688-4) was added to a distillation flask containing 5 grains of hydroxyethylcellulose (Aqualon, Natrosol 99–250HBR PA) and 2 grams of adipic acid (Fisher Scientific, Catalog No. A44–500), and was mixed for 2 hours, while covered, to achieve a clear colorless solution. To this solution, 5 mL of toluene (Fisher Scientific), solution was added. This was followed by the addition of 500 μL of a 50% (v/v) solution of $H_2SO_4$ in DMSO. This solution was allowed to react under azeotropic distillation (see Haslam, *Tetrahedron* 36, (1980), 2409–2433, incorporated herein by reference). After 12 hours, a gel formed in the flask. The gel was then removed, cut into 1×1×1 cm$^3$ cubes, and placed in excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. This gel is not temperature sensitive but is pH sensitive.

EXAMPLE 12

Preparation of Hydroxyethylcellulose Gel with Citric Acid Reagent

Exactly 45 mL of DMSO (Fisher Scientific, Catalog No. 03688-4) was added to a distillation flask containing 5 grams of hydroxyethylcellulose (Aqualon, Natrosol 99-25OHBR PA) and 2 grams of citric acid (Aldrich Chemical, Cat. No. 25,127-5), and was mixed for 2 hours, while covered, to achieve a clear colorless solution. To this solution, 5 mL of toluene solution was added, followed by the addition of 500 μL of a 50% (v/v) solution of $H_2SO_4$ in DMSO. This solution was allowed to react under azeotropic distillation (see Haslam, *Tetrahedron,* 36, (1980), 2409–2433, above). After 12 hours, a gel formed in the flask. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. This gel is pH sensitive.

EXAMPLE 13

Preparation of Hydroxyethylcellulose Gel with 1,2,3,4-Butanetracarboxylic Acid Reagent Exactly 45 mL of DMSO (Fisher Scientific, Catalog No. 03688-4) was added to a distillation flask containing 5 grams of hydroxyethylcellulose (Aqualon, Natrosol 99–250HBR PA) and 2 grams of 1,2,3,4-butanetracarboxylic acid (Aldrich Chemical, Cat. No. 25,730-3), and was mixed for 2 hours, while covered, to achieve a clear colorless solution. To this solution, 500 μL of a 50% (v/v) solution of $H_2SO_4$ in DMSO solution was added, followed by the addition of 5 mL of toluene. This solution was allowed to react under azeotropic distillation (see Haslam, *Tetrahedron,* 36, (1980), 2409–2433). After 12 hours, a gel formed in the flask. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. This gel is pH sensitive.

EXAMPLE 14

Preparation of Hydroxyethylcellulose Gel with 1, 10-Decandicarboxylic Acid Reagent Exactly 45 mL of DMSO (Fisher Scientific, Catalog No. 03688-4) was added to a distillation flask containing 5 grams of hydroxyethylcellulose (Aqualon, Natrosol 99–250HBR PA) and 2 grams of 1,10-Decandicarboxylic Acid (Aldrich Chemical, Cat. No. D100-9), and was mixed for 2 hours, while covered, to achieve a clear colorless solution. To this solution, 500 μL of a 50% (v/v) solution of $H_2SO_4$ in DMSO solution was added, followed by the addition of 5 mL of toluene. This solution was allowed to react under azeotropic distillation (see Haslam, *Tetrahedron*, 36, (1980), 2409–2433). After 12 hours, a gel formed in the flask. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. This gel is pH sensitive.

EXAMPLE 15

Preparation of Hydroxyethylcellulose Gel with Sebacic Acid Reagent

Exactly 45 mL of DMSO (Fisher Scientific, Catalog No. 03688-4) was added to a distillation flask containing 5 grams of hydroxyethylcellulose (Aqualon, Natrosol 99–250HBR PA) and 2 grams of sebacic acid (Aldrich Chemical, Cat. No. 28,325-8), and was mixed for 2 hours, while covered, to achieve a clear colorless solution. To this solution, 500 μL of a 50% (v/v) solution of $H_2SO_4$ in DMSO solution was added, followed by the addition of 5 mL of toluene. This solution was allowed to react under azeotropic distillation (see Haslam, *Tetrahedron*, 36, (1980), 2409–2433). After 12 hours, a gel formed in the flask. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. This gel is pH sensitive.

EXAMPLE 16

Preparation of Hydroxyethylcellulose Gel with Succinic Acid Reagent 45 mL of DMSO (Fisher Scientific, Catalog No. 03688-4) was added to a distillation flask containing 5 grains of hydroxyethylcellulose (Aqualon, Natrosol 99–250HBR PA) and 2 grams of succinic acid (Aldrich Chemical, Cat. No. 39,805-5), and was mixed for 2 hours, while covered, to achieve a clear colorless solution To this solution, 500 μL of a 50% (v/v) solution of $H_2SO_4$ in DMSO solution was added, followed by the addition of 5 mL of toluene. This solution was allowed to react under azeotropic distillation (see Haslam, *Tetrahedron*, 36, (1980), 2409–2433). After 12 hours, a gel formed in the flask. The gel was then removed, cut into 1×1×1 cm$^3$ cubes, and placed in an excess of deionized water (Millipore Alpha-Q). After 12 hours the water was decanted off, and the vessel was filled with an excess of methanol (ACS grade), and the cubes were allowed to sit in methanol solution for 12 hours. This was followed by 3 more 12 hour washes. The cubes were then dried in a desiccator, and then swollen in deionized water. This gel is pH sensitive.

EXAMPLE 17

Preparation of Cosmetic Composition

GELS

A gel containing a fragrance or an active ingredient according to the present invention includes the following materials:

a) distilled water: 65.1 %; crosslinked KATP hydroxypropylcellulose gel: 5.0%; methylparaben: 0.17%; propylparaben: 0.03%; and b) polyoxethylene (20) sorbitan trioleate: 0.3 %; sorbitan monooleate: 0.15 %; caprylic/capric acid triglyceride: 2.5% and;

c) distilled water: 20. 1 %; triethanolamine: 0.8% and;

d) active ingredient: 5.0%

Preparation of the gel is carried out as follows:

For obtaining a), the KATP responsive gel is expanded to incorporate the remaining components. Components of b) are also introduced by expanding the gel. The aqueous triethanolamine solution c) is added under stirring; finally, composition d) is added under stirring. Alternately, the gel is expanded to incorporate all the remaining components c) and d).

The present invention also provides for the loading of biologically active solutes into safe, responsive crosslinked polysaccharide gel networks in a manner that the activity of the solutes are protected against exposure to thermal and chemical challenges. The compound is a biologically active solute and may be a solute having a molecular weight greater than about 1,000 and is preferably selected from the group including proteins, polypeptides, nucleoproteins, glycoproteins and lipoproteins. Applications for loaded molecules into safe responsive crosslinked polysaccharide gel networks include, but are not limited to, cosmetic formulations using papain, therapeutics such as peroxidase catalyzed antibacterials or oral hepatitis B vaccine, over the counter products using peroxidase catalyzed antibacterials in mouthwash or toothpaste that require protection of an enzyme from formulation excipients such as sodium dodedcyl sulfate, lactose intolerance medications, stabilization of molecular biology enzymes such as restriction endonucleases allowing for greater shipping and storage flexibility with respect to temperature, loading of enzymes into gel networks for use in blood panel diagnostics or other types of diagnostics including the use of luciferase and ATP (adenosine triphosphate) and the use of loaded enzymes for bioremediation including the clean up of hydrazine spills with specific hydrazine degrading enzymes.

The present invention further describes the effects of modulating parameters for loading safe responsive crosslinked polysaccharide gel networks such as hydroxy propyl cellulose crosslinked with adipic acid (HPCAA) using loading solutions containing PVA (poly vinyl alcohol) or PLURONIC® (PLURONIC® P105) as phase separating polymers at varying concentrations having a pH above and below the isoelectric point of the protein to be loaded with either potassium iodide or potassium fluoride at varying concentrations.

EXAMPLE 18

Investigation of Loading Solution Factors on Biologically Active Solute (e.g. peroxidase) Loading into Crosslinked Polysaccharide Gel Network (HPCAA Hydrogel)

A study was conducted using a factorially designed experiment to determine the effects of modulating loading solution parameters. Loading solutions were prepared as outlined in Table 5 below. The PVA that was used in this study was maximally hydrolyzed by dissolving the PVA in a 10% NaOH solution with heat. The solution was adjusted to pH 5 and pH 9 with HCL. The molecular weight of the PVA was approximately 10,000. The PLURONIC® was grade P105 avalable from BASF. It was adjusted with HCL NaOH to obtain pH 5 and pH 9 solutions.

TABLE 5

Peroxidase Study

| Run | pH (pH) | Polymer | Polymer Concen. (%) | Salt Type | Salt Concen. | Load Response |
|---|---|---|---|---|---|---|
| 1 | 5. | PLURONIC® | 2. | KI | 0.20 | 2.433 |
| 2 | 9. | PLURONIC® | 2. | KI | 0.05 | 2.358 |
| 3 | 5. | PVA | 2. | KI | 0.05 | 1.735 |
| 4 | 9. | PVA | 2. | KI | 0.20 | 1.830 |
| 5 | 5. | PLURONIC® | 10. | KI | 0.05 | 1.498 |
| 6 | 9. | PLURONIC® | 10. | KI | 0.20 | 1.610 |
| 7 | 5. | PVA | 10. | KI | 0.20 | 0.035 |
| 8 | 9. | PVA | 10. | KI | 0.05 | 2.975 |
| 9 | 5. | PLURONIC® | 2. | KF | 0.05 | 2.850 |
| 10 | 9. | PLURONIC® | 2. | KF | 0.20 | 2.240 |
| 11 | 5. | PVA | 2. | KF | 0.20 | 1.637 |
| 12 | 9. | PVA | 2. | KF | 0.05 | 1.429 |
| 13 | 5. | PLURONIC® | 10. | KF | 0.20 | 2.034 |
| 14 | 9. | PLURONIC® | 10. | KF | 0.05 | 3.701 |
| 15 | 5. | PVA | 10. | KF | 0.05 | 1.060 |
| 16 | 9. | PVA | 10. | KF | 0.20 | 1.920 |

TABLE 5-continued

Approximately 50 mg of dry HPCAA gel was placed into 1.25 ml of the loading solution and stored at room temperature for 24 hours. The samples were them centrifuged and the supernatant loading solution was removed. The mass of removed supernatant was recorded and assumed to have a density of close to 1 allowing to equate a gram of supernatant removed to equal a milliliter of solution for use in the calculation of peroxidase loaded into the gel network. The concentration of peroxidase in the initial loading solutions and the supernatant loading solutions were determined spectrophotometrically. The load of peroxidase/mg dry gel was calculated as follows:

$$\frac{\{(LS \text{ volume} \times LS \text{ concentration}) - \text{supernatant mass} \times \text{supernatant concentration})\}}{HPCAA \text{ gel mass}}$$

where LS is the loading solution. Data used in the calculation is presented in Table 6.

The calculated loads were entered into the experimental design. Pareto Chart Response Surface Plots and Interaction Plots were constructed and are illustrated in FIGS. 4–19. The results indicate that the interaction between pH and polymer concentration has the greatest effect followed by the polymer type, pH and then the salt concentration. In general, the higher the polymer concentration (up to about 10%) and maintaining the pH above the isoelectric point of the protein, the higher the load irrespective of the polymer type. This was also found to occur irrespective of salt type or salt concentration when the polymer was PVA. When the polymer was PLURONIC® P105 (BASF), however, it was discovered that as salt concentration increases from 0.05M to 0.200M, higher loading is obtained at a pH below the isoelectric point of the protein irrespective of salt type.

TABLE 6

PEROXIDASE LOAD OPTIMIZATION
Loading Solution Volume: 1.25 ml

| Raw Data Sample # | Loading Solutions (mg) Dry HPCAA | Loading Solutions (in mm) Peak Height | Loading Solutions (mg/ml) Enzyme conc. | Supernatant Solutions (in mm) Peak Height | Supernatant Solutions (mg/ml) Enzyme conc. | Supernatant Mass Total wt. (grams) tt, gel + sup | Supernatant Mass (grams) Total − sup | (grams) Sup wt. | Peroxidase Load μg/mg gel |
|---|---|---|---|---|---|---|---|---|---|
| 1 | 50.4 | 35 | 0.21 | 33.5 | 0.201 | 2.2314 | 1.5355 | 0.6959 | 2.433 |
| 2 | 50.4 | 37 | 0.2 | 35.5 | 0.192 | 2.2314 | 1.5478 | 0.6836 | 2.358 |
| 3 | 51.6 | 43 | 0.2 | 47 | 0.219 | 2.242 | 1.508 | 0.734 | 1.735 |
| 4 | 50.3 | 39 | 0.2 | 45 | 0.231 | 2.2613 | 1.5769 | 0.6844 | 1.830 |
| 5 | 49.8 | 38 | 0.18 | 43 | 0.204 | 2.2509 | 1.5126 | 0.7383 | 1.498 |
| 6 | 50.3 | 38 | 0.19 | 44.5 | 0.223 | 2.2635 | 1.56 | 0.7035 | 1.610 |
| 7 | 51.6 | 36.5 | 0.22 | 51 | 0.307 | 2.235 | 1.3462 | 0.8888 | 0.035 |
| 8 | 50.1 | 36 | 0.21 | 28 | 0.163 | 2.1564 | 1.4618 | 0.6946 | 2.975 |
| 9 | 49.6 | 28.5 | 0.18 | 22 | 0.139 | 2.2317 | 1.6299 | 0.6018 | 2.850 |
| 10 | 49.2 | 30 | 0.21 | 27.5 | 0.193 | 2.2342 | 1.4431 | 0.7911 | 2.240 |
| 11 | 51.8 | 23.5 | 0.19 | 22.5 | 0.182 | 2.2522 | 1.4127 | 0.8395 | 1.637 |
| 12 | 49 | 13.5 | 0.19 | 16.5 | 0.232 | 2.2295 | 1.5082 | 0.7213 | 1.429 |
| 13 | 50.4 | 27 | 0.21 | 26.5 | 0.206 | 2.2407 | 1.4645 | 0.7762 | 2.034 |
| 14 | 51.4 | 20.5 | 0.2 | 11.5 | 0.112 | 2.2371 | 1.7045 | 0.5326 | 3.701 |

TABLE 6-continued

PEROXIDASE LOAD OPTIMIZATION
Loading Solution Volume: 1.25 ml

| | | Loading Solutions | | Supernatant Solutions | | Supernatant Mass | | | Peroxidase |
|---|---|---|---|---|---|---|---|---|---|
| Raw Data Sample # | (mg) Dry HPCAA | (in mm) Peak Height | (mg/ml) Enzyme conc. | (in mm) Peak Height | (mg/ml) Enzyme conc. | Total wt. (grams) tt, gel + sup | (grams) Total − sup | (grams) Sup wt. | Load µg/mg gel |
| 15 | 49.7 | 20 | 0.19 | 20.5 | 0.195 | 2.2009 | 1.2518 | 0.9491 | 1.060 |
| 16 | 51.9 | 34 | 0.21 | 32.5 | 0.201 | 2.205 | 1.3937 | 0.8113 | 1.920 |

EXAMPLE 19

Loading Peroxidase into HPCAA Hydrogel and Demonstrating Thermal and Chemical Stability I. Introduction The encapsulation of an enzyme into a hydrogel in order to protect and maintain its biological activity from thermal and chemical degradation was conducted in connection with the use of encapsulated enzymes for biological remediation of hydrazine spills. Peroxidase was chosen as a model enzyme with which to demonstrate the feasibility of loading and activity retention from a hydrogel material.

II. Experimental

Gel Selection: A biodegradable crosslinked polysaccharide gel network synthesized by crosslinking hydroxypropyl cellulose with adipic acid (HPCAA) was prepared. This gel was selected due to the requirements of the proposal for having the gel components be on the FDA GRAS list.

Enzyme Loading: A proprietary technique based on two phase protein extraction was employed for loading the HPCAA gel with peroxidase. This technique takes advantage of the phase separation behavior of different hydrophilic polymers and the ability to control the partitioning of a protein or enzyme by manipulating the components of one of the phases. In this case, the hydrogel to be loaded represents one phase that is placed into a second solution phase containing a phase separating polymer, a salt and the enzyme to be loaded. The hydrophilic nature of the polymers provides a gentle environment from which proteins and enzymes can be loaded with minimal degradation.

Optimized loading can be accomplished by varying the amount and type of polymer and salt as well as the solution pH of the loading solution based on the physico-chemical properties of the protein to be loaded. It is not in the scope of this feasibility study to develop optimized loading conditions for peroxidase. The purpose of this Example is to demonstrate that once loaded, the gel can maintain the loaded enzyme's activity after being subjected to thermal and chemical challenges. In this Example, 0.93 g of <300 micron HPCAA gel particles were placed into a 15 ml conical centrifuge tube containing 13.97 ml loading solution (10% PVA, 0.22M potassium chloride, pH 7.0 and 0.2 mg/ml peroxidase). The slurry was maintained at ambient room temperature for 48 hours to allow complete partitioning. The slurry was then centrifuged at approximately 3500 rpm for 20 minutes. The supernatant was removed and the mass recorded.

The concentration of the supernatant was measured by a comparison of peak heights at 400 nm from spectral scans generated by a Shimadzu 1601 UV/Vis Spectrophotometer of the supernatant vs. the original loading solution. Wet loaded gel particles were placed in a desiccator containing $P_2O_5$ for 48 hours to remove residual water. The resulting dried loaded particles were finally ground with a mortar and pestle to mix and obtain uniform particle size. The amount of peroxidase in the gel was determined by the mass balance of enzyme remaining in the supernatant and the amount in the original loading solution.

Stability Challenge: Peroxidase loaded gel particles were challenged both thermally and chemically. Thermal challenge conditions were 60° C. for eight days. Chemical challenge consisted of placing loaded gel particles in 1% sodium dodecyl sulfate solution for eight days at 60° C. Both free enzyme and loaded particles were placed at the thermal and chemical challenge conditions.

Activity Determination: Peroxidase activity was determined using a calorimetric assay in which peroxidase catalyzes the breakdown of hydrogen peroxide generating a free radical that causes the oxidation of guaiacol to a brownish color emitting compound with an absorbance at 436 nm. Activity can be measured by monitoring the change in absorbance with time.

The activity assay reaction solution consisted of 1.5 ml 0.1M phosphate buffer, pH 7.0; 0.240 ml 0.20M guaiacol solution; 0.060 ml 0.008M hydrogen peroxide solution; 0.120 ml DI water. These components were placed into a 3 ml quartz cuvette to which the material to be tested was added.

Free enzyme could not be measured reliably in the dry form in a quantity small enough to be assayed due to the sensitivity of the method. Therefore, free enzyme had to be prepared as a 0.005 mg/ml solution just prior to assay of which 24 µl was added to the cuvette containing reaction solution.

Dried peroxidase loaded gel particles were weighed and directly added to the reaction solution. Activity was measured using the kinetics mode on the Shimadzu 1601 UV/Vis Spectrophotometer. Activity was measured from 5 minutes to 15 minutes after a 5 minute lag to allow for gel settling after introduction and mixing of gel particles and the reaction solution by inverting the cuvette five times. From these activity measurements, activity per mg gel and mg free enzyme could be determined.

Figure 20:
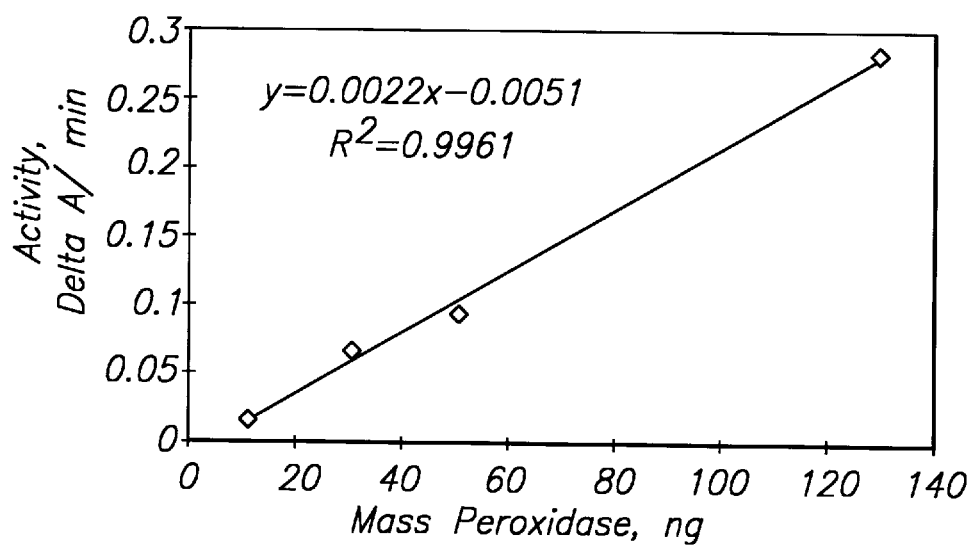
FIG. 20 is a graph of activity v. peroxidase mass.

A curve of activity vs. peroxidase mass was constructed so that apparent enzyme activity could be measured. The graph is depicted in FIG. 20.

III. Results and Discussion

The amount of peroxidase loaded into gel particles as determined by mass balance of enzyme remaining in the loading solution supernatant was calculated to be 500 ng/mg dry gel. This quantity represents a loading efficiency of 0.05% as expressed in mg enzyme/100 mg gel.

The peroxidase activity measurement obtained from dry gel was used to determine the amount of apparent peroxidase load in the gel particles from the activity/ng peroxidase calibration curve outlined previously. The amount of apparent peroxidase load per mg dry gel was 21 ng. When this is compared to the actual load as determined by mass balance, a 24 time reduction in activity is observed. This loss in activity might be attributed to conformational inhibition of enzyme active sights by the gel.

Figure 21:
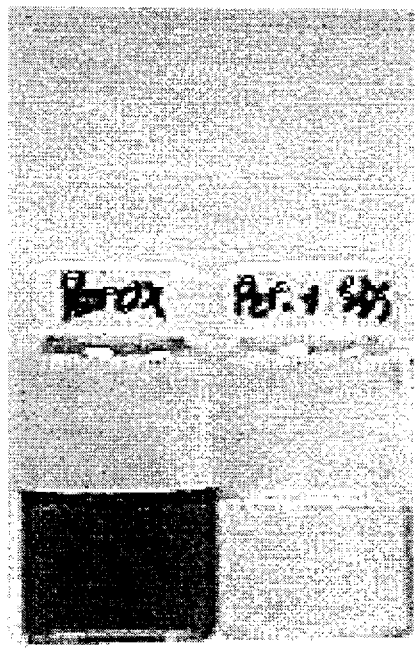
FIG. 21 is an activity indication of free peroxidase before and after exposure to denaturant (1% sodium dodecyl sulfate solution)
Figure 22:
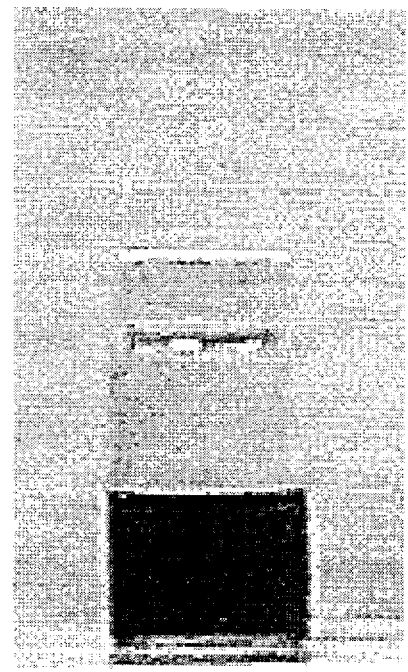
FIG. 22 is an activity indication of peroxidase loaded into crosslinked polysaccharide gel network (HPCAA hydogel) after exposure to denaturant (1% sodium dodecyl sulfate solution at 45° C. for 24 hours)

Activity retention following the stability challenges outline previously are reported in Table 7. The results indicate a curious phenomena for loaded gel in that activity/mg dry gel is actually higher after the thermal and chemical challenge. Free enzyme exhibited a decrease in activity. Stability of peroxidase loaded into safe responsive crosslinked polysaccharide gel networks in the presence of a chemical challenge can be demonstrated on FIGS. 21 and 22. FIG. 21 illustrates qualitatively the elimination of peroxidase activity after exposure of free enzyme to 1% sodium dodecyl sulfate (SDS) solution for an hour at room temperature. The peroxidase in the vial prior to exposure to 1% SDS shows the characteristic color change whereas the vial exposed to SDS does not generate any color indicating the destruction of enzyme activity. As shown in FIG. 22, peroxidase loaded into hydrogel, dried and placed into a 1% SDS solution for 24 hours at 45° C. demonstrates activity by catalyzing the peroxidase specific reaction and generating the characteristic activity indicating color.

TABLE 7

Peroxidase Activity Retention After Stability Challenge

| Peroxidase Environment | Stability Condition | Activity/mg, t = 0 | Activity/mg, 8 Days | % Activity Retained |
|---|---|---|---|---|
| Dry, Loaded HPCAA Gel | 60° C. | 0.229 | 1.451 | 634 |
| | 1% SDS Solution @ 60° C. | 0.005 | 0.053 | 1060 |
| Free Dry Enzyme | 60° C. | 1882 | 1136 | 60 |

Based on these results, it can be concluded that loading biodegradable crosslinked polysaccharide gel network with peroxidase can protect the enzyme's activity when thermally and chemically challenged.

EXAMPLE 20

Loading Acid Phosphatase into HPCAA Hydrogel and Demonstrating Thermal Stability I. Introduction The encapsulation of an enzyme into a hydrogel in order to protect and maintain its biological activity from thermal and chemical degradation was conducted in connection with the use of encapsulated enzymes for degradation of polyurethane aircraft coatings. Acid phosphatase was chosen as a model enzyme with which to demonstrate the feasibility of loading and activity retention from a hydrogel material.

II. Experimental

Gel Selection: A biodegradable crosslinked polysaccharide gel network synthesized by crosslinking hydroxypropyl cellulose with adipic acid (HPCAA) was prepared. This gel was selected due to the requirements of the proposal for having the gel components be on the FDA GRAS list.

Enzyme Loading: A proprietary technique based on two phase protein extraction was employed for loading the HPCAA gel with acid phosphatase. This technique takes advantage of the phase separation behavior of different hydrophilic polymers and the ability to control the partitioning of a protein or enzyme by manipulating the components of one of the phases. In this case, the hydrogel to be loaded represents one phase that is placed into a second solution phase containing a phase separating polymer, a salt and the enzyme to be loaded. The hydrophilic nature of the polymers provides a gentle environment from which proteins and enzymes can be loaded with minimal degradation.

Optimized loading can be accomplished by varying the amount and type of polymer and salt as well as the solution pH of the loading solution based on the physico-chemical properties of the protein to be loaded. It is not in the scope of this feasibility study to develop optimized loading conditions for acid phosphatase. The purpose of this Example was to demonstrate that once loaded, the gel can maintain the loaded enzyme's activity after being subjected to thermal and chemical challenges.

In this Example, 173 mg of <300 micron HPCAA gel particles were placed into a 15 ml conical centrifuge tube containing 2.0 ml loading solution (10% PVA, 0.22M potassium chloride, pH 7.0 and 1.0 mg/ml acid phosphatase). The slurry was maintained at ambient room temperature for 48 hours to allow complete partitioning. The slurry was then centrifuged at approximately 3500 rpm for 20 minutes. The supernatant was removed and the mass recorded.

The concentration of the supernatant was measured by a comparison of peak heights at 280 nm from spectral scans generated by a Shimadzu 1601 UV/Vis Spectrophotometer of the supernatant vs. the original loading solution. Wet loaded gel particles were placed in a desiccator containing $P_2O_5$ for 48 hours to remove residual water. The resulting dried loaded particles were finally ground with a mortar and pestle to mix and obtain uniform particle size. The amount of acid phosphatase in the gel was determined by the mass balance of enzyme remaining in the supernatant and the amount in the original loading solution.

Stability Challenge: Acid phosphatase loaded gel particles were challenged both thermally and chemically. Thermal challenge conditions were 60° C. for six days. Chemical challenge consisted of placing free enzyme in a solution of 10% 1-methyl-2-pyrrolidinone 90% water representing a possible benign polyurethane swelling solvent for four hours at ambient room temperature. Both free enzyme and loaded particles were placed at the thermal challenge conditions. Only free enzyme was tested at the chemical challenge condition.

Activity Determination: Acid phosphatase activity was determined using a Sigma Test Kit in which acid phosphatase catalyzes the breakdown of p-nitrophenyl to p-nitrophenol, a color emitting compound with an absorbance at 410 nm. Activity can be measured by monitoring the change in absorbance with time.

The activity assay reaction solution comes from the Sigma Test Kit. It contains all reagents in a lyophilized form that is reconstituted prior to use. A 1.5 ml volume of the reconstituted reaction solution is placed into a 3 ml quartz cuvette to which the material to be tested was added.

Free enzyme could not be measured reliably in the dry form in a quantity small enough to be assayed due to the sensitivity of the method. Therefore, free enzyme had to be prepared as a 0.1 mg/ml solution just prior to assay of which 100 $\mu$l was added to the cuvette containing reaction solution.

Dried acid phosphatase loaded gel particles were weighed and directly added to the reaction solution. Activity was measured using the kinetics mode on the Shimadzu 1601 UV/Vis Spectrophotometer. Activity was measured from 5 minutes to 15 minutes after a 5 minute lag to allow for gel settling after introduction and mixing of gel particles and the reaction solution by inverting the cuvette five times. From these activity measurements, activity per mg gel and mg free enzyme could be determined.

Figure 23:
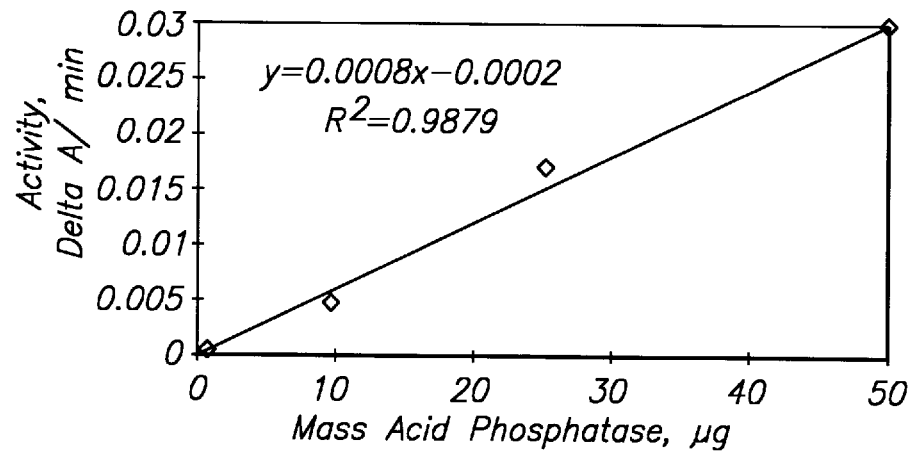
FIG. 23 is a graph of activity v. acid phosphatase mass in connection with Example No. 20.

A curve of activity vs. acid phosphatase mass was constructed so that apparent enzyme activity could be measured. The graph is depicted in FIG. 23.

III. Results and Discussion

The amount of acid phosphatase loaded into gel particles as determined by mass balance of enzyme remaining in the loading solution supernatant was calculated to be 7.48 μg/mg dry gel. This quantity represents a loading efficiency of 0.75% as expressed in mg enzyme/100 mg gel.

The acid phosphatase activity measurement obtained from dry gel was used to determine the amount of apparent acid phosphatase load in the gel particles from the activity/ng acid phosphatase calibration curve outlined previously. The amount of apparent acid phosphatase load per mg dry gel was 0.44 μg/mg dry gel. When this is compared to the actual load of 7.48 μg/mg dry gel as determined by mass balance, a 17 time reduction in activity is observed. This loss in activity might be attributed to conformational inhibition of enzyme active sights by the gel.

Activity retention following the stability challenges outline previously are reported in Table 8. The results indicate a maintenance of activity after the thermal challenge. Free enzyme exhibited a decrease in activity.

TABLE 8

Acid phosphatase Activity Retention After Stability Challenges

| Acid Phosphatase Environment | Stability Condition | Activity/mg, t = 0 | Activity/mg, 6 Days | % Activity Retained |
|---|---|---|---|---|
| Dry, Loaded HPCAA Gel | 60° C. | 0.00007 | 0.00007 | 100 |
| Free Dry Enzyme | 60° C. | 0.582 | 0.400 (2 days) | 69 |
| Free Enzyme | 10% 1-methyl-2-pyrrolidinone/ 90% water Solution | 0.582 | 0.548 (4 hrs) | 94 |

Based on these results, it can be concluded that loading biodegradable crosslinked polysaccharide gel network with acid phosphatase can protect the enzyme's activity when thermally challenged. The free enzyme is able to withstand the proposed benign polyurethane swelling solvent, that could contain as much as 10% of either n-methyl-pyrrolidinone, butanol or benzyl alcohol.

EXAMPLE 21

Loading β-Galactosidase into HPCAA and Demonstrating Activity

Lactose intolerance is caused by a lactase enzyme deficiency, and results in osmotic diarrhea after the consumption of dairy products. The current in vivo-acting lactase products contain β-galactosidase, which acts by hydrolyzing the lactose into digestible components. This enzyme is subjected to a first pass metabolism consisting of proteolytic enzymes that degrade the lactase enzyme. Therefore a repeated dosage of lactase is needed. These products are delivered by standard tabletting techniques that are not designed to protect the enzyme in situ. We have developed a novel loading technology that allows for loading and activity retention of high MW proteins into pre-formed hydrogels. See also Gehrke, et al., Proceed. Intern. Symp. Control. Rel. Bioact. Matter, 22:145 (1995). We have also developed unique crosslinked polysaccharide gel networks (e.g., hydrogels) that are collapsed at low pH (<4) and are swollen at high pH (>4). We have loaded these hydrogels with β-galactosidase (MW 540,000).

Figure 24:
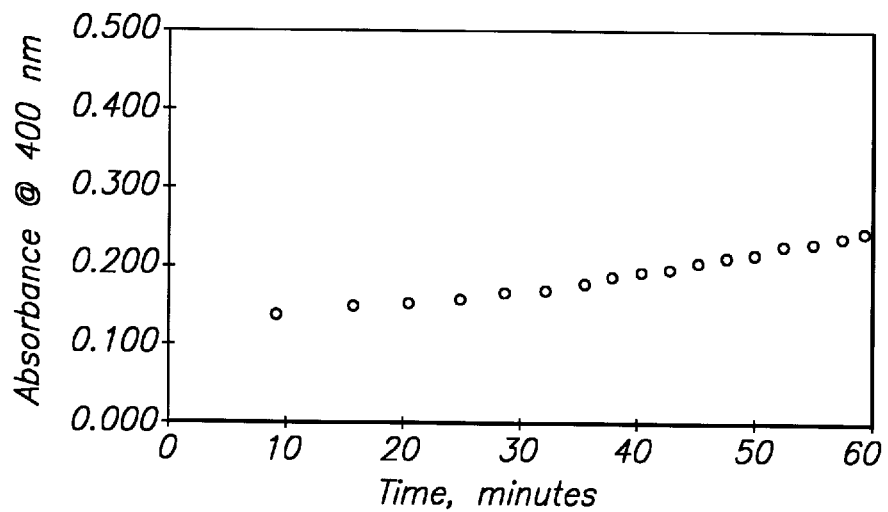
FIG. 24 is a graph of absorbance v. time for β-galactosidase activity from loaded crosslinked polysaccharide gel network (hydrogel)

Safe responsive crosslinked polysaccharide gels were loaded with β-galactosidase by first swelling 300–600 micron particles of HPCAA in deionized water. The resulting slurry was centrifuged and the deionized supernatant was removed. A loading solution containing 8% PLURONIC® P105, 0.22M potassium chloride at pH 6.86 and 20 mg/ml of β-galactosidase was prepared. The loading solution was placed into a 15 ml conical centrifuge vial and 0.5429 g of previously swollen gel was added. The contents of the vial were allowed to equilibrate for 24 hours at 28° C. The vial was then centrifuged and the loading solution supernatant was removed. The particles remaining in the centrifuge vial were rinsed and centrifuged 3 times with 0.1M NaCl to remove β-galactosidase adsorbed onto the surface. The loaded gel particles were placed into a cuvette. A substrate solution containing p-nitrophenyl β-D-galactopyranoside and lactose at pH 8 was added. The change in absorbance at 400 nm was monitored over time The plot indicating activity of β-galactosidase from the gel network is shown in FIG. 24.

EXAMPLE 22

Loading and Release of Hepatitus B Surface Antigen from Crosslinked Polysaccharide Gel Network I. Introduction In this Example, the development of an oral hepatitis B (HBsAg) formulation using crosslinked polysaccharide gel network was analyzed and involved loading HBsAg into the hydrogel which will provide a stabilizing matrix for the protein by protecting it from gastric acidity and proteases. The hydrogel will remain collapsed in the pH of the stomach and expand at the higher pH encountered in the upper intestinal tract where it will be released. This Example also describes the loading process, the amount of HBsAg loaded and the release kinetics of HBsAg from the hydrogel.

II. Experimental

Gel Selection: A crosslinked polysaccharide gel network was synthesized using materials found on the US FDA GRAS ("generally regarded as safe") list by crosslinking hydroxypropyl cellulose with adipic acid (HPCAA). A preliminary toxicological evaluation of this material has not demonstrated any toxicity.

Quantitative HBsAg Method Development: A hepatitis B surface antigen formulation prepared by Dong Shin Pharmaceuticals from SmithKline Beecham Lot No. HEP419 was received and immediately refrigerated. Upon opening, it was observed that the formulation sent had an opaque quality that could be cleared upon filtering with a low protein binding 0.22 μ filter.

The concentration of HBsAg in the filtrate was determined by the Bicinchonic Acid Assay and determined to be approximately 24 μg/ml. A spectral scan of the filtrate was obtained using a Shimadzu 1601 UV/Vis Spectrophotometer with a maxima detected at 263 nm. The absorbance of the filtrate at 263 nm was assigned the concentration of HBsAg obtained from the BCA assay. Dilutions of the HBsAg filtrate were prepared and a calibration curve generated for use as an analytical tool in determining concentrations of HBsAg in loading solutions and release study samples.

Crosslinked Polysaccharide Gel Network Loading: Theories used in a proprietary technique based on two phase protein extraction was employed for loading the HPCAA gel with HBsAg. The technique takes advantage of the phase separation behavior of different hydrophilic polymers and the ability to control the partitioning of a protein or enzyme by manipulating the components of one of the phases. Optimized loading can be accomplished by varying the amount and type of polymer and solution of pH as well as salt species and concentration of the loading solution based on the physico-chemical properties of the protein to be loaded.

In this Example, the hydrogel to be loaded represents one phase that is placed in to a second solution phase that normally contains a phase separating polymer, a salt and the protein to be loaded. However, due to the low concentration of HBsAg in the filtrate, the addition of a polymer solution to obtain an optimal loading solution polymer concentration in the range of 10% would dilute the filtrate to a point where the HBsAg level would be too low. Adding polymer directly to the filtrate was not performed due to stability concerns for the protein because of time and temperature requirements necessary to get polymers into solution.

An initial loading study was conducted to determine the level of HBsAg loading into crosslinked polysaccharide gel network (HPCAA hydrogel) and release kinetics. Two loading solutions were investigated. One solution was the filtrate obtained from the original formulation provided by Dong Shin Pharmaceutical. The other contained the addition of 0.22M potassium chloride to affect the partitioning of the protein. Five mls of each loading solution was added to 300 mg of <300 micron HPCAA gel particles in 15 ml conical centrifuge tubes. The hydrogel was allowed to swell and equilibrate for 48 hours at 2°–8° to allow complete partitioning. The slurry was then centrifuged at approximately 3950 rpm for 20 minutes. The supernatant was removed and the mass recorded.

The concentration of the supernatant was determined by UV spectrophotometry using the calibration curve obtained as described previously. Wet loaded gel particles were placed in a desiccator containing Dreirite anhydrous calcium sulphate dessicant. The resulting dried loaded particles were finally ground with a mortar and pestle to mix and obtain uniform particle size. The amount of HBsAg in the hydrogel was determined by the mass balance of protein remaining in the supernatant and the amount in the original loading solution.

Release Study: The release of HBsAg from crosslinked polysaccharide gel network (HPCAA hydrogel) was determined by placing approximately 80 mg of loaded hydrogel into a 5 ml vial containing 3 ml PBS. The slurries were stirred with a stir bar at ambient room temperature. At predetermined time intervals, the slurries were removed from the stir plate and the hydrogel allowed to settle to the bottom of the vial. Using a pipet, 1 ml samples were removed carefully trying to minimize uptake of hydrogel and replaced with 1 ml of fresh PBS. Before determining the HBsAg concentration by UV spectrophotometry, samples were centrifuged to ensure no suspended hydrogel particles would interfere with the spectrophotometer reading. Supernatant was transferred to quartz cuvettes for concentration determination.

III. Results and Discussion

Figure 25:
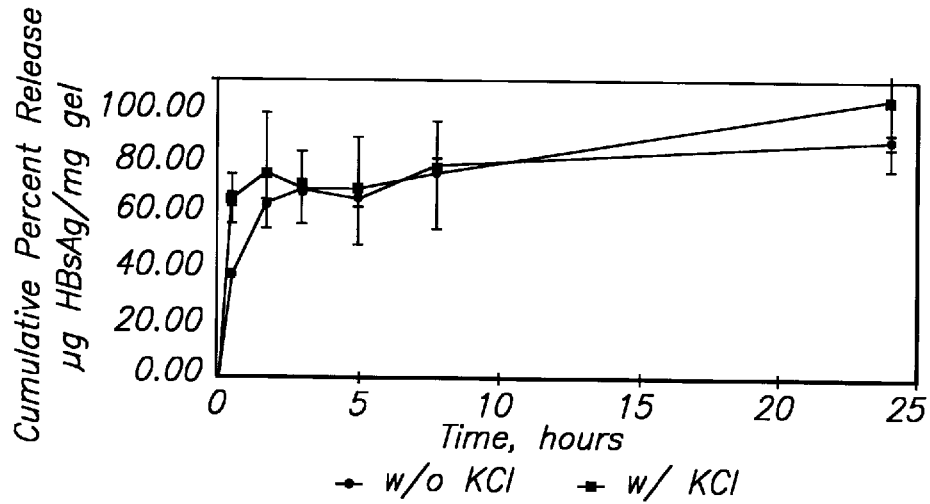
FIG. 25 is a graph of cumulative percent release v. time for hepatitus B surface antigen release from loaded crosslinked polysaccharide gel network (HPCAA hydrogel particles).

The loading of HBsAg into the safe responsive crosslinked polysaccharide gel network was determined by mass balance as described in Example 18. The amounts loaded were 0.281 mg/mg dry gel when no KCl was added and 0.327 mg/mg dry gel when 0.22 KCl was added. The release of hepatitis B surface antigen vaccine is shown in FIG. 25. The vaccine is released almost completely into PBS indicating that the hydrogel network can be used to carry the vaccine for possible oral delivery.

It should be appreciated by those skilled in the art that the specific embodiments disclosed above may readily be utilized as a basis for modifying or designing other methods or structures for carrying out the same purpose of the present invention. It should also be realized by those skilled in the art that such equivalent constructions do not depart from the spirit and scope of the invention as set forth in the appended claims.

What is claimed is:

1. A method of loading a biologically active solute into a crosslinked polymer gel network, comprising:

selecting the crosslinked polymer gel network;

forming a loading polymer solution, the loading polymer solution comprising a loading polymer, a salt and the biologically active solute, the lading polymer solution having a pH above the isoelectric point of the biologically active solute; and contacting the crosslinked polymer gel network with the loading polymer solution under conditions sufficient for at least a portion of the loading polymer solution to partition into the gel network and for at the biologically active solute to retain activity while in the gel network.

2. The method of claim 1, wherein the crosslinked polymer gel network is biodegradable.

3. The method of claim 1, wherein the crosslinked polymer gel network is a polysaccharide polymer gel.

4. The method of claim 3, wherein the crosslinked polysaccharide polymer gel network is hydroxypropyl cellulose crosslinked with adipic acid.

5. The method of claim 3, wherein the biologically active solute is a protein.

6. The method of claim 5, wherein the protein is an enzyme.

7. The method of claim 6, wherein the enzyme is peroxidase.

8. The method of claim 6, wherein the enzyme is suitable for use in blood panel diagnostics.

9. The method of claim 6, wherein the enzyme is suitable for use in bioremediation.

10. The method of claim 9, wherein the enzyme is tricloroethane.

11. The method of claim 1, wherein the biologically active solute includes hepatitus B surface antigen.

12. The method of claim 6, wherein the enzyme is a hydrazine degrading enzyme.

13. The method of claim 1, wherein the loading polymer comprises polyvinyl alcohol.

14. The method of claim 13, wherein the biologically active solute comprises peroxidase.

15. The method of claim 13, wherein the salt comprises potassium iodide.

16. The method of claim 15, wherein the biologically active solute comprises peroxidase.

17. The method of claim 13, wherein the salt comprises potassium fluoride.

18. The method of claim 17, wherein the biologically active solute comprises peroxidase.

19. The method of claim 1, wherein the loading polymer comprises polyoxyalkylene derivatives of propylene glycol.

20. The method of claim 1, wherein the portion of the loading solution that partitions into the gel network comprises the biologically active solute.

21. A method of loading a biologically active solute into a crosslinked polymer gel network, comprising:

selecting the crosslinked polymer gel network;

forming a loading polymer solution, the loading polymer solution comprising a loading polymer, a salt and the biologically active solute, the loading polymer solution having a pH below the isoelectric point of the biologically active solute; and contacting the crosslinked polymer gel network with the loading polymer solution under conditions sufficient for at least a portion of the loading polymer solution to partition into the gel network and for the biologically active solute to retain activity while in the gel network.

22. The method of claim 21, wherein the loading polymer comprises polyoxyalkylene derivatives of propylene glycol.

23. The method of claim 22, wherein the biologically active solute comprises peroxidase.

24. The method of claim 22, wherein the salt comprises potassium iodide.

25. The method of claim 24, wherein the biologically active solute comprises peroxidase.

26. The method of claim 22, wherein the salt comprises potassium fluoride.

27. The method of claim 26, wherein the biologically active solute comprises peroxidase.

28. The method of claim 21, wherein the crosslinked polymer gel network comprises a crosslinked polysaccharide gel network.

29. The method of claim 21, wherein the portion of the loading solution that partitions into the gel network comprises the biologically active solute.

* * * * *